(12) United States Patent
Langham et al.

(10) Patent No.: US 6,403,608 B1
(45) Date of Patent: Jun. 11, 2002

(54) 3-SUBSTITUTED ISOQUINOLIN-1-YL DERIVATIVES

(75) Inventors: Barry John Langham, Reading; Rikki Peter Alexander, High Wycombe; John Clifford Head, Maidenhead; Janeen Marsha Linsley, High Wycombe; John Robert Porter; Sarah Catherine Archibald, both of Slough; Graham John Warrellow, Northwood, all of (GB)

(73) Assignee: Celltech R&D, Ltd., Berkshire (GB)

( * ) Notice: Subject to any disclaimer, the term of this patent is extended or adjusted under 35 U.S.C. 154(b) by 0 days.

(21) Appl. No.: 09/867,060

(22) Filed: May 29, 2001

(30) Foreign Application Priority Data

| May 30, 2000 | (GB) | 0013087 |
|---|---|---|
| Aug. 3, 2000 | (GB) | 0019060 |
| Nov. 27, 2000 | (GB) | 0028842 |

(51) Int. Cl.⁷ .................. C07D 217/08; A61K 31/47
(52) U.S. Cl. .................. 514/309; 514/307; 514/310; 546/141; 546/143; 546/148
(58) Field of Search ........... 546/141, 143, 546/148; 514/307, 309, 310

(56) References Cited

U.S. PATENT DOCUMENTS

| 4,470,973 A | 9/1984 | Natarajan et al. ........... 424/177 |
|---|---|---|
| 4,554,273 A | 11/1985 | Bayssat et al. ............. 514/221 |
| 4,987,132 A | 1/1991 | Mase et al. ................. 514/252 |
| 5,164,372 A | 11/1992 | Matsuo et al. ................ 514/19 |
| 5,227,490 A | 7/1993 | Hartman et al. |
| 5,260,277 A | 11/1993 | McKenzie ................... 544/18 |
| 5,296,486 A | 3/1994 | Lazar et al. ................ 514/333 |
| 5,399,585 A | 3/1995 | Alig et al. .................. 514/438 |
| 5,510,346 A | 4/1996 | Martin et al. ............... 514/221 |
| 5,698,691 A | 12/1997 | Yukimasa et al. .......... 540/490 |
| 5,773,646 A | 6/1998 | Kumar |
| 6,093,696 A | 7/2000 | Head et al. ................... 514/19 |
| 6,166,050 A | 12/2000 | Lombardo et al. ..... 514/352.18 |

FOREIGN PATENT DOCUMENTS

| DE | 23 16 881 A | 10/1973 |
|---|---|---|
| DE | 28 37 264 A1 | 3/1979 |
| DE | 196 54 483 A | 1/1998 |
| EP | 0 031 104 A1 | 7/1981 |
| EP | 0 048 763 A1 | 4/1982 |
| EP | 0 144 230 A2 | 6/1985 |
| EP | 0 288 176 A1 | 10/1988 |
| EP | 0 322 068 A1 | 6/1989 |

(List continued on next page.)

OTHER PUBLICATIONS

Abraham, W.M. et al., "α₄–Integrins Mediate Antigen–Induced Late Bronchial Responses and Prolonged Airway Hyperresponsiveness in Sheep," *J. Clin. Invest.*, 1994, 93, 776–787.

Alhaique, F., et al., "Cyclisation of dinitriles by sodium alkoxides a new synthesis of naphthyridines," *Tetrahedron Letters*, 1975, 3, 173–174.

Ames, D.E., et al., "Condensation of β–dicarbonyl compounds with halogenopyridinecarb–oxylic acids. A convenient synthesis of some naphthyridine derivatives," *J.C.S. Perkin I*, 1972, 705–710.

(List continued on next page.)

Primary Examiner—Zinna Northington Davis
(74) *Attorney, Agent, or Firm*—Woodcock Washburn LLP

(57) ABSTRACT

3-Substituted isoquinoline containing squaric acids of formula (1) are described:

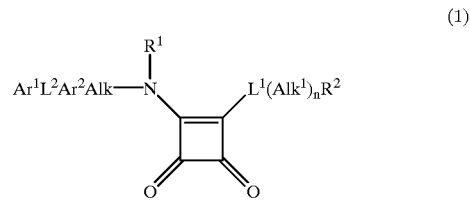

(1)

wherein

Ar¹ is a 3-substituted isoquinolin-1-yl group;

L² is a covalent bond or a linker atom or group;

Ar² is an optionally substituted aromatic or heteroaromatic chain;

Alk is a chain

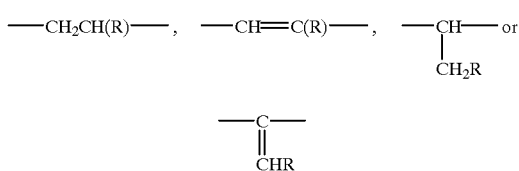

in which

R is a carboxylic acid (—CO₂H) or a derivative or biostere thereof;

R¹ is a hydrogen atom or a $C_{1-6}$alkyl group;

L¹ is a covalent bond or a linker atom or group;

Alk¹ is an optionally substituted aliphatic chain;

n is zero or the integer 1;

R² is a hydrogen atom or an optionally substituted heteroaliphatic, cycloaliphatic, heterocycloaliphatic, polycycloalphatic, heteropolycycloaliphatic, aromatic or heteroaromatic group;

and the salts, solvates, hydrates and N-oxides thereof.

The compounds are able to inhibit the binding of integrins to their ligands and are of use in the prophylaxis and treatment of immune or inflammatory disordes or disorders involving the inappropriate growth or migration of cells.

19 Claims, No Drawings

FOREIGN PATENT DOCUMENTS

| | | |
|---|---|---|
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |
| EP | 0 842 943 A2 | 5/1998 |
| EP | 0 842 945 A2 | 5/1998 |
| JP | 56 090045 | 7/1981 |
| JP | 03 135962 | 6/1991 |
| WO | WO 86/02353 | 4/1986 |
| WO | WO 97/47618 | 12/1987 |
| WO | WO 93/00095 | 1/1993 |
| WO | WO 93/08174 | 4/1993 |
| WO | WO 93/09795 | 5/1993 |
| WO | WO 94/15954 | 7/1994 |
| WO | WO 94/15955 | 7/1994 |
| WO | WO 94/29285 | 12/1994 |
| WO | WO 95/13811 | 5/1995 |
| WO | WO 95/15973 | 6/1995 |
| WO | WO 95/19356 | 7/1995 |
| WO | WO 95/35314 | 12/1995 |
| WO | WO 96/01644 | 1/1996 |
| WO | WO 99/26922 | 6/1996 |
| WO | WO 96/22966 | 8/1996 |
| WO | WO 96/26190 | 8/1996 |
| WO | WO 97/03094 | 1/1997 |
| WO | WO 97/04247 | 2/1997 |
| WO | WO 97/08145 | 3/1997 |
| WO | WO 97/12866 | 4/1997 |
| WO | WO 97/23480 | 7/1997 |
| WO | WO 97/24124 | 7/1997 |
| WO | WO 97/31907 | 9/1997 |
| WO | WO 97/36858 | 10/1997 |
| WO | WO 97/36859 | 10/1997 |
| WO | WO 97/36861 | 10/1997 |
| WO | WO 97/36862 | 10/1997 |
| WO | WO 97/44333 | 10/1997 |
| WO | WO 98/00395 | 1/1998 |
| WO | WO 98/04247 | 2/1998 |
| WO | WO 98/04913 | 2/1998 |
| WO | WO 98/18460 | 5/1998 |
| WO | WO 98/25892 | 6/1998 |
| WO | WO 98/31359 | 7/1998 |
| WO | WO 98/42662 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO 99/26921 | 6/1999 |
| WO | WO 99/26945 | 6/1999 |
| WO | WO 99/30709 | 6/1999 |
| WO | WO 99/31061 | 6/1999 |
| WO | WO 99/31099 | 6/1999 |
| WO | WO 99/32457 | 7/1999 |
| WO | WO 99/35163 | 7/1999 |
| WO | WO 99/36393 | 7/1999 |
| WO | WO 99/37618 | 7/1999 |
| WO | WO 99/43642 | 9/1999 |
| WO | WO 99/44994 | 9/1999 |
| WO | WO 99/48879 | 9/1999 |
| WO | WO 99/52879 | 10/1999 |
| WO | WO 99/52896 | 10/1999 |
| WO | WO 99/52898 | 10/1999 |
| WO | WO 99/60015 | 11/1999 |
| WO | WO 99/61465 | 12/1999 |
| WO | WO 99/64395 | 12/1999 |
| WO | WO 99/67230 | 12/1999 |
| WO | WO 00/00486 | 1/2000 |
| WO | WO 00/01383 | 1/2000 |
| WO | WO 00/06169 | 2/2000 |
| WO | WO 00/07544 | 2/2000 |
| WO | WO 00/17197 | 3/2000 |
| WO | WO 00/20396 | 4/2000 |
| WO | WO 00/23419 | 4/2000 |
| WO | WO 00/31067 | 6/2000 |
| WO | WO 00/35855 | 6/2000 |
| WO | WO 00/73260 | 12/2000 |

OTHER PUBLICATIONS

Azzouny, A.E., et al., "Zur Synthese Acyclischer und Cyclischer Anthranilsäure–Phenylalanin–Peptide ," *Pharmazie*, 1977, 32(6), 318–323 (German language only).

Bach et al., "Anomalous optical rotation and circular dichroism of N–thioacylated alpha amino acids and deriva," *Acta Chem. Scand.*, 1966, 20(10), 2781–2794.

Badshah, A., et al., "Catalytic reduction of azlactones in alkaline media. Synthesis of amino acids," *J. of Organic Chemistry*, 1972, 37(18), 2916–2918.

Barrett, G.C., "Circular dichroism of N–thiobenzoly–1–α–amino acids. III. Their circular dichroism through the near–ultraviolet wavelength range," *J. Chem. Soc.*, 1967, Section C, 1–5.

Berlin, C. et al., "α4β7 Integrin Mediated Lymphocyte Binding to the Mucosal Vascular Addressin MAdCAM–1," *Cell*, 1993, 74, 185–195.

Binns, R.M. et al., "The Role of E–Selectin in Lymphocyte and Polymorphonuclear Cell Reeruitment into Cutaneous Delayed Hypersensitivity Reactions in Sensitized Pigs," *J. Immunol.*, 1996, 157, 4094–409.

Bodor, N., "Novel approaches in prodrug design," *Alfred Benzon Symposium*, 1982, 17, 156–177.

Briskin, M.J. et al., "Structural Requirements for Mucosal Vascular Addressin Binding to Its Lymphocyte Receptor $\alpha_4\beta_7$," *J. Immunol.*, 1996, 156, 719–726.

Brooks, Peter C., et al., "Antiintegrin αvβ3 blocks human breast cancer growth and angiogenesis in human skin," *J. Clin. Invest.*, 1995, 96, 1815–1822.

Buckle, D.R., et al., "Non Thiazolidinedione Antihyperglycaemic Agents. 1: α–Heteroatom Substituted β–Phenylpropanoic Acids," *Bioorg. Med. Chem. Lett.*, 1996, 6(17), 2121–2126.

Bundgaard, H., *Design of Prodrugs*, 1985, Elsevier, Amsterdam.

Cardarelli, P.M. et al., "Cyclic RGD Peptide Inhibits α4β7 Interaction with Connecting Segment 1 and Vascular Cell Adhesion Molecule," *J. Biol. Chem.*, 1994, 269(28), 18668–18673.

"Cephalosporins," *Jpn. Kokai Tokkyo Koho*, 40 pages, doc. No. 99:5433 (abstract only, 2 pages); JP 57118588.

Koho, *Chemical Abstracts*. N–[4–Thiazolidinyl)carbonyl] amino acid derivatives, 1981, 95(19), Abstract No. 169173f, 1 page; JP Patent, XP–002114107.

Clausen, K., et al., "Studies on amino acids and peptides. II. Synthesis of protected endothiodipeptides," *J. Chem. Scr.*, 1982, 20(1–2), 14–18, doc. No. 97:163474 (abstract only, 1 page).

Katritzky, A.R., et al. (Eds.), Comprehensive Organic Functional Group Transformations, Pergamon, 1995.

Corey, E.J. et al., "A Synthetic Method for Formyl → Ethynyl Conversion (RCHO → RC≡CH or RC≡CR$^7$ )," *Tetrahedron Lett.*, 1972, 36, 3769–3772.

Cornforth, J.W., "Oxazoles and Oxazolones," *Chem. Penicillin*, Princeton Book Review, 1949, pp. 688, 799, and 800.

Davies, S..G., et al., "Asymmetric synthesis of R–β–amino butanoic acid and S–β–tyrosine: homochiral lithium amide equivalents for Michael additions to α,β–unsaturated esters," *Tetra Asymmetry*, 1991, 2(3), 183–186.

Erle, D.J., et al., "Expression and function of the MadCAM–1 receptor, integrin α4β7, on human leukocytes," *J. Immunol.*, 1994, 153, 571–528.

Encyclopedia of Reagents for Organic Synthesis,*John Wiley and Sons* (eds.), 1995.

Ferguson, T.A. et al., "Two integrin–binding peptides abrogate T cell–mediated immune responses in vivo," *Proc. Natl. Acad. Sci. USA*, 1991, 88, 8072–8076.

Frank, R., et al., "Extremely mild reagent for Boc deprotection," *Chem. Commun. (Cambridge)*, 1996, 22, 2509–2510, doc. No. 126:104395 (abstract only, 3 pages).

Fu, H. et al., "Preliminary study on synthesis and antitumor activity in vitro of derivatives of timonacic," *Chemical Abstracts*, 1988, 108(17), Abstract No. 150358k, 1 page.

Giacomello, et al., "Synthesis of 2,6–naphthyridine," *Tetra. Letters*, 1965, 16, 1117–1121.

Green, T.W., et al., "Protective Groups in Organic Synthesis," *John Wiley and Sons* (eds.), 1991.

Hammes, H., et al., "Subcutaneous injection of a cyclic peptide antagonist of vitronectin receptor–type integrins inhibits retinal neovascularization," *Nature Medicine*, 1996, 2, 529–533.

Harris, R.L.N. et al., *Aust. J. Chem.*, "Potential wool growth inhibitors. 2(1H)–Pyridone analogs of mimosine," 1977, 30(3), 649–655.

Hanke, K. et al., "Dithio and thiono esters. Part 61. Synthesis of α–amino dithioesters and endothiodipeptides,",*J. Prakt. Chem.*, 1996, 338(3). 251–256.

Hodivala–Dilke, K.M., "β3–integrin–deficient mice are a model for glanzmann thrombasthenia showing placental defects and reduced survival," *J. Clin. Invest.*, 1999, 103(2), 229–238.

Holzmann, B., et al., "Peyer's patch–specific lymphocyte homing receptors consist of a VLA–4–like α chain associated with either of two integrin β chains, one of which is novel," *EMBO J.*, 1989, 8(6), 1735–1741.

Humphries, M.J. et al., "Mechanisms of VCAM–1 and fibronectin binding to integrin $α_4β_1$: implications for integrin function and rational drug design," *Ciba Foundation Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1," *J. Immunol.*, 1992, 149(10), 3394–3402.

Jaynes, B.H. et al., "Synthesis and In Vivo Antibacterial Activity of Hygromycin a Analogs Modified at the $C_4$' Aryl Position," *Bioorg. Med. Chem. Letts.*, 1993, 3(8), 1531–1536.

Jepson, J.B. et al., "Reactions of α–Thioacylamino–acids. Their conversion into Thiazolones and Derivatives Thereof," *J. Chem. Soc.*, 1955, 1791–1797.

Kalvin, D.M., et al., Synthesis of (4R)–D,L–[4–$^2$H]– and (4S)–D,L–[4–$^2$H] homoserine lactones, *J. Org. Chem.*, 1985, 50, 2259–2263.

Keenan, R.M. et al., "Discovery of Potent Nonpeptide Vitronectin Receptor (av$β_3$) Antagonists," *J. Med. Chem.*, 1997, 40(15), 2289–2292.

Kobayashi, A., et al., "Syntheses of 2–dialkylamino–4, 4–disubstituted 5 (4H)–thiazolones," *J. Yakugaku Zasshi*, 1970, 90(11), 1377–1380, doc. No. 74:31713 (abstract only, 3 pages).

Koenig, H.B., et al., ".beta.–Lactam antibiotics," *Ger. Offen.*, 41 pages, doc. No. 83:97276 (abstract only, 5 pages); German patent, 1983.

Koivunen, E., et al., "Selection of peptides binding to the $α_5β_1$entegrin from phage display library," *J. Biological Chemisry*, 1993, 268(27), 20205–20210.

Lei, H. et al., "Efficient Synthesis of a Phosphinate Bis–Amino Acid and Its Use in the Construction of Amphiphilic Peptides," *J. Org. Chem.*, 1994, 59, 4206–4210.

Li, Z. et al., "Effect of an anti–Mol MAb on Ozone–induced airway inflammation and airway hyperresponsiveness in dogs," *Am. J. Physiol.*, 1992, 263(6 Pt 1), L723–726.

Lobb, R.R., et al., "Small molecule antagonists of alpha4 integrins: novel drugs for asthma," *Exp. Opin, Invest. Drugs*, 1999, XP000885957, 8(7), 935–945.

Marlin, S.D. et al., "LFA–1 Immunodeficiency Disease," *J. Exp. Med.*, 1986, 164, 855–867.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan*, 1982, 1 page.

Masuda, T., *Jpn. Kodai Tokkyo Koho*, 22 pages, doc. No. 115:280022 (abstract only, 1 page); JP patent, No Publication. Date.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.*, 1994, 116. 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Mitjans, F., et al., "An anti–αv–integrin antibody that blocks integrin function inhibits the development of a human melanoma in nude mice," *J. Cell Science*, 1995, 108, 2825–2838.

Molina, P., et al., "Iminophosphorane–mediated annelation of a pyridine ring into a preformed pyridine one: synthesis of naphthyridine, pyrido [1,2–c] pyrimidine and pyrido [1,2–c] quinazoline derivatives," *Tetrahedron*, 1992, 48(22), 4601–4616.

Nagasawa, H.T. et al., "β–Substituted Cysteines as Sequestering Agents for Ethanol–Derived Acetaldehyde in Vivo," *J. Med. Chem.*, 1987, 30, 1373–1378.

Newham, P., et al., "Integrin adhesion receptors: structure, function and implications for biomedicine," *Nolecular Medicine Today*, 1996, 304–313.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yagugaku Zasshi*, 1959, 79(12), 1514–1518 (English summary included).

Numata, A., et al., "General synthetic method for naphthyridines and their N–oxides containing isoquinolinic nitrogen," *Synthesis*, 1999, 2, 306–311.

Ohki, S. et al., "Synthesis of quinolizine derivatives. V. Studies on Diastereoisomer of Ethyl 3–Quinolizidinecarboxylate," *Chem. Pharm. Bull.*, 1959, 7(6), 708–712.

Osborne, L., "Leukocrye Adhesion to Endothelium in Inflammation," *Cell*, 1990, 62, 3–6.

Osborn, L. et al., "Direct Expression Cloning of Vascular Cell Adhesion Molecule 1, a Cytokine–Induced Endothelial Protein that Binds to Lymphocytes," *Cell*, 1989, 59, 1203–1211.

Podolsky, D.K. et al., "Attenuation of Colitis in the Cotton–top Tamarin by Anti–α4 integrin Monoclonal Antibody," *J. Clin. Invest.*, 1993, 92, 372–380.

Pfeifer, T., et al., "Specific fragmentation of thioxo peptides facilitates the assignment of the thioxylated amino acid," *J. Mass Spectrom*, 1997, 32(10), 1064–1071, doc. No. 127:331738 (abstract only 2 pages).

Sakamoto, T., et al., "Condensed heteroaromatic ring systems. III. synthesis of naphthyridine derivatives by cyclization of ethynylpyridinecarboxamides," *Chem. Pharm. Bull.* 1985, 33(2), 626–633.

Samanen, J., et al., "Vascular indications for integrin alpha V antagonists," *Current Pharm. Design.*, 1997, 3, 545–584.

Savrda, J., "CIS–TRANS isomerism of N–ACYL derivatives of proline and its analogues, linear peptides with CIS peptide bonds," *Proc. 14$^{th}$ European Peptide Symposium*, Loffet, A. (ed.), 1976, 653–656.

Sawa, N., et al., "Preparation of 4(5)–thiocarbamoylimidazole compounds," *Jpn. Kokai Tokkyo Koho*, 33 pages, doc. No. 115:183296 (abstract only, 2 pages); JP patent, No Publication Date.

Schultz, Von O.–E. et al., "Analogs of nuceic acid bases as antimetabolites," *Arzneimittel Forschung, Drug Res.*, 1967, 17(8), 1060–1064 (English summary included).

Schutkowski, M., et al., "Inhibition of peptidly–prolyl cis/trans isomerase activity by substrate analog structures: thioxo tetrapeptide–4–nitroanilides," *Biochemistry*, 1995, 34(40), 13016–13026.

Shroff, H.N., et al., "Small peptide inhibitors of $\alpha_4\beta_7$ mediated MadCAM–1 adhesion to lymphocytes," *Bioorg. Med. Chem. Letts.*, 1996, 6(21), 2495–2500.

Singh, G., et al., "Prodrug approach in new drug design and development," *J. Sci. Ind. Res.*, 1996, 55, 497–510.

Sonnenberg, A., "Integrins and their ligands," *Curr. Topics Microbiol. Immunol.*, 1993, 184, 7–35.

Springer, T.A., "Adhesion receptors of the immune system," *Nature*, 1990, 346, 425–434.

Springer, T.A., "Traffic Signals for Lymphocyte Recirculation and Leukocyte Emigration: The Multistep Paradigm," *Cell*, 1994, 76, 301–314.

Srivatsa, S.S., et al., "Selective αvβ3 integrin blockade potently limits neointimal hyperplasia and lumen stenosis following deep coronary arterial stent injury: evidence for the functional importance of integrin αvβ3 and osteopontin expression during neointima formation," *Cardiovascular Research*, 1997, 36, 408–428.

Stupack, D.G., et al., "induction of $\alpha_v\beta_3$ integrin–mediated attachment to extracellular matrix in $\beta_1$ interin (CD29)–negative B cell lines," *Experi. Cell Research*, 1992, 203, 443–448.

Tan R., et al., "Synthesis of 2, 6–naphthyridine and some of its derivatives," *Tetrahedron Letters*, 1965, 31, 2737–2744.

Tous, G., et al., "O'–(Epoxyalkyl) tyrosines and (Epoxyalkyl) phenylalanine as irreversible inactivators of serine proteases: synthesis and inhibition mechanism," *J. of Medicinal Chemistry*, 1990, 33(6), 1620–1634.

Tsunematsu, H. et al., "Hydrolysis of phenylthiazolones of p–guanidinophenylalanine and arginine by trypsin and related enzymes," *J. Biochem.*, 1983, 94(4), 1119–1125.

Ukai, Y. et al., "A novel synthetic inhibitor of endopeptidase–24.15," *Chemical Abstracts*, 1997, 127(2), 1 page; J. Enzym Inhib., 1996, 11(1), 39–49, reported in CAS.

Vanderslice, P. et al., "A Cyclic Hexapeptide is a Potent Antagonist of α4 Integrins," *J. Immunol.*, 1997, 158, 1710–1718.

Venturella, V.S. et al., "Substituted 1,3–Dihydro–4H–fur[3,4–d]–1,3–benzodiazepin–3–ones: Synthesis and Scope of the Method," *J. Heterocyclic Chem.*, 1969, 6(5), 671–679.

Yanagisawa, H. et al. WO 97/37970, "Preparation of phenylalkylcarboxylic acid derivatives lowering blood sugar level," *Chemical Abstracts*, 1997, Abstract 127:307307, 4 pages.

Yang, X., "A predominant role of integrin α4 in the spontaneous development of autoimmune diabetes in nonobese diabetic mice," *Proc. Natl. Acad. Sci. USA*, 1994, 91, 12604–12608.

Yednock, T.A., "Prevention of experimental autoimmune encephalomyelitis by antibodies against α4β1 integrin," *Nature*, 356, 63–66.

Whitlock, B.J. et al., "Structure and synthesis of lathyrine," *J. Org. Chem.*, 1965, 30, 115–118.

Wojciechowska, H. et al., "Preparation of 2,4–dinitrophenyl derivatives of tyrosine," *Chemical Abstracts*, 1968, 68(25), Abstract No. 114926r, 1 page; *Roc. Chem.*, 1967, 41(9), 1621–1623; reported in CAS.

WPI / Derwent No. XP–002076854, Japanese Patent No. JP 04 193 895 A (Ajinomoto, K.K.), Jul. 13, 1992, DW9234, 1 page, Abstract Only.

WPI/Derwent No. XP–002076855, Japanese Patent No. JP 56 049 373 A (Dainippon Pharm Co. Ltd.), May 2, 1981, DW8125, 1 page, Abstract only.

Hammadi, A., et al., "Diastereoselective hydrogenation of monodehydro enkephalins controlled by chiral rhodium catalysts," *Tetrahedron: Asymmetry*, 1992, 3(10), XP002106601, 1247–1262.

Nunami, K., et al., "A novel synthesis of methyl 1,5–disubstituted imidazole–4–carboxylates using 3–bromo–2–isocyanoacrylates," *J. Org. Chem.*, 1994, 59, XP002106602, 7635–7642.

Shimohigashi, Y., et al., "Dehydro–enkephalins," *Int. J. Peptide Protein Res.*, 1983, 21, XP002106600, 202–208.

Strange, P.G., et al., "Studies of enzyme–mediated reactions. Part II. Stereochemistry of the elimination of ammonia form L–tyrosine catalysed by the enzyme from maize," *J. Chem. Soc., Perkin I*, 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Rico, J.G., et al., "A highly steroselective michael addition to an αβ–unsaturated ester as the crucial step in the synthesis of a novel β–amino acid–containing fibrinogen receptor antagonist," *J. Org. Chem.*, 1993, 58, 7948–7951.

Zablocki, J.A., "Potent in vitro and in vivo inhibitors of platelet aggregation based upon the arg–gly–asp sequence of fibrinogen. (Aminobenzamidino)succinyl (ABAS) series of orally active fibrinogen receptor antagonists," *J. Med. Chem.*, 1995, 38, 2378–2394.

Bordner, J., et al., "1,3–diamino–6,7–dimethoxyisoquinoline derivatives as potential $\alpha_1$–adrenoceptor antagonists," *J. Med. Chem.*, 1988, 31, 1036–1039.

Brun, E.M., et al., "dienediolates of $\alpha,\beta$–unsaturated carboxylic acids in synthesis: a new synthetic method to 2–pyridones," *Synlett*, 1999, 7, 1088–1090.

Deady, L.W., et al., "Ethoxycarbonylation of α–cyano–o–t-oluonitrile and cyclization to isoquinolines and pyrimido [4,5–c]isoquinolines," *Aust. J. Chem.*, 1989, 42, 1029–1034.

Falk, H., et al., "On the chemistry of pyrrole pigments, XCI[1]: Copper complexes of pyridinologous linear tri–and tetra–pyrroles as cyclopropanation catalysts," *Monozshefte fur Chemie*, 1994, 125, 325–333.

Fieser and Fieser reagents for Organic Synthesis, *John Wiley and Sons*, 1999, vol. 1–19.

Green, T.W., in "Protective Groups in Organic Synthesis," *John Wiley and Sons*, 1999.

Hiebl, J., et al., "New synthesis of isoquinoline–3–carboxylates," *Tetra. Letts.*, 1999, 40, 7935–7938.

Katritzky, et al. (Eds.), Comprehensive Organic Functional Group Transformations, 1994, vol. 1–11.

Katritzky, A.R., et al. (Eds.), Comprehensive Organic Functional Group Transformations, Pergamon, 1995, vol. 1–7.

Katritzky, A.R., et al. (Eds.), Comprehensive Heterocyclic Chemistry, 1984, vol. 1–8.

Larock's Comprehensive Organic Transformations, *VCH Publishers, Inc.*, 1989.

March's Advanced Organic Chemistry, *John Wiley and Sons*, 1992.

Molina, P., et al., "Preparation and thermal ring–closure of β–aryl vinyl carbodi–imides: synthesis of isoquinoline derivatives," *J. Chem. Soc. Perkin Trans.*, 1990, 1, 1727–1731.

Paquette (Ed.), Encyclopedia of Reagents for Organic Synthesis, *John Wiley and Sons (eds.)*, 1995, vol. 1–8.

Rodd's Chemistry of Carbon Compounds and Supplementals, *Eslevier Sci. Pub.*, 1989, vol. 1–15.

Trost, et al. (Eds.), Comperhensive Organic Synthesis, *Pergamon*, 1991, vol. 1–9.

Wu, M., et al., "A direct anionic cyclization of 2–alkynyl-benzonitrile to 3–substituted–1(2H)–isoquinolones and 3–benzylideneisoindol–2–ones initiated by methoxide addition," *Tetrahedron*, 1999, 55, 13193–13200.

3-SUBSTITUTED ISOQUINOLIN-1-YL DERIVATIVES

This invention relates to a series of 3-substituted isoquinolin-1-yl derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A., Nature, 346, 425, (1990); Springer, T. A., Cell, 76, 301, (1994)]. Specific cell surface molecules collectively referred to as cell adhesion molecules mediate many of these interactions.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 16 different integrin alpha chains and 8 different integrin beta chains have been identified [Newman, P. et al, Molecular Medicine Today, 304, (1996)]. The members of the family are typically named according to their heterodimer composition although trivial nomenclature is widespread in the field. Thus the integrin $\alpha 4\beta 1$ consists of the integrin alpha 4 chain associated with the integrin beta 1 chain, but is also widely referred to as Very Late Antigen 4 or VLA-4. Not all of the potential pairings of integrin alpha and beta chains have yet been observed in nature and the integrin family has been subdivided into a number of subgroups based on the pairings that have been recognised to date [Sonnenberg, A., Current Topics in Microbiology and Immunology, 184, 7, (1993)].

The importance of integrin function in normal physiological responses is highlighted by two human deficiency diseases in which integrin function is defective. Thus in the disease termed Leukocyte Adhesion Deficiency (LAD) there is a defect in one of the families of integrins expressed on leukocytes [Marlin, S. D. et al, J. Exp. Med. 164, 855, (1985)]. Patients suffering from this disease have a reduced ability to recruit leukocytes to inflammatory sites and suffer recurrent infections, which in extreme cases may be fatal. In the case of patients suffering from the disease termed Glanzman's thrombasthenia (a defect in a member of the beta 3 integrin family) there is a defect in blood clotting (Hodivala-Dilke. K. M., J. Clin. Invest. 103, 229, (1999)].

The potential to modify integrin function in such a way as to beneficially modulate cell adhesion has been extensively investigated in animal models using specific antibodies and peptides that block various functions of these molecules [e.g. Issekutz, T. B., J. Immunol. 149, 3394. (1992); Li, Z. et al, Am. J. Physiol. 263, L723, (1992); Mitjans, F. et al, J. Cell Sci. 108, 2825, (1995); Brooks, P. C. et al, J. Clin. Invest. 96, 1815; (1995); Binns, R. M. et al, J. Immunol. 157, 4094, (1996); Hammes, H.-P. et al, Nature Medicine 2, 529, (1996); Srivata, S. et al, Cardiovascular Res. 36, 408 (1997)]. A number of monoclonal antibodies which block integrin function are currently being investigated for their therapeutic potential in human disease, and one, ReoPro, a chimeric antibody against the platelet integrin $\alpha IIb\beta 3$ is in use as a potent anti-thrombotic agent for use in patients with cardiovascular complications following coronary angioplasty.

Integrins recognize both cell surface and extracellular matrix ligands, and ligand specificity is determined by the particular alpha-beta subunit combination of the molecule [Newman, P. ibid]. One particular integrin subgroup of interest involves the $\alpha 4$ chain which can pair with two different beta chains $\beta 1$ and $\beta 7$ [Sonnenberg, A., ibid]. The $\alpha 4\beta 1$ pairing occurs on many circulating leukocytes (for example lymphocytes, monocytes, eosinophils and basophils) although it is absent or only present at low levels on circulating neutrophils. $\alpha 4\beta 1$ binds to an adhesion molecule (Vascular Cell Adhesion Molecule-1 also known as VCAM-1) frequently up-regulated on endothelial cells at sites of inflammation [Osborne. L., Cell, 62, 3, (1990)]. The molecule has also been shown to bind to at least three sites in the matrix molecule fibronectin [Humphries, M. J. et al, Ciba Foundation Symposium, 189, 177, (1995)]. Based on data obtained with monoclonal antibodies in animal models it is believed that the interaction between $\alpha 4\beta 1$ and ligands on other cells and the extracellular matrix plays an important role in leukocyte migration and activation [Yednock, T. A. et al, Nature, 356, 63, (1992); Podolsky, D. K. et al, J Clin. Invest. 92, 372, (1993); Abraham, W. M. et al, J. Clin. Invest. 93, 776, (1994)].

The integrin generated by the pairing of $\alpha 4$ and $\beta 7$ has been termed LPAM-1 [Holzmann, B. and Weissman, I. L., EMBO J. 8, 1735, (1989)]. The $\alpha 4\beta 7$ pairing is expressed on certain sub-populations of T and B lymphocytes and on eosinophils [Erle, D. J. et al, J. Immunol. 153, 517 (1994)]. Like $\alpha 4\beta 1$, $\alpha 4\beta 7$ binds to VCAM-1 and fibronectin. In addition, $\alpha 4\beta 7$ binds to an adhesion molecule believed to be involved in the homing of leukocytes to mucosal tissue termed MAdCAM-1 [Berlin, C. et al, Cell, 74, 185, (1993)]. The interaction between $\alpha 4\beta 7$ and MAdCAM-1 may also be important sites of inflammation outside of mucosal tissue [Yang, X.-D. et al, PNAS, 91, 12604, (1994)].

Regions of the peptide sequence recognizeded by $\alpha 4\beta 1$ and $\alpha 4\beta 7$ when they bind to their ligands have been identified. $\alpha 4\beta 1$ seems to recognise LDV, IDA or REDV peptide sequences in fibronectin and a QIDSP sequence in VCAM-1 [Humphries, M. J. et al, ibid] whilst $\alpha 4\beta 7$ recognises a LDT sequence in MAdCAM-1 [Birskin, M. J. et al, J. Immunol. 156, 719, (1996)]. There have been several reports of inhibitors of these interactions being designed from modifications of these short peptide sequences [Cardarelli, P. M. et al, J. Biol. Chem., 269, 18668, (1994); Shorff, H. N. et al, Biorganic Med. Chem. Lett. 6, 2495, (1996); Vanderslice, P. et al, J. Immunol., 158, 1710, (1997)]. It has also been reported that a short peptide sequence derived from the $\alpha 4\beta 1$ binding site in fibronectin can inhibit a contact hypersensitivity reaction in a trinitrochlorobenzene sensitised mouse [Ferguson, T. A., et al, PNAS, 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is important to be able to identify selective inhibitors of the alpha 4 subgroup.

We have now found a group of 3-substituted isoquinlin-1-yl derivatives which are potent and selective inhibitors of $\alpha 4$-integrins. Members of the group are able to inhibit $\alpha 4$ integrins such as $\alpha 4\beta 1$ and $\alpha 4\beta 7$ at concentrations at which they generally have no or minimal inhibitory action on $\alpha$ integrins of other subgroups. The 3-substituted isoquinlin-1-yl derivatives show unexpectedly high inhibition of $\alpha 4$-integrins when compared to unsubstituted isoquinolin-1-yl derivatives. The compounds are thus of use in medicine, for example in the prophylaxis and treatment of immune or inflammatory disorders as described hereinafter.

Thus according to one aspect of the invention we provide a compound of formula (1):

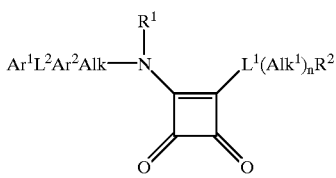

wherein

Ar$^1$ is a 3-substituted isoquinolin-1-yl group;

L$^2$ is a covalent bond or a linker atom or group;

Ar$^2$ is an optionally substituted aromatic or heteroaromatic chain;

Alk is a chain

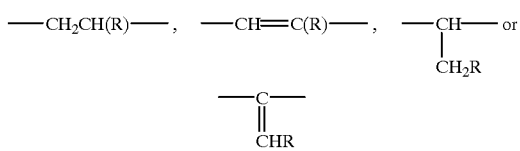

in which

R is a carboxylic acid (—CO$_2$H) or a derivative or biostere thereof;

R$^1$ is a hydrogen atom or a C$_{1-6}$alkyl group;

L$^1$ is a covalent bond or a linker atom or group;

Alk$^1$ is an optionally substituted aliphatic chain;

n is zero or the integer 1;

R$^2$ is a hydrogen atom or an optionally substituted heteroaliphatic, cycloaliphatic, heterocycloaliphatic, polycycloalphatic, heteropolycycloaliphatic, aromatic or heteroaromatic group;

and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise. In addition, compounds of formula (1) may exist as tautomers, for example keto (CH$_2$C=O)-enol (CH=CHOH) tautomers. Formula (1) and the formulae hereinafter are intended to represent all individual tautomers and mixtures thereof, unless stated otherwise.

The isoquinolin-1-yl group represented by Ar$^1$ is substituted at the 3-position of the isoquinoline ring by a substituent selected for example from an atom or group —L$^3$(Alk$^2$)$_t$L$^4$(R$^4$)$_u$ in which L$^3$ and L$^4$, which may be the same or different, is each a covalent bond or a linker atom or group, t is zero or the integer 1, u is an integer 1, 2 or 3, Alk$^2$ is an aliphatic or heteroaliphatic chain and R$^4$ is a hydrogen or halogen atom or a group selected from optionally substituted C$_{1-6}$alkyl or C$_{3-8}$ cycloalkyl, —OR$^5$ [where R$^5$ is a hydrogen atom, an optionally substituted C$_{1-6}$alkyl or C$_{3-8}$ cycloalkyl group], —SR$^5$, —NR$^5$R$^6$ [where R$^6$ is as just defined for R$^5$ and may be the same or different], —NO$_2$, —CN, —CO$_2$R$^5$, —SO$_3$H, —SOR$^5$, —SO$_2$R$^5$, —SO$_3$R$^5$, —OCO$_2$R$^5$, —CONR$^5$R$^6$, —OCONR$^5$R$^6$, —CSNR$^5$R$^6$, —COR$^5$, —OCOR$^5$, —N(R$^5$)COR$^6$, —N(R$^5$)CSR$^6$, —SO$_2$N(R$^5$)(R$^6$), —N(R$^5$)SO$_2$R$^6$, N(R$^5$)CON(R$^6$)(R$^7$) [where R$^7$ is a hydrogen atom, an optionally substituted C$_{1-6}$alkyl or C$_{3-8}$cycloalkyl group], —N(R$^5$)CSN(R$^6$)(R$^7$) or —N(R$^5$)SO$_2$N(R$^6$)(R$^7$), provided that when t is zero and each of L$^3$ and L$^4$ is a covalent bond then u is the integer 1 and R$^4$ is other than a hydrogen atom.

When L$^3$ and/or L$^4$ is present in these substituents as a linker atom or group it may be any divalent linking atom or group. Particular examples include —O— or —S— atoms or —C(O)—, —C(O)O—, —OC(O)—, —C(S)—, —S(O)—, —S(O)$_2$—, —N(R$^8$)— [where R$^8$ is a hydrogen atom or an optionally substituted C$_{1-6}$alkyl group], —N(R$^8$)O—, —N(R$^8$)N—, —CON(R$^8$)—, —OC(O)N(R$^8$)—, —CSN(R$^8$)—, —N(R$^8$)CO—, —N(R$^8$)C(O)O—, —N(R$^8$)CS—, —S(O)$_2$N(R$^8$)—, —N(R$^8$)S(O)$_2$—, —N(R$^8$)CON(R$^8$)—, —N(R$^8$)CSN(R$^8$)—, or —N(R$^8$)SO$_2$N(R$^8$)— groups. Where the linker group contains two R$^8$ substituents, these may be the same or different.

When R$^4$, R$^5$, R$^6$, R$^7$ and/or R$^8$ is present as a C$_{1-6}$alkyl group it may be a straight or branched C$_{1-6}$alkyl group, e.g. a C$_{1-3}$alkyl group such as a methyl or ethyl group. C$_{3-8}$cycloalkyl groups represented by R$^4$, R$^5$, R$^6$, R$^7$ and/or R$^8$ include C$_{3-6}$cycloalkyl groups e.g. cyclopropyl, cyclobutyl, cyclopentyl and cyclohexyl groups. Optional substituents which may be present on such groups include for example one, two or three substituents which may be the same or different selected from halogen atoms, for example fluorine, chlorine. bromine or iodine atoms, or hydroxy or C$_{1-6}$alkoxy e.g. methoxy or ethoxy groups.

When the groups R$^5$ and R$^6$ or R$^6$ and R$^7$ are both C$_{1-6}$alkyl groups these groups may be joined, together with the N atom to which they are attached, to form a heterocyclic ring. Such heterocyclic rings may be optionally interrupted by a further heteroatom selected from —O—, —S— or —N(R$^5$)—. Particular examples of such heterocyclic rings include piperidinyl, morpholinyl, thiomorpholinyl, pyrrolidinyl, imidazolidinyl and piperazinyl rings.

When Alk$^2$ is present as an aliphatic or heteroaliphatic chain it may be for example any divalent chain corresponding to the below-mentioned aliphatic chains described for Alk$^1$ or heteroaliphatic groups described for R$^2$ in which one of the terminal hydrogen atoms is replaced by a bond.

Halogen atoms represented by R$^4$ in the optional Ar$^1$ substituents include fluorine, chlorine, bromine, or iodine atoms.

Examples of the substituent represented by —L$^3$(Alk$^2$)$_t$L$^4$(R$^4$)$_u$ which is present at the 3-position of the isoquinoline ring represented by Ar$^1$ in compounds of the invention include atoms or groups —L$^3$Alk$^2$L$^4$R$^4$, —L$^3$Alk$^2$R$^4$, —L$^3$R$^4$, —R$^4$ and —Alk$^2$R$^4$ wherein L$^3$, Alk$^2$, L$^4$ and R$^4$ are as defined above. Particular examples of such substituents include —L$^3$CH$_2$L$^4$R$^4$, —L$^3$CH(CH$_3$)L$^4$R$^4$, —L$^3$CH(CH$_2$)$_2$L$^4$R$^4$, —L$^3$CH$_2$R$^4$, —L$^3$CH(CH$_3$)R$^4$, —L$^3$(CH$_2$)$_2$R$^4$, —CH$_2$R$^4$, —CH(CH$_3$)R$^4$, —(CH$_2$)$_2$R$^4$ and —R$^4$ groups.

Thus the isoquinolin-1-yl group in compounds of the invention may be optionally substituted at the 3-position for example by one, two, three or more halogen atoms, e.g. fluorine, chlorine, bromine or iodine atoms, or C$_{1-6}$alkyl, e.g. methyl, ethyl, n-propyl, i-propyl, n-butyl or t-butyl, C$_{3-8}$cycloalkyl, e.g. cyclopropyl, cyclobutyl, cyclopentyl or cyclohexyl, C$_{1-6}$hydroxyalkyl, e.g. hydroxymethyl, hydroxyethyl or —C(OH)(CF$_3$)$_2$, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxypropylthio, C$_{1-6}$alkoxy, e.g. methoxy or ethoxy, hydroxyC$_{1-6}$alkoxy, e.g.

2-hydroxyethoxy, halo$C_{1-6}$alkyl, e.g. —$CF_3$, —$CHF_2$, $CH_2F$, halo$C_{1-6}$alkoxy, e.g. —$OCF_3$, —$OCHF_2$ —$OCH_2F$, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino $C_{1-6}$alkoxy, e.g. methylaminoethoxy, $C_{1-6}$dialkylamino $C_{1-6}$alkoxy, e.g. dimethylaminoethoxy, diethylaminoethoxy, isopropylaminoethoxy, or dimethylaminopropoxy, nitro, cyano, amidino, hydroxyl (—OH), formyl [HC(O)—], carboxyl (—$CO_2H$), —$CO_2Alk^3$ [where $Alk^3$ is as defined below for $Alk^7$], $C_{1-6}$ alkanoyl e.g. acetyl, thiol (—SH), thio$C_{1-6}$alkyl, e.g. thiomethyl or thioethyl, sulphonyl (—$SO_3H$), —$SO_3Alk^3$, $C_{1-6}$alkylsulphinyl, e.g. methylsulphinyl, $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino $C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$ alkanoylamino, e.g. acetylamino, amino$C_{1-6}$alkanoylamino e.g. aminoacetylamino, $C_{1-6}$dialkylamino $C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino groups.

The 4, 5, 6, 7 and 8-positions of the isoquinolin-1-yl group represented by $Ar^1$ may additionally each be substituted by an optional substituent ($R^{17}$) selected from halogen atoms, e.g. fluorine, chlorine, bromine or iodine atoms, or $C_{1-6}$alkyl e.g. methyl or ethyl, $C^{3-8}$cycloalkyl e.g. cyclopropyl, cyclobutyl, cyclopentyl or cyclohexyl, halo$C_{1-6}$alkyl e.g. halomethyl or haloethyl such as difluoromethyl or trifluoromethyl, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, $C_{1-6}$alkylthio, e.g. methylthio or ethylthio, —OH, —$N(R^3)_2$ (in which $R^3$ is an atom or group as defined herein for $R^8$), —CN, —$CO_2R^3$, —$NO_2$, —$CON(R^3)_2$, —$CSN(R^3)_2$, —$COR^3$, —$CON(R^3)_2$, —$N(R^3)COR^3$, —$N(R^3)CSR^3$, —$SO_2N(R^3)_2$, —$N(R^3)SO_2R^3$, —$N(R^3)CON(R^3)_2$, —$N(R^3)CON(R^3)2$ or —$N(R)^3SO_2N(R^3)_2$ group. Where two $R^3$ atoms or groups are present in these substituents these may be the same or different.

Where desired, two $R^{17}$ substituents may be linked together to form a cyclic group such as a cyclic ether e.g. a $C_{1-6}$alkylenedioxy group such as methylenedioxy or ethylenedioxy.

$L^2$ when present in compounds of the invention may be a linker atom or group $L^{2a}$ or a linker —$Alk^a(L^{2a})_y$—, where $Alk^a$ is an optionally substituted aliphatic or heteroaliphatic chain as previously defined for $Alk^2$, $L^{2a}$ is a covalent bond or a linker atom or group as described above for $L^3$ and $L^4$, and y is zero or the integer 1.

Optionally substituted aromatic or heteroaromatic groups represented by $Ar^2$ include those aromatic or heteroaromatic groups described hereinafter in relation to $R^2$ aromatic or heteroaromatic groups respectively where said groups become divalent linking groups, for example phenylene. pyridinylene or pyrimidinylene groups. The optional substituents which may be present on these groups include one, two, three or four optional substituents ($R^{17a}$, $R^{17b}$, $R^{17c}$ and $R^{17d}$) where such substituents include those $R^{17}$ optional substituents described hereinbefore.

When the group R is present in compounds of the invention as a derivative of a carboxylic acid it may be for example a carboxylic acid ester or amide. Particular esters and amides include —$CO_2Alk^7$ and —$CONR^5R^6$ groups as defined herein. When R is a biostere of a carboxylic acid it may be for example a tetrazole or other acid such as phosphonic acid, phosphinic acid, sulphonic acid, sulphinic acid or boronic acid or an acylsulphonamide group.

Esters (—$CO_2Alk^7$) and amide (—$CONR^5R^6$) derivatives of the carboxylic acid group (—$CO_2H$) in compounds of formula (1) may advantageously be used as prodrugs of the active compound. Such prodrugs are compounds which undergo biotransformation prior to exhibiting their pharmacological effects and the invention particularly extends to prodrugs of the acids of formula (1). Such prodrugs are well known in the art, see for example International Patent Application No. WO00/23419, Bodor, N. (Alfred Benzon Symposium, 1982, 17, 156–177), Singh, G. et al (J. Sci. Ind. Res., 1996, 55, 497–510) and Bundgaard, H., (Design of Prodrugs, 1985, Elsevier, Amsterdam.

Esterified carboxyl groups represented by the group $R^{13a}$ include groups of formula —$CO_2Alk^7$ wherein $Alk^7$ is a straight or branched optionally substituted $C_{1-8}$alkyl group such as a methyl, ethyl, n-propyl, i-propyl, n-butyl, i-butyl, s-butyl or t-butyl group; an optionally substituted $C_{2-8}$alkenyl group such as a propenyl e.g. 2-propenyl or butenyl e.g. 2-butenyl or 3-butenyl group, an optionally substituted $C_{2-8}$alkynyl group such as a ethynyl, propynyl e.g. 2-propynyl or butynyl e.g. 2-butynyl or 3-butynyl group, an optionally substituted $C_{3-8}$cycloalkyl group such as a cyclopropyl, cyclobutyl, cyclopentyl, cyclohexyl or cycloheptyl group; an optionally substituted $C_{3-8}$cycloalkyl$C_{1-8}$alkyl group such as a cyclopentylmethyl, cyclohexylmethyl or cyclohexylethyl group; an optionally substituted $C_{3-8}$heterocycloalkyl$C_{1-6}$alkyl group such as a morpholinyl-N-ethyl, thiomorpholinyl-N-methyl, pyrrolidinyl-N-ethyl, pyrrolidinyl-N-propyl, piperidinyl-N-ethyl, pyrazolidinyl-N-methyl or piperazinyl-N-ethyl group; an optionally substituted $C_{1-6}$alkyloxy$C_{1-6}$alkyl group such as a methyloxyethyl or propyloxyethyl group; an optionally substituted $C_{1-6}$alkylthio$C_{1-6}$alkyl group such as an ethylthioethyl group; an optionally substituted $C_{1-6}$alkylsulfinyl$C_{1-6}$alkyl group such as an methylsulfinylethyl group; an optionally substituted $C_{1-6}$alkylsulfonyl$C_{1-6}$alkyl group such as an methylsulfonylmethyl group; an optionally substituted $C_{3-8}$cycloalkyloxy$C_{1-6}$alkyl group such as a cyclohexyloxymethyl group; an optionally substituted $C_{3-8}$cycloalkylthioC1-6alkyl group such as a cyclopentylthiomethyl group; an optionally substituted $C_{3-8}$cycloalkylsulfinyl$C_{1-6}$alkyl group such as a cyclopentylsulfinylmethyl group; an optionally substituted $C_{3-8}$cycloalkylsulfonyl$C_{1-6}$alkyl group such as a cyclopentylsulfonylmethyl group; an optionally substituted $C_{1-6}$alkyloxycarbonyl$C_{1-6}$alkyl group such as isobutoxycarbonylpropyl group; an optionally substituted $C_{1-6}$alkyloxycarbonyl$C_{1-6}$alkenyl group such as isobutoxycarbonypentenyl group. an optionally substituted $C_{1-6}$alkyloxycarbonyloxy$C_{1-6}$alkyl group such as an isopropoxycarbonyloxyethyl e.g a 1-(isopropoxycarbonyloxy)ethyl, 2-(isopropoxycarbonyloxy)ethyl or ethyloxycarbonyloxymethyl group; an optionally substituted $C_{1-6}$alkyloxy carbonyloxy$C_{1-6}$alkenyl group such as a isopropoxycarbonyloxybutenyl group, an optionally substituted $C_{3-8}$cycloalkyloxycarbonyloxy$C_{1-6}$alkyl group such as a cyclohexyloxycarbonyloxyethyl, e.g. a 2-(cyclohexyloxycarbonyloxy)ethyl group, an optionally substituted N-di-$C_{1-8}$alkylamino$C_{1-8}$alkyl group such as a N-dimethylaminoethyl or N-diethylaminoethyl group; an optionally substituted N—$C_{612}$aryl-N—$C_{1-6}$alkylamino$C_{1-6}$alkyl group such as a N-phenyl-N-methylaminomethyl group an optionally substituted N-di-$C_{1-8}$alkylcarbamoyl$C_{1-8}$alkyl group such as a N-diethylcarbamoyl-methyl group; an optionally substituted $C_{6-10}$aryl$C_{1-6}$alkyl group such as an optionally substituted benzyl, phenylethyl, phenylpropyl, 1-naphthylmethyl or 2-naphthylmethyl group; a $C_{6-10}$aryl group such as an optionally substituted phenyl, 1-naphthyl or 2-naphthyl group; a $C_{6-10}$aryloxy$C_{1-8}$alkyl group such as an optionally substituted phenyloxymethyl, phenyloxyethyl, 1-naphthyloxymethyl, or 2-naphthyloxymethyl group; a $C_{6-12}$arylthio$C_{1-8}$alkyl group such as an optionally substituted phenylthioethyl group; a $C_{6-12}$arylsulfinyl$C_{1-8}$alkyl group such as an optionally substituted phenylsulfinylmethyl group; a $C_{6-12}$arylsulfonyl$C_{1-8}$alkyl group such as an optionally substituted phenylsulfonylmethyl group; an optionally substituted $C_{1-8}$alkanoyloxy$C_{1-8}$alkyl group, such as a acetoxymethyl, ethoxycarbonyloxyethyl, pivaloyloxymethyl, propionyloxyethyl or propionyloxypropyl group; an optionally substituted $C_{4-8}$imido$C_{1-8}$alkyl group such as a succinimidomethyl or phthalamidoethyl group; a $C_{6-12}$aroyloxy$C_{1-8}$alkyl group such as an optionally substituted benzoyloxyethyl or benzoyloxypropyl group or a triglyceride such as a 2-substituted triglyceride e.g. a 1,3-di-$C_{1-8}$alkylglycerol-2-yl group such as a 1,3-diheptylglycerol-2-yl group. Optional substituents present on the Alk$^7$ group include $R^{13a}$ substituents described above.

It will be appreciated that in the forgoing list of Alk$^7$ groups the point of attachment to the remainder of the compound of formula (1) is via the last described part of the Alk$^7$ group. Thus, for example a methoxyethyl group would be attached by the ethyl group, whilst a morpholinyl-N-ethyl group would be attached via the N-ethyl group.

It will be further appreciated that in the forgoing list of Alk$^7$ groups, where not specifically mentioned, alkyl groups may be replaced by alkenyl or alkynyl groups where such groups are as previously defined for Alk$^1$. Additionally these alkyl, alkenyl or alkynyl groups may optionally be interrupted by one, two or three linker atoms or groups where such linker atoms and groups are as previously defined for $L^3$.

When the group $R^1$ is present in compounds of the invention as a $C_{1-6}$alkyl group it may be for example a straight or branched $C_{1-6}$alkyl group, e.g. a $C_{1-3}$alkyl group such as a methyl or ethyl group.

The linker atom or group represented by $L^1$ in compounds of formula (1) may be any linker atom or group as described above for the linker atom or group $L^3$.

When the group Alk$^1$ is present in compounds of formula (1) as an optionally substituted aliphatic chain it may be an optionally substituted $C_{1-10}$ aliphatic chain. Particular examples include optionally substituted straight or branched chain $C_{1-6}$ alkylene, $C_{2-6}$ alkenylene, or $C_{2-6}$ alkynylene chains.

Particular examples of aliphatic chains represented by Alk$^1$ include optionally substituted —$CH_2$—, —$(CH_2)_2$—, —$CH(CH_3)CH_2$—, —$(CH_2)_2CH_2$—, —$(CH_2)_3CH_2$—, —$CH(CH_3)(CH_2)_2$—, —$CH_2CH(CH_3)CH_2$—, —$C(CH_3)_2CH_2$, —$CH_2C(CH_3)_2CH_2$—, —$(CH_2)_2C(CH_3)_2CH_2$—, —$(CH_2)_4CH_2$—, —$(CH_2)_5CH_2$—, —CHCH—, —CHCHCH$_2$—, —$CH_2$CHCH—, —CHCHCH$_2$CH$_2$—, —$CH_2$CHCHCH$_2$—, —$(CH_2)_2$CHCH—, —CC—, —CCCH$_2$—, —$CH_2$CC—, —CCCH$_2$CH$_2$—, —$CH_2$CCCH$_2$— or —$(CH_2)_2$CCH— groups.

Heteroaliphatic groups represented by the group $R^2$ in the compounds of formula (1) include the aliphatic chains just described for Alk$^1$ but with each containing a terminal hydrogen atom and additionally containing one, two, three or four heteroatoms or heteroatom-containing groups. Particular heteroatoms or groups include atoms or groups $L^5$ where $L^5$ is as defined above for $L^3$ when $L^3$ is a linker atom or group. Each $L^5$ atom or group may interrupt the aliphatic group, or may be positioned at its terminal carbon atom to connect the group to an adjoining atom or group. Particular examples include optionally substituted —$L^5CH_3$, —$CH_2L^5CH_3$ —$L^5CH_2CH_3$, —$CH_2L^5CH_2CH_3$, —$(CH_2)_2L^5CH_3$, —$(CH_2)_3L^5CH_3$, —$L^5(CH_2)_3$, and —$(CH_2)_2L^5CH_2CH_3$ groups.

The optional substituents which may be present on aliphatic or heteroaliphatic chains represented by Alk$^1$ and $R^2$ respectively include one, two, three or more substituents where each substituent may be the same or different and is selected from halogen atoms, e.g. fluorine, chlorine, bromine or iodine atoms, or —OH, —$CO_2H$, —$CO_2R^9$, where $R^9$ is an optionally substituted straight or branched $C_{1-6}$alkyl group as defined above for $R^4$, —$CONHR^9$, —$CON(R^9)_2$, —$COCH_3$, $C_{1-6}$alkoxy, e.g. methoxy or ethoxy, thiol, —$S(O)R^9$, —$S(O)_2$ $R^9$, $C_{1-6}$alkylthio e.g. methylthio or ethylthio. amino or substituted amino groups. Substituted amino groups include —$NHR^9$ and —$N(R^9)_2$ groups. Where two $R^9$ groups are present in any of the above substituents these may be the same or different.

Optionally substituted cycloaliphatic groups represented by the group $R^2$ in compounds of the invention include optionally substituted $C_{3-10}$ cycloaliphatic groups. Particular examples include optionally substituted $C_{3-10}$ cycloalkyl, e.g. $C_{3-7}$ cycloalkyl or $C_{3-10}$ cycloalkenyl, e.g $C_{3-7}$ cycloalkenyl groups.

Optionally substituted heterocycloaliphatic groups represented by the group $R^2$ include optionally substituted $C_{3-10}$heterocycloaliphatic groups. Particular examples include optionally substituted $C_{3-10}$heterocycloalkyl, e.g. $C_{3-7}$ heterocycloalkyl, or $C_{3-10}$heterocycloalkenyl, e.g. $C_{3-7}$ hetercycloalkenyl groups, each of said groups containing one, two, three or four heteroatoms or heteroatom-containing groups $L^5$ as defined above.

Optionally substituted polycycloaliphatic groups represented by the group $R^2$ include optionally substitued $C_{7-10}$bi- or tricycloalkyl or $C_{3-7}$ bi- or tricycloalkenyl groups. Optionally substituted heteropolycycloaliphatic groups represented by the group $R^2$ include the optionally substituted polycycloalkyl groups just described, but with each group additionally containing one, two, three or four $L^5$ atoms or groups.

Particular examples of cycloaliphatic, polycycloaliphatic, heterocycloaliphatic and heteropolycycloaliphatic groups represented by the group $R^2$ include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, homopiperidinyl (azepanyl), heptamethyleneiminyl, piperidinone, 1,4-dioxanyl, morpholinyl, morpholinone, 1,4-dithianyl, thiomorpholinyl, piperazinyl, homopiperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the cycloaliphatic, polycycloaliphatic, heterocycloaliphatic or polyheterocycloaliphatic groups represented by the group $R^2$ include one, two, three or more substituents each selected from halogen atoms, e.g. fluorine, chlorine, bromine or iodine atoms, or $C_{1-6}$alkyl, e.g. methyl or ethyl, halo$C_{1-6}$alkyl, e.g. halomethyl or haloethyl such as difluoromethyl or trifluoromethyl, optionally substituted by hydroxyl, e.g. —C(OH)(CF$_3$)$_2$, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, $C_{1-6}$alkylthio e.g. methylthio or ethylthio, or —(Alk$^4$)$_v$R$^{10}$ groups in which Alk$^4$ is a straight or branched $C_{1-3}$alkylene chain, v is zero or an integer 1 and $R^{10}$ is a —OH, —SH, —N(R$^{11}$)$_2$, (in which $R^{11}$ is an atom or group as defined herein for $R^8$) —CN, —CO$_2$R$^{11}$, —NO$_2$, —CON(R$^{11}$)$_2$, —CSN(R$^{11}$)$_2$, —COR$^{11}$, —CSN(R$^{11}$)$_2$, —N(R$^{11}$)COR$^{11}$, —N(R$^{11}$)CSR$^{11}$, —SO$_2$N(R$^{11}$)$_2$, —N(R$^{11}$)SO$_2$R$^{11}$, —N(R$^{11}$)CON(R$^{11}$)$_2$, —N(R$^{11}$)CSN(R$^{11}$), N(R$^{11}$)SO$_2$N(R$^{11}$)$_2$ or optionally substituted phenyl group. Where two $R^{11}$ atoms or groups are present in these substituents these may be the same or different. Optionally substituted phenyl groups include phenyl substituted by one, two or three of the $R^{13}$ groups described below.

Particular examples of Alk$^4$ chains include —CH$_2$—, —CH$_2$CH$_2$—, —CH$_2$CH$_2$CH$_2$— and —CH(CH$_3$)CH$_2$— chains.

Additionally, when the group $R^2$ is a heterocycloaliphatic group containing one or more nitrogen atoms each nitrogen atom may be optionally substituted by a group —(L$^6$)$_p$(Alk$^5$)$_q$R$^{12}$ in which L$^6$ is —C(O)—, —C(O)O—, —C(S)—, —S(O)$_2$—, —CON(R$^{11}$)—, —CSN(R$^{11}$)— or SO$_2$N(R$^{11}$)—; p is zero or an integer 1: Alk$^5$ is an optionally substituted aliphatic or heteroaliphatic chain; q is zero or an integer 1; and $R^{12}$ is a hydrogen atom or an optionally substituted cycloaliphatic, heterocycloaliphatic, polycycloaliphatic, polyheterocycloaliphatic, aromatic or heteroaromatic group.

Optionally substituted aliphatic or heteroaliphatic chains represented by Alk$^5$ include those optionally substituted chains described above for Alk$^2$.

Cycloaliphatic, heterocycloaliphatic, polycycloaliphatic or polyheterocycloaliphatic groups represented by $R^{12}$ include those groups just described for the group $R^2$. Optional substituents which may be present on these groups include those described above in relation to Alk$^1$ and $R^2$ aliphatic and heteroaliphatic chains. Optionally substituted aomatic or heteroaromatic groups represented by $R^{12}$ include those optionally substituted $R^2$ aromatic and heteroaromatic groups as described hereinafter.

Optionally substituted aromatic groups represented by $R^2$ include for example optionally substituted monocyclic or bicyclic fused ring $C_{6-12}$ aromatic groups, such as phenyl, 1- or 2-naphthyl, 1- or 2-tetrahydronaphthyl, indanyl or indenyl groups.

Optionally substituted heteroaromatic groups represented by the group $R^2$ include for example optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—C$_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, [2,3-dihydro]benzothienyl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, quinoxalinyl, naphthyridinyl, pyrido[3,4-b]pyridyl, pyrido[3 2-b]pyridyl, pyrido[4,3-b]-pyridyl, quinolinyl, isoquinolinyl, tetrazolyl, 5,6,7,8-tetrahydroquinolinyl, 5,6,7,8-tetrahydroisoquinolinyl, and imidyl. e.g. succinimidyl phthalimidyl, or naphthalimidyl such as 1,8-naphthalimidyl.

Optional substituents which may be present on the aromatic or heteroaromatic groups represented by the group $R^2$ include one, two, three or more substituents, each selected from an atom or group $R^{13}$ in which $R^{13}$ is —$R^{13a}$ or —Alk$^6$(R$^{13a}$)$_m$, where $R^{13a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{14}$ [where $R^{14}$ is an —Alk$^6$(R$^{13a}$)$_m$, cycloaliphatic, heterocycloaliphatic, aryl or heteroaryl group], —CSR$^{14}$, —SO$_3$H, —SOR$^{14}$, —SO$_2$R$^{14}$, —SO$_3$R$^{14}$, —SO$_2$NH$_2$, —SO$_2$NHR$^{14}$ SO$_2$N(R$^{14}$)$_2$, —CONH$_2$, —CSNH$_2$, —CONHR$^{14}$, —CSNHR$^{14}$, —CON[R$^{14}$]$_2$, —CSN(R$^{14}$)$_2$, N(R$^{11}$)SO$_2$R$^{14}$, —N(SO$_2$R$^{14}$)$_2$, —NH(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$)COR$^{14}$, —N(R$^{11}$)CONH$_2$, —N(R$^{11}$)CONHR$^{14}$, —N(R$^{11}$)CON(R$^{14}$)$_2$, —N(R$^{11}$)CSNH$_2$, —N(R$^{11}$)CSNHR$^{14}$, —N(R$^{11}$)CSN(R$^{14}$)$_2$, —N(R$^{11}$)CSR$^{14}$, —N(R$^{11}$)C(O)OR$^{14}$, —SO$_2$NHet$^1$ [where —NHet$^1$ is an optionally substituted $C_{5-7}$cyclicamino group optionally containing one or more other —O— or —S— atoms or —N(R$^{11}$)—, —C(O)—, —C(S)—, S(O) or —S(O)$_2$ groups], —CONHet$^1$, —CSNHet$^1$, —N(R$^{11}$)SO$_2$NHet$^1$, —N(R$^{11}$)CONHet$^1$, —N(R$^{11}$)CSNHet$^1$, —SO$_2$ N(R$^{11}$)Het$^2$ [where Het$^2$ is an optionally substituted monocyclic $C_{5-7}$carbocyclic group optionally containing one or more —O— or —S—atoms or —N($R^{11}$)—, —C(O)— or —C(S)—groups], —$Het^2$, —CON($R^{11}$)$Het^2$, —CSN($R^{11}$)$Het^2$, —N($R^{11}$)CON($R^{11}$)$Het^2$, —N($R^{11}$)CSN($R^{11}$)$Het^2$, cycloaliphatic, heterocycloaliphatic, aryl or heteroaryl group; $Alk^6$ is a straight or branched $C_{1-6}$alkylene, $C_{2-6}$alkenylene or $C_{2-6}$alkynylene chain, optionally interrupted by one, two or three —O— or —S— atoms or —S(O)$_n$ [where n is an integer 1 or 2] or —N($R^{15}$)— groups [where $R^{15}$ is a hydrogen atom or $C_{1-6}$alkyl, e.g. methyl or ethyl group]; and m is zero or an integer 1, 2 or 3. It will be appreciated that when two $R^{11}$ or $R^{14}$ groups are present in one of the above substituents, the $R^{11}$ or $R^{14}$ groups may be the same or different.

When in the group —$Alk^6(R^{13a})_m$ m is an integer 1, 2 or 3, it is to be understood that the substituent or substituents $R^{13a}$ may be present on any suitable carbon atom in —$Alk^6$. Where more than one $R^{13a}$ substituent is present these may be the same or different and may be present on the same or different atom in —$Alk^6$. Clearly, when m is zero and no substituent $R^{13a}$ is present the alkylene, alkenylene or alkynylene chain represented by $Alk^6$ becomes an alkyl, alkenyl or alkynyl group.

When $R^{13a}$ is a substituted amino group it may be for example a group —$NHR^{14}$ [where $R^{14}$ is as defined above] or a group —N($R^{14}$)$_2$ wherein each $R^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group —$OR^{14}$ or a —$SR^{14}$ or —SC(=NH)$NH_2$ group respectively.

Esterified carboxyl groups represented by the group $R^{13a}$ include groups of formula —$CO_2Alk^7$ wherein $Alk^7$ is a group as defined hereinbefore.

When $Alk^6$ is present in or as a substituent it may be for example a methylene, ethylene, n-propylene, i-propylene, n-butylene, i-butylene, s-butylene, t-butylene, ethenylene, 2-propenylene, 2-butenylene, 3- butenylene, ethynylene, 2-propynylene, 2-butynylene or 3-butynylene chain, optionally interrupted by one, two, or three —O— or —S—, atoms or —S(O)—, —S(O)$_2$— or —N($R^9$)— groups.

Cycloaliphatic or heterocycloaliphatic groups represented by the groups $R^{13a}$ or $R^{14}$ include those optionally substituted $C_{3-10}$cycloaliphatic or $C_{3-10}$ heterocycloaliphatic groups described above for $R^2$.

Aryl or heteroaryl groups represented by the groups $R^{13a}$ or $R^{14}$ include mono- or bicyclic optionally substituted $C_{6-12}$ aromatic or $C_{1-9}$ heteroaromatic groups as described above for the group $R^2$. The aromatic and heteroaromatic groups may be attached to the remainder of the compound of formula (1) by any carbon or hetero e.g. nitrogen atom as appropriate.

When —$NHet^1$ or —$Het^2$ forms part of a substituent $R^{13}$ each may be for example an optionally substituted pyrrolidinyl, pyrazolidinyl, piperazinyl, morpholinyl, thiomorpholinyl, piperidinyl or thiazolidinyl group. Additionally $Het^2$ may represent for example, an optionally substituted cyclopentyl or cyclohexyl group. Optional substituents which may be present on —$NHet^1$ or —$Het^2$ include those optional substituents described above for $R^2$ heterocycloaliphatic groups.

Particularly useful atoms or groups represented by $R^{13}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, e.g. t-butyloxycarbonylpiperazinyl, pyrrolidinyl, dioxolanyl, dioxanyl, oxazolidinyl, thiazolidinyl, imidazolidinyl or piperidinyl, $C_{1-6}$hydroxyalkyl, e.g. hydroxymethyl or hydroxyethyl, carboxy$C_{1-6}$alkyl; e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{4-7}$cycloalkyl, e.g. cyclobutyl, cyclopentyl, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino, ethylamino or propylamino, C6–12arylC1–6alkylamino, e.g.benzylamino, 4-fluorobenzylamino or 4-hydroxyphenylethylamino, amino (—$NH_2$), amino$C_{1-6}$alkyl. e.g. aminomethyl or aminoethyl, $C_{1-6}$dialkylamino, e.g. dimethylamino or diethylamino, aminoC1–6alkylamino, e.g. aminoethylamino or aminopropylamino, optionally substituted $Het^1$NC$_{1-6}$alkylamino, e.g. 3-morpholinopropylamino, $C_{1-6}$akylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy. $C_{1-6}$alkylamino $C_{1-6}$alkoxy, e.g. methylaminoethoxy, $C_{1-6}$dialkylamino $C_{1-6}$alkoxy, e.g. dimethylaminoethoxy, diethylaminoethoxy, diisopropylaminoethoxy, or dimethylaminopropoxy, hydroxy$C_{1-6}$alkylamino, e.g. 2-hydroxyethylamino, 3-hydroxypropylamino or 3-hydroxybutylamino, imido, such as phthalimido or naphthalimido, e.g. 1,8-naphthalimido, nitro, cyano, amidino, hydroxyl (—OH), formyl [HC(O)—], carboxyl (—$CO_2H$), —$CO_2Alk^7$ [where $Alk^7$ is as defined above], $C_{1-6}$ alkanoyl e.g. acetyl, propyryl or butyryl, optionally substituted benzoyl, thiol (—SH), thio$C_{1-6}$alkyl, e.g. thiomethyl or thioethyl, —SC(=NH)$NH_2$, sulphonyl (—$SO_3H$), —$SO_3Alk^7$, $C_{1-6}$alkylsulphinyl, e.g. methylsulphinyl, ethylsulphinyl or propylsulphinyl, $C_{1-6}$alkylsulphonyl, e.g. methylsulphonyl, ethylsulphonyl or propylsulphonyl, aminosulphonyl (—$SO_2NH_2$), $C_{1-6}$alkylaminosulphonyl, e.g. methylaminosulphonyl, ethylaminosulphonyl or propylaminosulphonyl $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl, ethylaminocarbonyl or propylaminocarbonyl, $C_{1-6}$dialkylaminocarbonyl, e.g. dimethylaminocarbonyl or diethylaminocarbonyl, amino $C_{1-6}$alkylaminocarbonyl, e.g. aminoethylaminocarbonyl, $C_{1-6}$alkylamino$C_{1-6}$alkylaminocarbonyl, e.g. methylaminoethylaminocarbonyl, $C_{1-6}$dialkyl-amino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethyiaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)$NH_2$, $C_{1-6}$alkyl-sulphonylamino, e.g. methylsulphonylamino or ethylsulphonylamino, haloC$_{1-6}$alkylsulphonylamino, e.g. trifluoromethylsulphonylamino, C$_{1-6}$dialkylsulphonylamino, e.g. dimethylsulphonylamino or diethylsulphonylamino, optionally substituted phenylsulphonylaminc, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, optionally substituted morpholinesulphonylamino or morpholinesulphonylC$_{1-6}$alkylamino. optionally substituted phenylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoylamino, e.g. dimethylaminoacetylamino, C$_{1-6}$alkanoylamino C$_{1-6}$alkyl, e.g. acetylaminomethyl, C$_{1-6}$alkanoylamino C$_{1-6}$alkylamino, e.g. acetamidoethylamino, C$_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylaminoC$_{1-6}$alkyl e.g. benzyloxycarbonylaminoethyl, thiobenzyl, pyridylmethylthio or thiazolylmethylthio groups.

Where desired, two R$^{13}$ substituents may be linked together to form a cyclic group such as a cyclic ether, e.g. a C$_{1-6}$alkylenedioxy group such as methylenedioxy or ethylenedioxy.

It will be appreciated that where two or more R$^{13}$ substituents are present, these need not necessarily be the same atoms and/or groups. In general, the substituent(s) may be present at any available ring position in the aromatic or heteroaromatic group represented by R$^2$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates. e.g. p-toluenesulphonates besylates or napsylates, phosphates, sulphates, hydrogen sulphates, acetates, trifluoroacetates propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

The group Ar$^2$ in compounds of formula (1) is preferably an optionally substituted phenylene group.

A particularly useful group of compounds according to the invention has the formula (2):

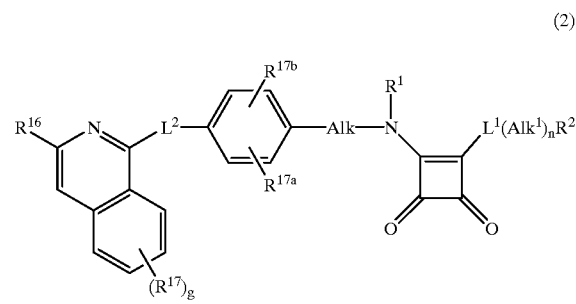

(2)

wherein

R$^{16}$ is an atom or group —L$^3$(Alk$^2$)$_t$L$^4$(R$^4$)$_u$ in which L$^3$, Alk$^2$, t, L$^4$, R$^4$, and u are as previously generally and particularly defined;

R$^{17a}$ and R$^{17b}$ is each a hydrogen atom or an optional substituent as previously defined for R$^{17}$;

R$^{17}$, L$^1$, L$^2$, Ar$^2$, Alk, R$^1$, Alk, n and R$^2$ are as defined for formula (1);

g is zero or the integer 1, 2, 3, 4 or 5;

and the salts, solvates, hydrates and N-oxides thereof.

Particularly useful R$^{16}$ substituents when present in compounds of formula (2) include halogen atoms. especially fluorine or chlorine atoms, or straight or branched C$_{1-6}$alkyl, especially methyl, ethyl or isopropyl, C$_{3-8}$cycloalkyl especially cyclopropyl, haloC$_{1-6}$alkyl, especially halomethyl, most especially —CF$_3$ or —CHF$_2$, straight of branched C$_{1-6}$alkoxy, especially methoxy or ethoxy, haloC$_{1-6}$alkoxy, especially halomethoxy, most especially —OCF$_3$ or —OCHF$_2$, —SR$^5$ especially methylthio or ethylthio, —CN, —CO$_2$Alk$^3$, especially —CO$_2$CH$_3$, —NO$_2$, amino (—NH$_2$), substituted amino (—NR$^5$R$^6$), —N(R$^5$)COR$^6$, especially —NHCOCH$_3$ and —COR$^5$, especially —COCH$_3$ groups.

Most especially useful R$^{16}$ substituents when present in compounds of formula (2) include halogen atoms, especially fluorine and chlorine atoms and straight or branched C$_{1-6}$alkyl groups, especially methyl, ethyl or isopropyl, most especially methyl groups.

Alk in compounds of the invention is preferably

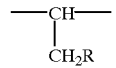

or, especially, —CH$_2$CH(R)—.

In one prefered class of compounds of formulae (1) and (2) R is a —CO$_2$H group.

In another prefered class of compounds of formulae (1) and (2) R is an esterified carboxyl group of formula —CO$_2$Alk$^7$. In this class of compound Alk$^7$ is preferably a C$_{1-8}$alkyl group, especially a methyl, ethyl, propyl, i-propyl, butyl or pentyl group, an optionally substituted C$_{3-8}$cycloalkyl group, especially a cyclopropyl, cyclobutyl, cyclopentyl, cyclohexyl or cycloheptyl group, an optionally substituted C$_{6-10}$aryl group, especially a phenyl group, an optionally substituted C$_{6-10}$arylC$_{1-6}$alkyl group, especially a benzyl group, an optionally substituted C$_{3-8}$heterocycloalkylC$_{1-6}$alkyl group, especially a morpholinyl-N-ethyl group, an optionally substituted N-di-C$_{1-8}$alkylaminoC$_{1-8}$alkyl group, especially a N-dimethylaminoethyl or N-diethylaminoethyl group, or a $C_{1-6}$alkyloxy$C_{1-6}$alkyl group, especially a methyloxyethyl group. Especially preferred esterified carboxyl groups include —$CO_2CH_3$, —$CO_2CH_2CH_3$, —$CO_2CH_2CH_2CH_3$ and —$CO_2CH(CH_3)_2$ groups.

In general in compounds of formulae (1) and (2) $R^1$ is preferably a hydrogen atom.

In general in compounds of formulae (1) and (2) $L^2$ is preferably $L^{2a}$ where $L^{2a}$ is an —O— atom or —$N(R^8)$— group in which $R^8$ is preferably a hydrogen atom or a methyl group. An especially useful —$N(R^8)$— group is —NH—.

In general in compounds of formula (2) $R^{17}$ $R^{17a}$ and $R^{17b}$ when present as an optional substituent is each preferably a halogen atom, especially a fluorine or chlorine atom or an $C_{1-6}$alkyl group, especially a methyl, ethyl, propyl or isopropyl group, a halo$C_{1-6}$alkyl group, especially —$CF_3$, a $C_{1-6}$alkoxy group, especially methoxy, ethoxy, propyloxy or isopropyloxy or halo$C_{1-6}$alkoxy, especially a trifluoromethoxy or difluoromethoxy, —CN, —$COR^3$, especially —$COCH_3$, a $C_{1-6}$alkylthio group, especially methylthio or ethylthio, a $C_{3-8}$cycloalkyl group, especially cyclopentyl or cyclohexyl or a $C_{1-6}$alkylenedioxy group, especially methylenedioxy or ethylenedioxy group.

In one preferred class of compounds of formula (2) $R^{17}$ is a halogen atom, especially a fluorine or chlorine atom, or a $C_{1-6}$alkoxy group, especially a methoxy group.

In one preferred class of compounds of formula (2) g is zero.

In another preferred class of compounds of formula (2) g is the integer 1. Particularly useful compounds of this class are those where $R^{17}$ is at the 6-, 7- or 8-position of the 3-substituted isoquinoline ring. Most especially useful compounds of this class are those where $R^{17}$ is at the 7-position of the 3-substituted isoquinoline ring.

In general in compounds of formulae (1) and (2) when n is zero or the integer 1 the group $R^2$ may especially be an optionally substituted heteroaliphatic, cycloaliphatic, heterocycloaliphatic, aromatic or heteroaromatic group as defined herein. Particularly useful groups of this type include optionally substituted $C_{2-6}$heteroalkyl, particularly $C_{1-3}$alkoxy$C_{1-3}$alkyl, especially methoxypropyl, optionally substituted $C_{3-7}$cycloalkyl, especially optionally substituted cyclopropyl, cyclobutyl cyclopropyl or cyclohexyl, optionally substituted $C_{5-7}$heterocycloaliphatic, especially optionally substituted pyrrolidinyl, thiazolidinyl, especially optionally substituted phenyl and optionally substituted $C_{5-7}$heteroaromatic, especially optionally substituted pyridyl groups. Optional substituents on these groups include in particular $R^{13}$ atoms or groups where the group is an aromatic or heteroaromatic group and —$(L^6)_p(Alk^5)_qR^{12}$ groups as described earlier where the group is a nitrogen-containing heterocycloaliphatic group such as a pyrrolidinyl or thiazolidinyl, pyrrolidinonyl, piperidinyl, homopiperidinyl, heptamethyleneiminyl, morpholinyl, piperazinyl or homopiperazinyl group. Particularly useful —$(L^6)_p(Alk^5)_qR^{12}$ groups include those in which $L^6$ is a —CO— group. $Alk^5$ in these groups is preferably present (i.e. q is preferably an integer 1) and in particular is a —$CH_2$-chain. Compounds of this type in which $R^{12}$ is a hydrogen atom or an optionally substituted aromatic or heteroaromatic group, especially an optionally substituted phenyl, pyridyl or imidazolyl group are particularly preferred.

In one preferred class of compounds of formulae (1) and (2) $L^1$ is present as a —$N(R^8)$— group. Particularly useful —$N(R^8)$— groups include —NH— and —$N(C_{1-6}$alkyl)—, especially —$N(CH_3)$—, —$N(CH_2 CH_3)$— and —$N(CH_2CH_2CH_3)$— groups. In this class of compounds n is preferably the integer 1 and $Alk^1$ is preferably an optionally substituted straight or branched $C_{1-6}$alkylene chain. Particularly useful $Alk^1$ chains include —$CH_2$—, —$CH_2CH_2$—, —$CH_2CH_2CH_2$—, —$CH(CH_3)CH_2$— and —$C(CH_3)_2CH_2$—. $R^2$ in this class of compounds is preferably a hydrogen atom.

In another preferred class of compounds of formulae (1) and (2) $L^1$ is a covalent bond, n is the integer 1 and $Alk^1$ is an optionally substituted straight or branched $C_{1-6}$alkylene chain. Particularly useful $Alk^1$ chains include optionally substituted —$CH_2$—, —$CH_2CH_2$—, —$CH_2CH_2CH_2$—, —$CH(CH_3)CH_2$— and especially —$C(CH_3)_2CH_2$— chains. $R^2$ in this class of compounds is preferably a hydrogen atom. A most especially useful optionally substituted $Alk^1R^2$ group is —$C(CH_3)_3$.

In another preferred class of compounds of formulae (1) and (2). $L^1$ is a covalent bond, n is zero and $R^2$ is an optionally substituted $C_{5-7}$heterocycloaliphatic group most especially an optionally substituted $C_{5-7}$heterocycloalkyl group. Especially useful $C_{5-7}$heterocycloalkyl groups include optionally substituted piperidinyl. homopiperidinyl (azepanyl), heptamethyleneiminyl, pyrrolidinyl, piperazinyl, homopiperazinyl, morpholinyl and thiomorpholinyl groups. Most preferred $C_{5-7}$heterocycloaliphatic groups are those linked via a ring nitrogen atom to the remainder of the compound of formulae (1) or (2). Most especially useful $C_{5-7}$heterocycloaliphatic groups include optionally substituted pyrolidin-1-yl, piperidin-1-yl and homopiperidin-1-yl groups. Especially useful optional substituents on these $C_{5-7}$heterocycloaliphatic groups include optionally substituted $C_{1-6}$alkyl groups, especially methyl, ethyl and i-propyl groups. Most preferred optionally substitued $C_{5-7}$heterocycloaliphatic groups include 2-methylpyrrolidin-1-yl, cis and trans 2,5-dimethylpyrrolidin-1-yl, 2-methylpiperidin-1-yl, cis and trans 2,6-dimethylpiperidin-1-yl, homopiperidin-1-yl (azepan-1-yl), 2-methylhomopiperidin-1-yl (2-methyazepan-1-yl) and cis and trans 2,7-dimethylhomopiperidin-1-yl groups.

Particularly useful compounds of the invention include:

(S)-3-[4-(3-Methyl-1-isoquinolinylamino)phenyl]-2-[(2-N,N-diethylamino-3,4-dioxocyclobut-1-enyl)amino]propanoic acid;

(S)-3-[4-(3-Methyl-1-isoquinolinylamino)phenyl]-2-[2(-(trans-2,5-dimethyloyrrolidinyl)-3,4-dioxocyclobut-1-enyl)amino]propanoic acid;

(S)-3-[4-(7-Chloro-3-methyl-1-isoquinolinylamino)phenyl]-2-[(2-(cis-2,5-dimethylpyrrolidinyl)-3,4-dioxocyclobut-1-enyl)amino]propanoic acid;

(S)-3-[4-(7-Fluoro-3-methyl-1-isoquinolinylamino)phenyl]-2-[(2-N,N-diethylamino-3,4-dioxocyclobut-1-enyl)amino]propanoic acid;

(S)-3-[4-(7-Fluoro-3-methyl-1-isoquinolinylamino)phenyl]-2-[(2-(cis-2,5-dimethylpyrrolidinyl)-3,4-dioxocyclobut-1-enyl)amino]propanoic acid;

(S)-3-[4-(7-Methoxy-3-methyl-1-isoquinolinylamino)phenyl]-2-[(2-N,N-diethylamino-3,4-dioxocyclobut-1-enyl)amino]propanoic acid;

(S)-3-[4-(7-Methoxy-3-methyl-1-isoquinolinylamino)phenyl]-2-[(2-(cis-2,5-dimethylpyrrolidinyl)-3,4-dioxocyclobut-1-enyl)amino]propanoic acid;

(S)-3-{4-[3-Chloro-1-isoquinolinyloxy]phenyl}-2-[2-(N,N-dipropylamino-3,4-dioxocyclobut-1-enyl)amino]propanoic acid;

(S)-3-{4-[3-Chloro-1-isoquinolinyloxy]phenyl}-2-{[2-(trans-2,5-dimethylpyrrolidinyl)-3,4-dioxocyclobut-1-enyl]amino}propanoate;

(S)-3-{4-[(3-Chloro-1-isoquinolinyl)oxy]phenyl}-2-{[2-(trans-2,5-dimethylpyrrolidinyl)-3,4-dioxocyclobut-1-enyl]amino}propanoic acid;

(S)-3-{4-[3-Chloro-1-isoquinolinyloxy]phenyl}-2-{[(azepan-1-yl)-3,4-dioxocyclobut-1-enyl]amino}propanoic acid;

(S)-3-[4-(7-Methoxy-3-methyl-7-isoquinolinylamino)phenyl]2-[(2-azepanyl-3,4-dioxocyclobut1-enyl)amino]propanoic acid;

and the salts solvates,. hydrates, N-oxides and carboxylic acid esters, particularly the methyl, ethyl, propyl and i-propyl esters thereof.

Most preferred compounds of the invention include:

(S)-3-[4-(7-Chloro-3-methyl-1-isoquinolinylamino)phenyl]-2-[(2-(cis-2,5-dimethylpyrrolidinyl)-3,4-dioxocyclobut-1-enyl)amino]propanoic acid;

(S)-3-[4-(7-Fluoro-3-methyl-1-isoquinolinylamino)phenyl]-2-[(2-(cis-2,5-dimethylpyrrolidinyl)-3,4-dioxocyclobut-1-enyl)amino]propanoic acid;

(S)-3-{4-[3-Chloro-1-isoquinolinyloxy]phenyl}-2-[2-(N,N-dipropylamino-3,4-dioxocyclobut-1-enyl)amino]propanoic acid (S)-3-{4-[(3-Chloro-1-isoquinolinyl)oxy]phenyl}-2-{[2-(trans-2,5-dimethylpyrrolidinyl)-3,4-dioxocyclobut-1-enyl]amino}propanoic acid;

(S)-3-{4-[3-Chloro-1-isoquinolinyloxy]phenyl}-2-{[(azepan-1-yl)-3,4-dioxocyclobut-1-enyl]amino}propanoic acid;

and the salts solvates, hydrates, N-oxides and carboxylic acid esters, particularly the methyl, ethyl, propyl and i-propyl esters thereof.

Compounds according to the inventions are potent and selective inhibitors of α4 integrins and have advantageous clearance properties, especially those compounds where R is a carboxylic ester or amide. The ability of the compounds to act in this way may be simply determined by employing tests such as those described in the Examples hereinafter.

The compounds are of use in modulating cell adhesion and in particular are of use in the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis. allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions. and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers: e.g. glass vials, The compositions for injection may take such forms as suspensions, solutions or emulsions in oily or aqueous vehicles. and may contain formulatory agents such as suspending, stabilising, preserving and/or dispersing agents. Alternatively, the active ingredient may be in powder form for constitution with a suitable vehicle, e.g. sterile pyrogen-free water, before use. For particle mediated administration the compounds of formula (1) may be coated on particles such as microscopic gold particles.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general. however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $Ar^1$, $Ar^2$, Alk, $R^1$, $R^2$, $L^1$, $L^2$, $Alk^1$ and n when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —$CO_2H$ group may be obtained by hydrolysis of an ester of formula (3):

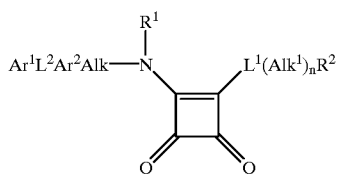

(3)

where Alk represents a group

—$CH_2CH(CO_2R^y)$—,  —$CH=CH(CO_2R^y)$—,

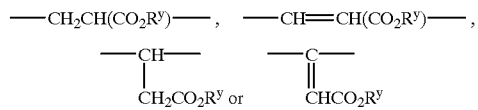

[where $R^y$ is an alkyl group for example a $C_{1-6}$alkyl group]

The hydrolysis may be performed using either an acid or a base depending on the nature of $R^y$, for example an organic acid such as trifluoroacetic acid or an inorganic base such as lithium, sodium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at a temperature from ambient to the reflux temperature. Where desired, mixtures of such solvents may be used.

According to a further aspect of the invention a compound of formula (1) may be prepared by displacement of a leaving group from a compound of formula (4):

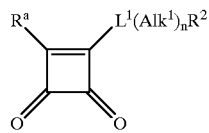

(4)

where $R^a$ is a leaving group, with an amine $Ar^1L^2Ar^2AlkN(R^1)H$ or a salt thereof. Suitable leaving groups represented by $R^a$ include halogen atoms, especially chlorine and bromine atoms, or alkoxy, e.g. methoxy, ethoxy or isopropoxy, aryloxy, e.g. dinitrophenyloxy, or aralkoxy, e.g. benzyloxy, groups.

The reaction may be performed in an inert solvent or mixture of solvents, for example a substituted amide such as dimethylformamide, an alcohol such as ethanol and/or a halogenated hydrocarbon such as dichloromethane, at a temperature from 0° C. to the reflux temperature. Where necessary, for example when a salt of an amine $Ar^1L^2Ar^2AlkN(R^1)H$ is used, an organic base such as diisopropylethylamine can be added.

Any carboxylic acid group present in the intermediate of formula (4) or the amine $Ar^1L^2Ar^2AlkN(R^1)H$ may need to be protected during the displacement reaction, for example as an ethyl ester. The desired acid may then be obtained through subsequent hydrolysis, for example as particularly described above and generally described below.

It will be appreciated that the displacement reaction may also be performed on a compound of formula (5):

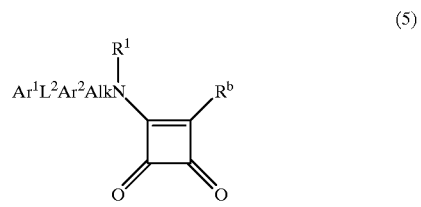

(5)

where $R^b$ is a leaving group as defined for $R^a$ using an intermediate $R^2(Alk^1)_nL^1H$ where —$L^1H$ is a functional group such as an amine (—$NH_2$) using the reaction conditions just described.

Where desired the displacement reaction may also be performed on an intermediate of formulae (4) or (5), $Ar^1L^2Ar^2AlkN(R^1)H$ or $R^2(Alk^1)_nL^1H$ which is linked, for example via its $Ar^1$ or $R^2$ group, to a solid support, such as a polystyrene resin. After the reaction the desired compound of formula (1) may be displaced from the support by any convenient method, depending on the original linkage chosen.

Intermediates of formulae (4) and (5) are either readily available or may be prepared from an intermediate of formula (6).

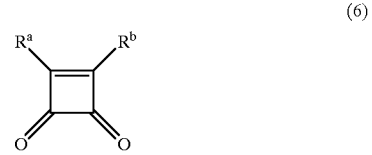

(6)

where $R^a$ and $R^b$ are as previously defined and an amine $Ar^1L^2Ar^2AlkN(R^1)H$ or $R^2(Alk^1)_nN(R^8)H$ by displacement as just described for the preparation of compounds of formula (1).

Intermediates of formulae $Ar^1L^2Ar^2AlkN(R^1)H$ and $R^2(Alk^1)_nN(R^8)H$ may be obtained from simpler, known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2) where appropriate functional groups exist in these compounds.

Thus compounds of the invention and intermediates thereto may be prepared by alkylation, arylation or heteroarylation. For example, compounds containing a —L$^1$H or —L$^2$H group (where L$^1$ and L$^2$ is each a linker atom or group) may be treated with a coupling agent R$^2$(Alk$^1$)$_n$X$^1$ or Ar$^1$X$^1$ respectively in which X$^1$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluene-sulphonyloxy group.

The reaction may be carried out in the presence of a base such as a carbonate, e.g. caesium or potassium carbonate, an alkoxide, e.g, potassium t-butoxide, or a hydride, e.g. sodium hydride, or an organic amine e.g triethylamine or N,N-diisopropylethylamine or a cyclic amine, such as N-methylmorpholine or pyridine, in a dipolar aprotic solvent such as an amide. e.g. a substituted amide such as dimethylformamide or an ether, e.g. a cyclic ether such as tetrahydrofuran.

Intermediates of formula Ar$^1$X$^1$ and R$^2$(Alk$^1$)$_n$X$^1$ are generally known, readily available compounds or may be prepared from known compounds by standard substitution and other synthetic procedures, for example as described herein. Thus for example compounds of formula Ar$^1$X$^1$ in which Ar$^1$ represents a 3-substituted isoquinolin-1-yl group may be prepared from alcohols of formula Ar$^1$OH by reaction with a halogenating agent, for example a phosphorous oxyhalide such as phosphorous oxychloride at an elevated temperature e.g. 110° C.

Intermediate alcohols of formula Ar$^1$OH in which Ar$^1$ represents a 3-substituted isoquinolin-1-yl group may be prepared by methods well known to a person skilled in the art, e.g. by the methods of Wu M.-J. et al Tetrahedron, 55, 13193–200 (1999), Hiebl J. et al Tetrahedron Lett. 40, 7935–8 (1999) and Brun E. M. et al Synlett, 7, 1088–90 (1999).

Further alkylating agents of formula Ar$^1$X$^1$ in which, for example, Ar$^1$ represents a isoquinolin-1-yl group, may be prepared by the methods of Falk H. et al Monatsch. Chem. 25, 325–33 (1994), and Deady, L. W. et al Aust. J. Chem 42, 1029–34 (1989).

In a further example intermediates of formula Ar$^1$L$^2$Ar$^2$AlkN(R$^1$)H may be obtained by reaction of a compound of formula Ar$^1$L$^2$H with a compound of formula X$^1$Ar$^2$AlkN(R$^1$)H under the reaction conditions just described.

Compounds of formula Ar$^1$L$^2$H in which, for example Ar$^1$ represents a 3-substituted isoquinolin-1-yl group and L$^2$ is a —N(R$^8$)— group, may be prepared by the methods of Bordner, J. et al J. Med. Chem. 31, 1036–9 (1988) and Molino, P et al J. Chem. Soc. Perkin Trans. 1 1727–31 (1990).

In another example, compounds containing a —L$^1$H or —L$^2$H or group as defined above may be functionalised by acylation or thioacylation, for example by reaction with one of the alkylating agents just described but in which X$^1$ is replaced by a —C(O)X$^2$, C(S)X$^2$, —N(R$^8$)COX$^2$ or —N(R$^8$)C(S)X$^2$ group in which X$^2$ is a leaving atom or group as described for X$^1$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which X$^1$ is replaced by a —CO$_2$H group) in the presence of a condensing agent, for example a diimide such as 1-(3-dimethylaminopropyl)-3-ethylcarbodiimide or N,N'-dicyclohexylcarbodiimide. advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which X$^1$ is replaced by a —S(O)Hal or —SO$_2$Hal group in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a —L$^1$H or —L$^2$H group as defined above may be coupled with one of the alkylation agents just described but in which X$^1$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —CO$_2$R$^5$, —CO$_2$Alk$^3$ or —CO$_2$Alk$^7$ in the compounds may be converted to the corresponding acid [—CO$_2$H] by acid- or base-catalysed hydrolysis depending on the nature of the groups R$^5$, Alk$^3$ or Alk$^7$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —OR$^5$ or —OR$^{14}$ groups [where R$^5$ or R$^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —OCH$_2$R$^{14}$ group (where R$^{14}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [CO$_2$Alk$^3$ or CO$^2$R$^5$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —OR$^5$ or —OR$^{14}$ group by coupling with a reagent R$^5$OH or R$^{14}$OH in a solvent such as tetrahydrofuran in the presence of a phosphine, e.g. triphenylphosphine and an activator such as diethyl-, diisopropyl-, or dimethylazodicarboxylate.

Aminosulphonylamino [—NHSO$_2$NHR$^2$ or —NHSO$_2$NHAr$^1$] groups in the compounds may be obtained, in another example, by reaction of a corresponding amine [—NH$_2$] with a sulphamide R$^2$NHSO$_2$NH$_2$ or Ar$^1$NHSO$_2$NH$_2$ in the presence of an organic base such as pyridine at an elevated temperature, e.g. the reflux temperature.

In another example compounds containing a —NHCSAr$^1$, —CSNHAr$^1$, —NHCSR$^2$ or —CSNHR$^2$ may be prepared by treating a corresponding compound containing a —NHCOAr$^1$, —CONHAr$^1$, —NHCOR$^2$ or —CONHR² group with a thiation reagent, such as Lawesson's Reagent, in an anhydrous solvent, for example a cyclic ether such as tetrahydrofuran. at an elevated temperature such as the reflux temperature.

In a further example amine (—NH₂) groups may be alkylated using a reductive alkylation process employing an aldehyde and a borohydride. for example sodium triacetoxyborohyride or sodium cyanoborohydride, in a solvent such as a halogenated hydrocarbon, e.g. dichloromethane, a ketone such as acetone, or an alcohol. e.g. ethanol, where necessary in the presence of an acid such as acetic acid at around ambient temperature.

In a further example, amine [—NH₂] groups in compounds of formula (1) may be obtained by hydrolysis from a corresponding imide by reaction with hydrazine in a solvent such as an alcohol, e.g. ethanol at ambient temperature.

In another example, a nitro [—NO₂] group may be reduced to an amine [—NH₂], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid. Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyidisulphide as the electrophile.

In another example, sulphur atoms in the compounds, for example when present in a linker group $L^1$ or $L^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In another example compounds of formula $Ar^1X^1$ (where $X^1$ is a halogen atom such as a chlorine, bromine or iodine atom) may be converted to such compounds as $Ar^1CO_2R^{20}$ (in which $R^{20}$ is an optionally substituted alkyl, aryl or heteroaryl group), $Ar^1CHO$, $Ar^1CHCHR^{20}$, $Ar^1CCR^{20}$, $Ar^1N(R^{20})H$, $Ar^1N(R^{20})_2$, for use in the synthesis of for example compounds of formula $Ar^1L^2Ar^2AlkN(R^1)H$, using such well know and commonly used palladium mediated reaction conditions as are to be found in the general reference texts *Rodd's Chemistry of Carbon Compounds,* Volumes 1–15 and Supplementals (Elsevier Science Publishers, 1989), *Fieser and Fieser's Reagents for Organic Synthesis,* Volumes 1–19 (John Wiley and Sons, 1999), *Comprehensive heterocyclic Chemistry,* Ed. Katritzky et al, Volumes 1–8, 1984 and Volumes 1–11, 1994 (Pergamon), *Comprehensive Organic Functional Group Transformations,* Ed. Katritzky et al, Volumes 1–7, 1995 (Pergamon), *Comprehensive Organic Synthesis,* Ed. Trost and Flemming, Volumes 1–9, (Pergamon, 1991), *Encyclopedia of Reagents for Organic Synthesis* Ed. Paquette, Volumes 1–8 (John Wiley and Sons, 1995), *Larock's Comprehensive Organic Transformations* (VCH Publishers Inc., 1989) and *March's Advanced Organic Chemistry* (John Wiley and Sons, 1992).

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means. for example by crystallisation and the desired enantiomer recovered. e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystallisation and other conventional separation procedures may also be used with intermediates or final products where it is desired to obtain a particular geometric isomer of the invention.

The following Examples illustrate the invention. All temperatures are in ° C. The following abbreviations are used:

NMM—N-methylmorpholine;
MeOH—methanol;
DCM—dichloromethane;
DIPEA—diisopropylethylamine;
Pyr—pyridine;
DMSO—dimethylsulphoxide;
Et₂O—diethylether;
THF—tetrahydrofuran,
FMOC—9-fluorenylmethoxycarbonyl;
RT—room temperature;
EtOAc—ethyl acetate;
BOC—butoxycarbonyl;
AcOH—acetic acid;
EtOH—ethanol;
Ar—aryl;
iPr—isopropyl;
Me—methyl;
DMF—N,N-dimethylformamide;
TFA—trifluoroactic acid;
All NMR's were obtained at 300 MHz unless otherwise specified.

Intermediate 1

3-Ethyl-1-isoquinolone

O-Toluic acid (2.0 g. 14.7 mmol) in THF (75 ml) was cooled to −78° and sec—BuLi (22.5 ml) added slowly. The resulting red solution was warmed to 0° for 30 min then cooled to −78°. Propionitrile (1.05 ml) in THF (10 ml) was added. the solution allowed to warm and stirred to RT for 16 h. Water (100 ml) was added and the product extracted into EtOAc (100 ml), washed with dilute HCl solution, water, brine, dried ((Na$_2$SO$_4$), and concentrated in vacuo. The crude product was purified by chromatography (SiO$_2$; 1–5% DCM/MeOH) ) to give the title compound (1.12 g, 44%) as a white solid. δH (CDCl$_3$) 8.37 (1H, d, J 8.0 Hz). 7.63 (1H, t, J 8.0 Hz), 7.48 (1H, d, J 8.0 Hz). 7.42 (1H, t, J 8.0 Hz), 6.33 (1H, s), 2.67 (2H, q, J 7.6 Hz), 1.33 (3H, t, J 7.6 Hz). m/z (ES$^+$, 70V) 174 (MH$^+$).

Intermediate 2

1-Chloro-3-ethylisoquinoline

The compound of Intermediate 1 (413 mg, 2.39 mmol) was dissolved in phosphorus oxychloride (5 ml) and heated to 80° for 2.5 h. The solution was cooled and concentrated, the residue dissolved in DCM and washed with ice cold NaHCO$_3$ solution, water, dried (Na$_2$SO$_4$), and concentrated in vacuo to give the crude product which was purified by washing through a plug of silica with DCM to give the title compound (438 mg, 95%) as a pale brown liquid. δH (CDCl$_3$) 8.29 (1H. d, J 8.5 Hz), 7.76 (1H, d, J 8.5 Hz), 7.66 (1H, t, J 8.5 Hz), 7.60 (1H, t, J 8.5 Hz), 7.42 (1H, s), 2.93 (2H, q, J 7.5 Hz), 1.38 (3H, t, J 7.5 Hz). m/z (ES$^+$, 70V) 194 (MH$^+$).

Intermediate 3

Methyl (S)-[2-tert-Butoxycarbonylamino]-3-{4-[3-ethyl-1-Isoquinolinylamino]phenyl}propanoate Methyl (S)-[tert-butoxycarbonylamino]-3-(4-aminophenyl)propanoate (351 mg, 1.1 9 mmol) and the compound of Intermediate 2 (230 mg) in 2-ethoxyethanol was heated at 80° for 1 h. The solution was cooled, concentrated in vacuo and purified by column chromatography (SiO$_2$; DCM/MeOH 50:1) to give the title compound (122 mg, 23%) as a colourless oil. δH (CDCl$_3$) 7.83 (1H, d, J 8.5 Hz), 7.68 (2H, d, J 8.0 Hz), 7.67 (1H, d, J 6.9 Hz), 7.60 (1H, t, J 6.9 Hz), 7.45 (1H, t, J 6.9 Hz), 7.14 (2H, d, J 8.5 Hz), 6.98 (1H, s), 5.00 (1H, m), 4.66 (1H, m), 3.74(3H, s), 3.10 (2H, m), 2.85 (2H, q, J 7.5 Hz), 1.44 (9H, s), 1.39 (3H, t, J 7.5 Hz). m/z (ES$^+$, 70V) 450 (MH$^+$).

Intermediate 4

Methyl (S)-2-amino-3-{4-[3-ethyl-1-isoquinolinylamino]phenyl}-propanoate

The compound of Intermediate 3 (120 mg, 0.27 mmol) was dissolved in DCM (2 ml) and treated with trifluoroacetic acid (0.20 ml) and stirred for 3 h. After this time the solvent was removed to give the title compound as a yellow oil which was used immediately in the next reaction. δH (DMSO) 8.50 (1H, br m), 8.54 (2H, d, J 8.2 Hz), 7.78 (3H, m), 7.61 (1H, m), 7.24 (2H, d, J 8.2 Hz), 7.10 (1H, s), 4.70 (1H, m), 3.71 (3H, s), 3.13 (2H, d, J 12.1 Hz), 2.72 (2H, q, J 7.5 Hz), 1.26 (3H, t, J 7.5 Hz). m/z (ES$^+$, 70V) 350 (MH$^+$).

Intermediate 5

Methyl (S)-3-{4-[3-chloro-1-isoquinolyloxylphenyl}-2-[(t-butoxycarbonyl)amino]propanoate To N-t-BOC-(S)-tyrosine methyl ester (545 mg, 1.85 mmol) in DMF (10 ml) were added 1,3-dichloroisoquinoline (402 mg., 2.03 mmol) and caesium carbonate (601 mg, 2.03 mmol) and the reaction heated to 45° for 18 h. The reaction was concentrated and the crude product purified by chromatography (SiO$_2$; 15–30% EtOAc/hexane) to give the title compound (804 mg, 95%) as a colourless glass. δH (CDCl$_3$) 8.38 (1H, d, J 9.2 Hz), 7.73 (2H, m), 7.59 (1H, m), 7.38 (1H, s), 7.21 (4H, s), 5.05 (1H, br s), 4.62 (1H, br m), 3.73 (3H, s), 3.13 (2H, m), 1.26 (9H, s). m/z (ES$^+$, 70V) 479 (MH$^+$).

Intermediate 6

3-t-Butyl-4-Isopropoxy-3-cyclobutene-1,2-dione t-Butyl lithium (2.29 ml of a 1.7M solution in pentane, 3.9 mmol) was added to a solution of 3,4-diisopropoxy-3-cyclobutene-1,2-dione (594 mg, 3 mmol) in THF (30 ml) at –78° C. After 5 h trifluoroacetic anhydride (636 µl, 4.5 mmol) was added and stirring continued at –78° C. for 30 min. The cold mixture was poured into NH$_4$Cl(aq), extraced with EtOAc, dried (Na$_2$SO$_4$) and evaporated in vacuo. Column chromatography (SiO$_2$; EtOAc/hexane, 15:85) gave the title compound as a mobile yellow oil (408 mg, 69%). δH (CDCl$_3$) 5.43 (1H, sept, J 6.2 Hz), 1.45 (6H, d, J 6.2 Hz) and 1.33 (9H, s); m/z (ES$^+$, 70V) 197 (MH$^+$).

Intermediate 7

3-Methyl-1-isoquiunolone

Prepared in a similar manner to the compound of Intermediate 1 to give the title compound as a white solid. δH (CDCl$_3$) 8.39 (1H, dd, J 8.4, 0.9 Hz), 7.64 (1H, t, J 8.4 Hz), 7.44 (1 H, d, J 8.4 Hz), 7.39(1 H, t, J 8.4 HZ). 6.30 (1 H, s), 2.39 (3H, d, J 0.9 Hz). m/z (ES$^+$, 70V) 160 (MH$^+$).

Intermediate 8

3-Isopropylisoquinolone

Prepared in a similar manner to the compound of intermediate 1 to give the title compound as a white solid. δH (CDCl$_3$) 8.39 (1H, d, J 8.0 Hz), 7.62 (1H, t, J 8.0 Hz), 7.49 (1H, d, J 8.0 Hz), 7.42 (1H, t, J 8.0Hz), 6.33 (1H, s,), 2.88 (1H, quin, J 7.0 Hz), 1.37 (6H, d, J 7.0 Hz). m/z (ES$^+$, 70V) 188 (MH$^+$).

Intermediate 9

4-Methoxy-2-methylbenzoic acid

Magnesium turnings (149 mg) and 4-bromo-3-methylanisole (1.0 g, 4.97 mmol) in THF were treated with a crystal of iodine and refluxed for 2 h. The solution was cooled, CO$_2$ (g) bubbled through the mixture whilst stirring for 2 h, Et$_2$O was added and the mixture washed with water, dried (Na$_2$SO4) and concentrated to give the title compound (620 mg, 75%) as a white solid. δH (CDCl$_3$) 8.08 (1H, d, J 7.7 Hz), 6.80 (1H, s), 6.78 (1H, d, J 7.7 Hz), 3.86 (3H, s), 2.65 (3H, s). m/z (ES$^+$, 70V) 167 (MH$^+$).

Intermediate 10

3-Ethyl-6-methoxy-1-isoqulnolone

Prepared in a manner similar to Intermediate 1 from Intermediate 9 and propionitrile to give the title compound as a white solid. δH (MeOD), 8.12 (1H, d, J 9.8 Hz), 7.03 (1H, d, J 9.8 Hz), 7.02 (1H, s), 6.41 (1H, s), 3.90 (3H, s ), 2.60 (2H, q, J 7.5 Hz), 1.29 (3H, t, J 7.5 Hz). m/z (ES$^+$, 70V) 204 (MH$^+$).

Intermediate 11

3-Trifluoromethyl-1-isoquinolone

Homophthalic acid (1.00 g, 5.55 mmol) dissolved in trifluoroacetic anhydride (7.8 ml) was heated in a sealed tube for 24 h at 110° followed by a further 24 h at 140°. The reaction was poured into water (100 ml), left for 1 h and the resulting precipitate extracted into EtOAc (3×50 ml). The EtOAc solution was dried (MgSO$_4$) and the solvent removed under reduced pressure to give a pale brown solid. LCMS showed these to be a 9:1 mixture of −1-oxo-3-(trifluoromethyl)-1H-isochromene-4-carboxylic acid. m/z (ES$^+$, 70V) 259 (MH$^+$) and 3-Trifluoromethyl)-1H-isochrom-1-one m/z (ES$^+$, 70V) 215 (MH$^+$). The solids were dissolved in concentrated ammonium hydroxide (70 ml) and heated for 4 days at 100°, an additional 10 ml of concentrated ammonium hydroxide added after 24 h. The solution was allowed to cool to room temperature, the precipitate removed by filtration and the filtrate extracted with EtOAc (1×50 ml). The EtOAc was dried (MgSO$_4$). the solvent removed under reduced pressure, and the resulting yellow solids combined with the precipitated material, to give the title compound 825 mg, 70%. δH (CDCl$_3$) 8.48 (1H, d, J 7.5 Hz), 7.77 (1H, t), 7.68 (2H, m), 6.95 (1H, s); m/z (ES$^+$, 70V), 215 (MH$^+$).

Intermediate 12

1-Chloro-3-trifluoromethylIsoquinoline

A solution of Intermediate 11 (800 mg) was heated at 80° for 8 h in POCl$_3$, then the reaction was concentrated under vacuum, the residues azeotroped with toluene (2×20 ml) and DCM (2×20 ml) and the residue taken up in DCM (50 ml). To this rapidly stirring, ice-cooled solution was added ice-cold saturated NaHCO$_3$ to pH 9–10. The organic layer was separated, combined with a further 30 ml DCM extract of the aqueous layer, dried (MgSO$_4$) and the solvent removed under reduced pressure to give the title compound 841 mg 97% as a brown solid. δH (CDCl$_3$) 8.42 (1H, d), 8.05 (1H, d), 7.98 (1H, d), 7.90 (2H, m). m/z (ES$^+$, 70V), 232 (MH$^+$).

Intermediate 13

Methyl (S)-3-{4-[3-trifluoromethyl-1-isoquinolinyloxy]phenyl}-2-[t-butoxycarbonylamino]propanoate Prepared in a similar manner to Intermediate 5 from the compound of Intermediate 12 to give the title compound as a colourless solid. δH (CD$_3$OD) 8.49 (1H, d, J 8.2 Hz), 8.06 (1H, d, J 8.1 Hz), 7.89 (2H, m), 7.83 (1H, t, J 7.6 Hz), 7.30 (2H, d, J 8.5 Hz), 7.22 (2H, d, J 8.5 Hz), 4.40 (1H, m), 3.69 (1H, s), 3.14 (1H, dd), 2.99 (1H, dd) and 1.40 (9H, s). m/z (ES$^+$, 70V) 513 (MNa$^+$).

Intermediate 14

Ethyl (S)-[2-(tert-butoxycarbonyl)amino]-3-{4-[(3-trifluoromethyl-1-isouinolinyl)amino]phenyl}propanoate Intermediate 12 (318 mg, 1.37 mmol) and methyl (S)-[tert-butoxycarbonyl) amino]-3-(4-aminophenyl)propanoate (403 mg, 1.31 mmol) were heated in ethoxy ethanol (1.5 ml) for 3 days at 120°. The solvent was removed under reduced pressure and the residue purified by chromatography (SiO$_2$, 20% EtOAc/Hexane) to give the title compound (78 mg, 12%) as a yellow glass. δH (CD$_3$OD) 8.48 (1H, d J 10.7 Hz), 7.87 (2H, m), 7.77 (2H, m), 7.55 (1H, s), 7.21 (1H, d, J 11.4 Hz), 4.37 (1H, m), 4.17 (2H, q, J 9.5 Hz), 3.09 (1H, m), 2.95 (1H, m), 1.42 (9H, s) and 1.25 (3H, t, J 9.5 Hz). m/z (ES$^+$, 70V) 504 (MH$^+$).

Intermediate 15

1-Chloro-3-ethylisoquinoline N-oxide

A solution of Intermediate 2 (500 mg, 2.6 mmol) in DCM at 0° was treated with 3-chloroperoxybenzoic acid (900 mg) in DCM and allowed to warm to room temperature. After 2 h the reaction was quenched with sodium sulphite solution, washed with saturated NaHCO$_3$ solution, water, dried (MgSO$_4$), and concentrated in vacuo and purified by chromatography (SiO$_2$; DCM/MeOH 100:1) to give the title compound (317 m, 59%) as a white solid. δH (CDCl$_3$)) 8.06 (1H, d, J 8.6 Hz), 7.74 (1H, d, J 8.6 Hz), 7.61 (2H, m), 7.52 (1H, s), 3.10 (2H, q, J 7.4 Hz), 1.41 (3H, t, J 7.4 Hz); m/z (ES$^+$, 70V) 208+210 (MH$^+$).

Intermediate 16

Methyl (S)-[2-(tert-Butoxycarbonyl)amino]-3-{4-[(3-ethyl-1-isoquinolinyl N-oxide)oxy]phenyl}propanoate A solution of N-BOC-(S)-tyrosine methyl ester (160 mg, 0.54 mmol) in DMC (1 ml) was treated in cesium carbonate (176 mg) and the compound of Intermediate 15, (112 mg) and stirred at 50° for 16 h. The mixture was concentrated and purified by chromatography (SiO$_2$; DCM/MeOH 100.1) to give the title compound (111 mg, 44%) as a white solid. δH (CDCl$_3$) 7.94 (1H, d, J 8.9 Hz), 7.80 (1H, d, J 8.9 Hz), 7.57 (2H, m); 7.52 (1H, s), 7.06 (2H, d, J 8.6 Hz), 6.82 (2H, d, J 8.6 Hz), 5.30 (1H, m), 4.55 (1H, m), 3.71 (3H, s), 3.06 (2H, m), 3.02 (2H, q, J 7.5 Hz), 1.41 (9H, s) and 1.40 (3H, t, J 7.5 Hz). m/z (ES$^+$, 70V) 467 (MH$^+$).

Intermediate 17

Methyl (S)-3-{4-[3-ethyl-1-isoquinolinyloxy]phenyl}-2-[(t-butoxycarbonyl)amino]propanoate To a solution of Intermediate 16 (630 mg, 1.35 mmol) in THF (20 ml) was added saturated NH$_4$Cl (20 ml) followed by zinc dust (397 mg, 6.08 mmol). The biphasic reaction was rapidly stirred for 20 mins, filtered through a Celite® pad, the THF layer separated, and the aqueous layer extracted with Et$_2$O. The organic layers were combined,dried (MgSO$_4$) and the solvent removed in vacuo to give the title compound as a colourless gum. δH (CD$_3$OD) 8.18 (1H, d), 7.65 (1H, dd), 7.57 (1H,d), 7.42 (1H, t), 7.20 (2H, d), 7.08 (3H, m), 4.41 (1H, m), 3.63 (3H, s), 3.08 (1H, dd), 2.96 (1H, dd): 2.58 (2H, q), 1.32 (9H, s) and 1.13 (3H, t); m/z (ES$^+$, 70V) 451 (MH$^+$).

Intermediate 18

Ethyl (4-methoxyphenyl)-2-methylacrylate

A solution of triethyl 2-phosphono propionate (17.5 g) in THF (200 ml) at 0° was treated with a n-butyl lithium (29.4 ml, 2.5 m in hexanes) and stirred for 20 min. p-Anisaldehyde (10 g, 73.4 mmol) in THF (50 ml) was added, the solution stirred at room temperature for 16 h, quenched with water, extracted into EtOAc, washed with water, dried (MgSO$_4$), and concentrated in vacuo. Chromatography (SiO$_2$; EtOAc/hexanes 1:20) gave the title compound (14.4 g, 89%) as a colourless liquid. δH (CDCl$_3$) 7.64 (1H, s), 7.39 (2H, d, J 8.7 Hz), 6.91 (2H, d, J 8.7 Hz), 4.25 (2H, q, J 7.1 Hz), 3.82 (3H, s), 2.13 (3H, s) and 1.34 (3H, t, J 7.1 Hz).

Intermediate 19

3-(4-Methoxyphenyl)-2-methyl acrylic acid

A solution of Intermediate 18 (8.72 g) in dioxan (10 ml) and sodium hydroxide solution (10 g in 120 ml water) was refluxed for 4 h, cooled and washed with Et$_2$O. The aqueous layer was acidified to pH 2 and the product extracted into EtOAc, dried (MgSO$_4$), concentrated in vacuo give the title compound (6.95 g. 91%) as a white solid. δH (CD$_3$OD) 7.64 (1H, d, J 1.1 Hz), 7.39 (2H, d, J 8.7 Hz), 6.95 (2H, d, J 8.7 HZ), 4.83 (1H, br s), 3.82 (3H, s), 2.09 (3H, d, J 1.1 Hz); m/Z (ES$^+$, 70V) 175 (MH$^+$—H$_2$O).

Intermediate 20

7-Methoxy-3-methyl-1-isoquinolone

A suspension of Intermediate 19 (3.5 g) in acetone (35 ml) was cooled to 0°, treated with triethylamine (3 ml), ethyl chloroformate (2.1 ml) and stirred for 20 min. Sodium azide (1.66 g) in water (10 ml) was added and the mixture warmed to room temperature and stirred for 2.5 h. The mixture was diluted with water and the volatiles removed in vacuo the organic layer dried (MgSO$_4$), and concentrated to half its volume, then added to phenyl ether at 220°. The mixture was heated at 220° for 2 h then cooled, Et$_2$O added and the precipitate isolated by filtration and dried (MgSO$_4$) to give the title compound (2.17 g, 63%) as a brown solid. δH (CDCl$_3$) 10.67 (1H, m), 7.76 (1H, s), 7.39 (1H, d, J 8.7 Hz), 7.25 (1H, d, j 8.7 Hz), 6.30 (1H, s), 3.93 (3H, s) and 2.37 (3H, s). m/z (ES$^+$, 70V) 190 (MH$^+$).

Intermediate 21

1-Chloro-7-methoxy-3-methylisoquinoline

Prepared in a manner similar to Intermediate 2 from the compound of intermediate 20 to give the title compound as a pale yellow solid. δH (IDMSO-d$^6$, 400 MHz) 7.89 (1H, d, J 8.9 Hz), 7.64 (1H, s), 7.47 (1H, dd, J 8.9, 2.5 Hz), 7.43 (1H, d, J 2.5 Hz), 3.93 (3H, s) and 2.53 (3H, s). m/z (ES$^+$, 70V) 208 (MH$^+$).

Intermediate 22

1-Chloro-3-methyl-7-methoxyisoquinoline N-oxide

Prepared in a similar manner to that described for Intermediate 15 to give the title compound as a white solid. δH (CDCl$_3$) 7.63 (1H, d, J 8.9 Hz), 7.52 (1H, s), 7.36 (1 Hz, m), 7.22 ( 1H, dd, J 8.9, 2.4 Hz), 3.98 (3H, s) and 2.67 (2H, s). m/z (ES$^+$, 70V) 224 (MH$^+$)

Intermediate 23

Methyl (S)-[2-(tert-Butoxycarbonyl)amino]-3-{4-[(3-methyl-7-methoxy-1-isoquinolinyl N-oxide)oxy]phenyl}propanoate Prepared in a similar manner to that described for Intermediate 16 from N-BOC-(S)-tyrosine methyl ester and the compound of Intermediate 22 to give the title compound as a white solid. δH (CDCl$_3$) 7.67 (1H, d, J 8.9 HZ), 7.50 (1H, s), 7.22 (2H, m), 7.08 (5.02 (1H, m), 4.58 (1H, m), 3.91 (3H, s) 3.74 (3H, s), 3.13 (2H, m) 2.61 (3H, s) and 1.43 (9H, s). m/z (ES$^+$, 70V) 483 (MH$^+$)

EXAMPLE 1

Methyl (S)-3-[4-(3-ethyl-1-isoquinolinylamino)phenyl]-2-[(2-isopropoxy-3,4-dioxocyclobut-1-enyl)amino]propanoate Intermediate 4 (0.2 mmol) in methanol (2 ml) was treated with 3,4-diisopropoxy-3-cyclobuten-1,2-dione (53 mg) and DIPEA (0.05 ml). The solution was stirred for 16 h then concentrated. The residue was dissolved in DCM, washed with water, dried (Na$_2$SO$_4$), filtered and concentrated to give the crude product. The crude product was purified by column chromatography (SiO$_2$; DCM/MeOH 50:1) to give the title compound (130 mg, 100%) as a colourless oil. δH (CDCl$_3$) 7.87 (1H, d, J 6.9 Hz), 7.73 (2H, d, J 8.5 Hz), 7.63 (1H, d, J 6.9 Hz), 7.46 (1H, t, J 6.9 Hz), 7.09 (2H, d, J 8.3 Hz), 6.99 (1H, s), 5.35 (1H, septet, J 6.2 Hz), 3.82 (3H, s), 3.19 (2H, m), 2.84 (3H, d, J 6.2 Hz), 1.41 (3H, d, J 6.2 Hz), 1.38 (3H, t, J 7.8 Hz). m/z (ES$^+$, 70V) 488 (MH$^+$).

EXAMPLE 2

Methyl (S)-3-[4-(3-ethyl-1-isoquinolinylamino)phenyl]-2-N,N-diethylamino-3,4-dioxocyclobut-1-enyl)amino]propanoate The compound of Example 1 (125 mg, 0.26 mmol) in MeOH (1 ml) was treated with diethylamine (0.05 ml) and stirred for 16 h. The solvent was removed and the residue dissolved in DCM, washed with water, dried (MgSO$_4$), concentrated and purified by column chromatography (SiO$_2$; DCM/MeOH 50:1) to give the title compound (102 mg. 78%) as a brown oil. δH (CDCl$_3$) 7.89 (1H, d, J 8.5 Hz), 7.73 (2H, d, J 8.5 Hz), 7.68 (1H, d, J 7.3 Hz), 7.60 (1H, t, J 7.8 Hz), 7.47 (1H, t, J 6.9 Hz), 7.09 (2H, d, J 8.5 Hz), 6.98 (1H, s), 5.43 (1H, m), 5.39 (1H, m), 3.24 (2H, d, J 5.2 Hz), 3.81 (3H, s), 3.55 (4H, m), 3.24 (2H, d, J 5.2 Hz), 2.82 (2H, q, J 7.5 Hz), 1.37 (3H, t, J 7.5 Hz), 1.23 (6H, t). m/z (ES$^+$, 70V) 501 (MH$^+$).

EXAMPLE 3

(S)-3-[4-(3-Ethyl-1-isoquinolinylamino)phenyl]-2-[(2-N,N-diethylamino-3,4-dioxocyclobut-1-enyl)amino]propanoic acid The compound of Example 2 (102 mg, 0.204 mmol) was dissolved in THF (1 ml) and water (1 ml) and treated with lithium hydroxide (11 mg) and stirred for 4 h. The solvent was removed and the residue purified by column chromatography (SiO$_2$; DCM /MeOH/ACOH/H$_2$O 200:20:6:4) to give the title compound (55 mg, 54%) as a yellow oil. δH (DMSO) 8.83 (1H, br m), 8.44 (1H, d, J 8.4 Hz), 7.87 (2H, d, J 8.4 Hz), 7.63 (1H, t, J 8.4 Hz), 7.49 (1H, t, J 8.3 Hz), 7.25 (1H, br m), 7.19 (2H, d, J 8.5 Hz), 6.98 (1H, s), 5.08 (1H, m), 3.55 (4H, m), 3.23 (1H, dd, J 14.1, 4.7 Hz), 3.06 (1H, dd, J 14.1, 4.6 Hz), 2.73 (2H, q, J 17.5 Hz), 1.31 (3H, t, J 7.5 Hz), 1.15 (6H, t, J 7.1 Hz). m/z (ES$^+$, 70V) 487 (MH$^+$).

EXAMPLE 4

Methyl-S)-3-[4-(3-ethyl-1-Isoquinolinylamino)phenyl]-2-[(2-N,N-dipropylamino-3,4-dioxocyclobut-1-enyl)amino]propanoate Prepared in a similar manner to the compound of Example 2 from the compound of Example 1 and dipropylamine to give the title compound. δH (DMSO, 350K), 8.93 (1H, s), 8.45 (1H, d, J 7.8 Hz), 7.88 (1H, d, J 8.6 Hz), 7.2 (1H, d, J 7.8 Hz), 7.65 (1H, t, J 7.8 Hz), 7.51 (1H, td, J 7.8, 5.5 Hz), 7.34 (1H, d, J 9.1 Hz), 7.19 (2H, d, J 8.6 Hz), 6.99 (1H, s), 5.24 (1H, m), 3.74 (3H, s), 3.51 (2H, sextet, J 7.3 Hz), 3.25 (1H, dd, J 13.6, 5.0 Hz), 3.10 (1H, dd, J 13.6, 3.4 Hz), 2.74 (2H, q, J 7.5 Hz), 1.56 (2H, sextet, J 7.3 Hz), 1.52 (2H, sextet, J 7.3 Hz), 1.31 (3H, t, J 7.5 Hz), 0.86 (6H, t, J 7.3 Hz). m/z (ES$^+$, 70V) 529 (MH$^+$).

EXAMPLE 5

(S)-3-[4-(3-ethyl-1-isoquinolinylamino)phenyl]-2-[(2-N,N-dipropylamino-3,4-dioxocyclobut-1-enyl)amino]propanoic acid Prepared in a similar manner to that described for the compound of Example 3 from the compound of Example 4 to give the title compound. δH (DMSO-d⁶, 1350K), 8.88 (1H, s), 8.45 (1H, d, J 7.4 Hz), 7.89 (2H, d, J 8.5 Hz), 7.71 (1H, d, J 7.4 Hz), 7.63 (1H, t, J 7.4 Hz), 7.50 (1H, t, J 7.4 Hz), 7.18 (2H, d, J 8 5 Hz), 6.98 (1H, s), 5.10 (1H, m), 3.52 (2H, sextet, J 7.3 Hz), 3.40 (2H, sextet, J 7.3 Hz), 3.24 (1H, dd, J 14.1, 4.6 Hz), 3.05 (1H, dd, J 14.1, 9.9 Hz), 2.74 (2H, qd, J 7.5, 0.4 Hz), 1.54 (4H, m), 1.31 (3H, t, J 7.5 Hz), 0.85 (6H, t, J 7.3 Hz). m/z (ES⁺, 70V) 515 (MH⁺).

EXAMPLE 6

Methyl-(S)-3-[4-3-ethyl-1-isoquinolinylamino) phenyl]-2-[(2-[2,5-dimethylpyrrolidinyl]-3,4-dioxocyclobut-1-enyl)amino]propanoate Prepared in a manner similar to Example 2 from the compound of Example 1 and 2,5-dimethylpyrrolidine to give the title compound as a yellow foamy solid. δH (DMSO-d⁶) 9.03 (1H, s), 8.45 (1H, d, J 8.3 Hz), 7.87 (2H, d, J 8.6 Hz), 7.65 (2H, m), 7.50 (1H, m), 7.18 (2H, d, J 8.6 Hz), 6.97 (1H, s), 5.74 (1H, m), 4.20 (2H, m), 3.71 (3H, s), 2.88 (1H, dd, J 14.1, 5.0 Hz), 2.68 (2H, q, J 7.5 Hz), 2.07 (2H, m), 1.67 (2H, m), 1.27 (3H, t, J 7.5 HZ), 1.21 (6H, t, J 6.3 Hz).

EXAMPLE 7

(S)-3-[4-(3-Ethyl-1-isoquinolinylamino)phenyl]-2-[(2-[2,5-dimethylpyrrolidinyl]-3,4-dioxocyclobut-1-enyl)amino]propanoic acid Prepared in a manner similar to Example 3 from the compound of Example 6 to give the title compound as a yellow glassy solid. δH (DMSO-d⁶, 350K), 9.02 (1H, s), 8.44 (1H, d, J 8.4 Hz), 7.85 (2H, d, J 8.4 Hz), 7.70 (1H, d, J 7.7 Hz), 7.62 (1H, t, J 7.7 Hz), 7.48 (1H, m), 7.46 (1H, m), 7.17 (2H, d, J 8.4 Hz), 6.97 (1H,s ), 6.50 (1H, m), 4.20 (2H, m), 3.21 (1H, dd, J 14.1, 4.8 Hz), 3.13 (1H, dd, J 14.1, 9.0 Hz), 2.73 (2H, q, J 7.5 Hz), 2.11 (2H, m), 1.69 (2H, m), 1.31 (3H, t, J 7.5 Hz), 1.28 (3H d, J 5.6 Hz), 1.24 (3H, s, J 6.4 HZ). m/z (ES⁺, 70V) 513 (MH⁺).

EXAMPLE 8

Methyl-(S)-3-[4-(3-methyl-1-isoquinolinylamino) phenyl]-2-[(2-isopropoxy-3,4-dioxocyclobut-1-enyl) amino]propanoate Prepared in a similar manner to that described for Example 1 from the Intermediate 7 to give the title compound as a colourless oil. δH (DMSO 350K, 400 MHz), 8.83 (1H, m), 8.42 (1H, dd, J 8.5, 0.7 Hz), 7.87 (2H, d, J 8.6 Hz), 7.68 (1H, d, J 8.5 Hz), 7.62 (1H, t, J 8.5 Hz), 7.49 (1H, t, J 8.5 Hz), 7.17 (2H, d, J 8.6 Hz), 5.19 (1H, septet, J 6.2 Hz), 3.74 (3H, s), 3.21 (2H, m), 2 45 (3H, s), 1.37 (6H, d, J 6.2 Hz), m/z (ES⁺, 70V) 474 (MH⁺).

EXAMPLE 9

Methyl-(S)-3-[4-(3-methyl-1-isoquinolinylamino) phenyl]-2-[(2-N,N-diethylamino-3,4-dioxo-1-cyclobut-1-enyl)amino]propanoate Prepared in a similar manner to that described for Example 2 from the compound of Example 8 to give the title compound as a brown solid. δH (CDCl₃) 7.88 (1H, d, J 8.4 Hz), 7.70 (2H, d, J 8.4 Hz), 7.65 (1H, t, J 8.4 Hz), 7.59 (1H, d, J 8.4 Hz), 7.46 (1H, t, J 8.4 Hz), 7.07 (2H, d, J 8.4 Hz), 6.98 (1H,s ), 5.41 (1H, m), 3.81 (3H, s), 3.48 (4H, m), 3.24 (2H, d, J 5.2 Hz), 2.54 (3H, s), 1.23 (6H, t, J 7.2 Hz). m/z (ES⁺, 70V) 487 (MH⁺).

EXAMPLE 10

(S)-3-[4-(3-Methyl-1-isoquinolinylamino)phenyl]-2-[(2-N,N-diethylamino-3,4-dioxocyclobut-1-enyl) amino]propanoic acid Prepared in a similar manner to that described for the compound of Example 3 from the compound of Example 9 to give the title compound. δH (DMSO, 350K) 8.85 (1H, br s), 8.44 (1H, dd, J 8.4, 0.8 Hz), 7.85 (2H, d, J 8.6 Hz), 7.66 (1H, d, J 8.4 Hz), 7.62 (1H, t, J 8.4 Hz), 7.48 (1H, t, J 8.4 Hz), 7.27 (1H, br m), 7.20 (2H, d, J 8.6 Hz), 6.97 (1H, s), 5.12 (1H, m), 3.54 (4H, m), 3.24 (1H, dd, J 14.1, 4.8 Hz), 3.07 (1H, dd, J 14.1, 9.6 Hz), 2.44 (3H, s, J 0.7 Hz), 1.15 (6H t, J 7.1 Hz). m/z (ES⁺, 70V) 473 (MH⁺).

EXAMPLE 11

Methyl-(S)-3-[4-(3-methyl-1-isoquinolinylamino) phenyl]-2-[(2-N,N-dipropylamino-3,4-dioxo-1-cyclobut-1-enyl)amino]propanoate Prepared in a similar manner to that described for Example 2 from the compound of Example 8 and dipropylamine to give the title compound as an orange oil. δH (CDCl₃) 7.89 (1H, d, J 8.5 Hz), 7.70 (2H, d, J 8.4 Hz), 7.65 (1H, t, J 8.0 Hz), 7.58 (1H, d, J 7.0 Hz), 7.47 (1H, t, J 7.0 Hz). 7.07 (2H, d, J 8.4 Hz), 6.98 (1H, s), 5.41 (1H, m), 5.29 (1H, m), 3.82 (3H, s), 3.45 (4H, m), 3.82 (3H, s), 3.45 (4H, m), 3.25 (2H, d, J 5.2 Hz), 2.54 (3H, s), 1.61 (4H, sextet, J 7.3 Hz), 0.88 (6H, t, J 7.3 Hz). m/z (ES⁺, 70V) 515 (MH⁺).

EXAMPLE 12

(S)-3-[4-(3-Methyl-1-isoquinolinylamino)phenyl]-2-[(2-N,N-dipropylamino-3,4-dioxocyclobut-1-enyl) amino]propanoic acid Prepared in a similar manner to that described for Example 3 from the compound of Example 11 to give the title compound as a yellow oil. δH (DMSO-D⁶) 8.99 (1H, s), 8.44 (1H, d, J 8.0HZ), 7.85 (2H, d, J 8.5 Hz), 7.66 (1H, d, J 8.0 Hz), 7.59 (1H, t, J 8.0 Hz), 7.49 (1H, t, J 8.0 Hz), 7.15 (2H, d, J 8.5 Hz), 6.97 (1H, s), 5.02 (1H, m), 3.49 (4H, m), 3.30 (1H, dd, J 14.1, 4.8 HZ), 3.07 (1H, dd, J 14.1, 9.3 Hz), 2.41 (3H, s), 1.48 (4H, m) 0.81 (6H, t, J 7.3 Hz). m/z (ES⁺, 70V) 501 (MH⁺).

EXAMPLE 13

Methyl-(S)-3-{4-[3-methyl-1-isoquinolinylamino] phenyl}-2-{[2-(2-methylpipenidinly)-3,4-dioxocyclobut-1-enyl]amino}propanoate Prepared in a similar manner to the compound of Example 2 from the compound of Example 8 and 2-methylpiperidine to give the title compound as a yellow foam. δH (DMSOd⁶), 8.83 (1H, s), 8.43 (1H, d, J 8.2 Hz), 7.88 (2H, d, J 8.6 Hz), 7.63 (3H, m), 7.50 (1H, t, J 8.0 Hz), 7.19 (2H, d, J 8.6 Hz), 6.99 (1H, s), 5.23 (1H, m), 4.47 (1H, m), 4.08 (1H, m), 3.72 (3H, s), 3.22 (1H, m), 3.06 (1H, m), 3.03 (3H, s), 1.72 (3H, m), 1.58 (3H, m), 1.24 (3H, d, J 6.9 Hz). m/z (ES⁺, 70V) 513 (MH⁺).

EXAMPLE 14

(S)-3-{4-[3-Methyl-1-isoquinolinylamino]phenyl}-2-{[2-(2-methylpiperidinyl)3,4-dioxocyclobut-1-enyl]amino}propanoic acid Prepared in a similar manner to the compound of Example 3 from the compound of Example 13 to give the title compound as a pale yellow foam. δH (DMSO-d⁶), 8.94 (1H, s), 8.53 (1H, d, J 8.4 Hz), 7.95 (2H, d, J 8.6 Hz), 7.71 (2H, m), 7.57 (1 H, t, J 8.4 Hz), 7.27 (2H, d, J 8.6 Hz), 7.06 (1H, s), 5.20 (1H, m), 4.54 (1H, m), 4.12 (1H, m), 3.10 (1H, m), 2.53 (3H, s), 1.69 (6H, m), 1.32 (3H d, J 6.9 Hz). m/z(ES⁺, 70V) 499 (MH⁺).

EXAMPLE 15

Ethyl-(S)-3-[4-(3-methyl-1-isoquinolinylamino)
phenyl]-2-[(2-(trans-2,5-dimethylpyrrolidinyl)-3,4-
dioxocycylobut-1-enyl)amino]propanoate The compound of Example 8 (400 mg, 0.76 mmol) in MeOH (5 ml) was treated with trans-2,5-dimethylpyrrolidine (0.2 ml, 2.28 mmol) and stirred at 50° for 24 h. The yellow precipitate was isolated by filtration to give the pure title compound as a white solid (236 mg, 62%).δH (DMSO-d⁶, 350K) 8.9 (1H,s) 8.5 (1H, d, J 8.0 Hz), 7.9 (1H, d, J 2.0 Hz), 7.8 (1H, d, J 6.0 Hz), 7.7 (1H, t J 5.0 Hz), 7.5 (1H, b, J 5.0 Hz), 7.3 (1H, d, J 5.0 Hz), 7.2 (1H, d, J 2.0 Hz), 6.9 (1H, s), 5.2 (1H, b, J 5.0 Hz), 4.3 (2H, b,J 7.0 Hz), 3.7 (3H, s), 3.3 (1H, d, J 5.0 Hz), 3.2 (1H, dd, J 10.0, 5.0 Hz), 3.1 (1H, dd, J 14.0, 5.0 Hz), 2.5 (3H, s), 2.1 (2H, d, J 3.0 Hz), 1.5 (2H, d, J 2.0 hz) and 1.1 (6H, d, J 6.0 Hz). m/z (ES⁺, 70V) 526 (MH⁺).

EXAMPLE 16

(S)-3-[4-(3-Methyl-1-isoquinolinylamino)phenyl]-2-
{[2-(trans-25-dimethyloyrrolidinyl)-3,4-
dioxocyclobut-1-enyl]amino}propanoic acid Prepared in a similar manner to that described for the compound of Example 3 from the compound of Example 15 to give the title compound as a yellow solid. δH (DMSO-d⁶, 350K) 8.8 (1H, br), 8.5 (1H,d, J 8.0 Hz), 7.8 (2H,d,J 8.0 Hz), 7.6 (1H, t, J 7.0 Hz), 7.5 (1H, t, J 7.0 Hz), 7.1 (2H, d, J 4.0 Hz), 6.9 (1H,s ), 4.9 (1H, m, J 7.0 Hz), 4.2 (2H, sept. J 7.0 Hz), 3.2 (1H, dd, J 14.0, 7.0 Hz) 3.1 (1H, dd, J 14.0, 8.0 Hz), 2.4 (3H, s), 2.1 (2H, q, J 7.0 Hz), 1.5 (2H, J 5.0 Hz) and 1.1 (5H, d, J 7.0 Hz). m/z (ESI, 70V) 498 (MH⁺)

EXAMPLE 17

Methyl-(S)-3-{4-[3-methyl-1-1Isoquinolinylamino]
phenyl}2-{[2-(cis-2,5-dimethylpyrrolidinyl)-3,4-
dioxocyclobut-1-enyl]amino}propanoate Prepared in a similar manner to the compound of Example 2 from the compound of Example 8 and cis-2,5-dimethylpyrrolidine to give the title compound as an orange foam. δH (DMSO-d⁶), 9.03 (1H, s), 8.45 (1H, d, J 8.0 Hz), 7.86 (2H, d, J 8.5 Hz), 7.63 (3H, m), 7.50 (1H, t, J 8.0 Hz), 7.20 (2H, d, J 8.5 Hz), 6.99 (1H, s), 5.17 (1H, m), 4.19 (2H, m), 3.72 (3H, s), 3.23 (1H, dd, J 13.8. 4.5 Hz), 3.03 (1H, dd, J 13.8, 10.9 Hz), 2.42 (3H, s), 2.09 (2H, m), 1.68 (2H, m), 1.25 (3H, d, J 6.5 Hz), 1.21 (3H, d, J 6.5 Hz). m/z (ES⁺, 70V) 513 (MH⁺).

EXAMPLE 18

(S)-3-{4-[3-Methyl-1-isoquinolinylamino]phenyl}-
2-{[2-(2,5-dimethylpyrrolidinyl)-3,4-dioxocyclobut-
1-enyl]amino}propanoic acid Prepared in a similar manner to the compound of Example 3 from the compound of Example 17 to give the title compound as a pale yellow solid. δH (DMSO-d⁶), 8.97 (1H, s), 8.40 (1H, d, J 8.3 Hz), 7.80 (2H, d, J 8.5 Hz), 7.63 (2H, m), 7.45 (1H, t, J 8.3 Hz), 7.16 (2H, d, J 8.5 Hz), 6.93 (1H, s), 4.97 (1H, m), 4.14 (2H, m), 3.16 (1H, dd, J 14.0, 4.2 Hz), 2.97 (1H, dd, J 14.0, 10.6 Hz), 2.45 (3H, s), 2.02 (2H, m), 1.62 (2H, m), 1.19 (3H, d, J 6.4 Hz), 1.15 (3H, d, 6.4 Hz). m/z (ES⁺, 70V) 499 (MH⁺).

EXAMPLE 19

Methyl (S)-3-[4-(7-chloro-3-methyl-1-
isoquinlinylamino)phenyl]-2-[(2-isopropoxy-3,4-
dioxocyclobut-1-enyl)amino]propanoate Prepared in a similar manner to the compound of Example 1 from the Intermediate 27 to give the title compound as a red oil. δH (DMSO-d⁶), 7.86 (1H, s), 7.71 (2H, d, J 7.8 Hz), 7.61 (1H, d, J 8.7 Hz), 7.53 (1H, d, J, 8.7 Hz), 7.11 (2H, d, J 8.4 Hz), 6.96 (1H, s), 5.40 (1H, m), 3.80 (3H, s), 3.20–3.10 (2H, m), 2.54 (3H, s), 1.42 (6H,d); m/z (ES⁺, 70V) 508 (MH⁺).

EXAMPLE 20

Methyl-(S)-3-[4-(7-Chloro-3-methyl-1-
isoquinolinylamino)phenyl]-2-[(2-(cis-2,5-
dimethylpyrrolidinyl)-3,4-dioxocyclobut-1-enyl)
amino]propanoate Prepared in a similar manner to the compound of Example 2 from the compound of Example 19 and 2,5-dimethylpyrrolidine to give the title compound. δH (DMSO-d⁶), 9.08 (1H, s), 8.60 (1H, s), 7.83 (2H, m), 7.73–7.60 (2H, m), 7.20 (2H, d, J 8.5 Hz), 6.99 (1H, s), 5.13 (1H, m), 4.15 (2H, br s), 3.69 (3H, s), 3.25–2.90 (2H, m), 2.38 (3H, s), 2.05 (2H, m), 1.62 (2H, m), 1.20 (6H, m). m/z (E⁺, 70V) 547 (MH⁺).

EXAMPLE 21

(S)-3-[4-(7-Chloro-3-methyl-1-isoquinolinylamino)
phenyl]-2-[(2-(cis -2,5-dimethylpyrrolidinyl)-3,4-
dioxocyclobut-1-enyl)amino]propanoic acid Prepared in a similar manner to the compound of Example 3 from the compound of Example 20 to give the title compound as a solid. δH (DMSO-d⁶), 9.0 (1H, s), 8.56 (1H, s), 7.73 (2H, d, J 8.4 Hz), 7.65 (1H, d, J 8.7 Hz), 7.56 (1H, d, J 8.7 Hz), 7.48 (1H, d, J 9.0 Hz), 7.13 (2H, d, J 8.5 Hz), 6.92 (1H,s), 4.97 (1H, m), 4.10 (2H, m), 3.25–2.90 (2H, m), 2.35 (3H, s), 2.00 (2H, m), 1.60 92H, m),1.16 (6H, m). m/z (ES⁺, 70V) 533 (MH⁺).

EXAMPLE 22

(S)-3-[4-(7-Chloro-3-methyl-1-isoquinolinylamino)
phenyl]-2-[(2-N,N -diethylamino-3,4-dioxocyclobut-
1-enyl)amino]propanoate Prepared in a similar manner to the compound of Example 2 from the compound of Example 19 and diethylamine to give the title compound δH (DMSO-d⁶, 340K) 8.94 (1H, s), 8.57 (1H, s), 7.83 (2H, m),7.70 (1H, d, J 8.7 Hz), 7.59 (1H, d, 8.7 Hz), 7.50 (1H, br s), 7.19 (2H, d, J 8.6 Hz),6.98 (1H, s), 5.21 (1H, m), 3.70 (3H, s), 3.30–2.90 (2H, m), 2.50 (4H, m), 1.00 (6H, m); m/z (ES⁺, 70V) 521 (MH⁺).

EXAMPLE 23

(S)-3-[4-(7-Chloro-3-methyl-1-isoquinolinylamino)
phenyl]-2-[(2-N,N -diethylamino-3,4-
dioxocycylobut-1-enyl)amino]propanoic acid Prepared in a similar manner to the compound of Example 3 from the compound of Example 22 to give the title compound as a white solid. δH (DMSO-d⁶) 9.13 (1H, s), 8.67 (1H, s), 7.88 (2H, m), 7.85–7.65 (2H, m), 7.26 (2H, d, J 8.5 Hz), 5.15 (1H, m), 3.60 (4H, m), 3.40–3.00 (2H, m), 2.45 (3H, s), 1.60 (6H, m); m/z (ES⁺, 70V) 507 (MH⁺).

EXAMPLE 24

Methyl-(S)-3-[4-(7-fluoro-3-methyl-1-isoquinolinylamino)phenyl]-2-[(2-isopropoxy-3,4-dioxocyclobut-1-enyl)amino]propionate Prepared in a similar manner to the compound of Example 1 from the Intermediate 26 to give the title compound as a solid δH (DMSO-d⁶), 9.02 (1H, d, J 8.4 Hz), 8.85 (1H, s), 8.21 (1H, d, J 9.7 Hz), 7.74 (2H, d, J 8.5 Hz), 7.65 (1H, m), 7.43 (1H, m), 7.05 (2H, d, J 8 4 Hz), 6.91 (1H, s), 5.05 (1H, m), 3.58 (3H, s), 3.10 (2H, m), 2.79 (1H, m), 2.30 (3H, s), 1.20 (6H, m); m/z (ES⁺, 70V) 492 (MH⁺).

EXAMPLE 25

Methyl-(S)-3-[4-(7-fluoro-3-methyl-1-isoquinolinylamino)phenyl]-2-[(2-N,N-diethylamino-3,4-dioxocyclobut-1-enyl)amino] propanoate Prepared in a similar manner to the compound of Example 2 from the compound of Example 24 and diethylamine to give the title compound a white solid. δH (DMSO-d⁶), 8.95 (1H, s), 8.32 (1H, dd, J 11.2, 1.6 Hz), 7.82 (2H, d, J 8.4 Hz), 7.79 (2H, m), 7.56 (1H, dt, J 8.7, 2.4 Hz), 7.19 (2H, J 8.5 Hz), 7.02 (1H, s), 5.20 (1H, m), 3.72 (3H, s), 3.53 (4H, br s), 3.21 (1H, dd, J 13.9, 4.4 Hz), 3.00 (1H, dd, J 13.9, 10.91 Hz), 2.41 (3H, s), 1.10 (6H, t, J 7.1 Hz). m/z (ES⁺70V) 505 (MH⁺).

EXAMPLE 26

(S)-3-[4-4-(7-Fluoro-3-methyl-1-isoquinolinylamino)phenyl]-2-[(2-N,N-diethylamino-3,4-dioxocyclobut-1-enyl)amino] propanoic acid Prepared in a similar manner to the compound of Example 3 from the compound of Example 25 to give the title compound as a solid. δH (DMSO-d⁶), 9.00 (1H, s), 8.37 (1H, d, J 10.8 Hz), 7.86–7.80 (3H, m), 7.74 (1H, d, J 9.1 Hz), 7.58 (1H, m), 7.22 (2H, d, J 8.5 Hz), 7.08 (1H, s), 5.10 (1H, m), 3.50–3.40 (4H, m), 3,30–2.95 (2H, m). 2.45 (3H, s), 1.11 (6H, m). m/z (ES⁺, 70V) 491 (MH⁺).

EXAMPLE27

Methyl-(S)-3-[4-(7-fluoro-3-methyl-1-isoquinolinylamino)phenyl]-2-[(2-(cis-2,5-dimethylpyrrolidinyl)-3,4-dioxocyclobut-1-enyl) amino]propanoate Prepared in a similar manner to the compound of Example 2 from the compound of Example 24 and 2,5-dimethylpyrrolidine to give the title compound as a white solid. δH (DMSO-d⁶), 8.71 (1H, s), 8.17 (1H, dd, J 11.3. 1.6 Hz), 7.72 (2H, m), 7.65 (1H, dd, J 9.0, 3.1 Hz), 7.40 (1H, dt, J 10.8, 2.4 Hz), 7.20 (1H, d, J 8.8 Hz), 7.08 (2H, d, J 8.6 Hz), 6.90 (1H, s), 5.08 (1H, m), 4.09 (2H, br s), 3.61 (3H, s), 3.11 (1H, dd, J 13.9, 8.9 Hz), 2.96 (1H, dd, J 16.8, 7.0 Hz), 2.40 (3H, s), 2.32 (3H, s), 1.99 (2H, m), 1.58 (2H, m), 1.14 (6H, t, J 6.8 Hz). m/z (ES⁺, 70V) 533 (MH⁺).

EXAMPLE 28

(S)-3-[4-(7-Fluoro-3-methyl-1-isoquinolinylamino) phenyl]-2-[(2-(cis-2.5-dimethylpyrrolidinyl)-3,4-dioxocyclobut-1-enyl)amino]propanoic acid Prepared in a similar manner to the compound of Example 3 from the compound of Example 27 to give the title compound as a solid δH (DMSO-d⁶), 8.90 (1H, s), 8.26 (1H, d, J 9.9 Hz), 8.80–8.70 (3H, m), 8.50 (2H, m), 7.12 (2H, d, J 8.4 Hz), 6.96 (1H, s), 4.98 (1H, m), 4.10 (2H, m), 3,20–2.85 (2H, m), 2.38 (3H, s), 2.00 (2H, m), 1.60 (2H, m), 1.15 (6H, m). m/z (ES⁺, 70V) 517 (MH⁺).

EXAMPLE 29

Ethyl (S)-3-{4-(3-methyl-7-methoxy-1-isoquinolinylamino]phenyl}2-[(2-isopropoxy-3,4-dioxocyclobut-1-enyl)amino]-propanoate Prepared in a similar manner to that described for Example 1 from the compound of Intermediate 21 to give the title compound as an orange foamy solid. δH (DMSO-d⁶) 8.80 (1H, br s), 8.70 (1H, s), 7.81 (2H, d, J 8.6 Hz), 7.78 (1H, d, J 8.9 Hz), 7.62 (1H, d, J 8.9 Hz), 7.28 (1H, dd, J 8.9, 2.4 Hz), 7.15 (2H, d, J 8.6 HZ), 6.92 (1H, s), 5.19 (1H, septet, J 6.2 Hz), 4.16 (2H, q, J 7.1 Hz), 3.19 (1H, dd, J 14.1, 5.0 Hz), 2.97 (1H, dd, J 14.1, 9.8 Hz), 2.38 (3H, d, J 0.7 Hz), 1.34 (6H, d, J 6.2 Hz), 1.21 (3H, t, J 6.2 Hz) and 4.70 (1H, m), m/z (ES⁺, 70V) 518 (MH⁺).

EXAMPLE 30

Ethyl (S)-3-[4-(7-methoxy-3-methyl-1-isoquinolinylamino)phenyl]2-[(2-N,N-diethylamino-3,4-dioxocyclobut-1-enyl)amino]propanoate Prepared in a similar manner to that described for Example 2 from the compound of Example 29 and diethylamine to give the title compound as a pale orange foamy solid. δH (DMSO-d⁶, 350K) 8.66 (1H, s), 7.80 (2H, d, J 8.6 Hz), 7.61 (1H, d, J 8.9 Hz), 7.35 (1H, d, J 8.9 Hz), 7.29 (1H, dd, J 8.9, 2.4 Hz), 7.18 (2H d, J 8.6 Hz), 6.93 (1H, s), 5.19 (1H, m), 4.19 (1H, q, J 7.1 Hz), 4.17 (1H, q, J 7.1 Hz), 3.94 (3H, s), 3.55 (2H, q, J 7.1 Hz), 3.53 (2H, q, J 7.1 Hz), 3.22 (1H, dd, J 14.1, 5.1 Hz), 3.06 (1H, dd, J 14.1, 9.7 Hz), 2.40 (3H, s), 1.23 (3H, t, J 7.1 Hz) and 1.14 (6H, t, J 7.1 Hz), m/z (ES⁺, 70V) 531 (MH⁺).

EXAMPLE 31

(S)-3-[4-(7-Methoxy-3-methyl-1-isoquinolinylamino)phenyl]2-[(2-N,N-diethylamino-3,4-dioxocyclobut-1-enyl)amino]propanoic acid Prepared in a similar manner to that described for the compound of Example 3 from the compound of Example 30 to give the title compound as a pale yellow solid. δH (DMSO-d⁶) 8.86 (1H, s), 7.80 (1H, d, J 8.9 Hz), 7.79 (2H, d, J 8.3 Hz), 7.66 (1H, br d. J 8.1 Hz), 7.63 (1H, d, J 8.9 Hz), 7.30 (1H, dd, J 8.9, 2.4 Hz), 7.19 (2H, d, J 8.3 Hz), 6.94 (1H,s ), 5.06 (1H, m), 3.92 (3H, s), 3.51 (6H, m), 3.21 (1H, dd, J 14.0, 4.1 Hz), 2.99 ((1H, dd, J 14.0, 10.8 Hz), 2.38 (3H, s), 1.11 (6H, t, J 7.1 Hz). m/z (ES⁺, 70V) 503 (MH⁺)

EXAMPLE 32

Methyl-(S)-3-[4-[(7-methoxy-3-methyl-1-isoquinolinylamino)phenyl]2-[(2-N,N-dipropylamino-3,4-dioxocyclobut-1-enyl)amino] propanoate Prepared in a similar manner to that described for Example 2 from the compound of Example 29 and dipropylamine to give the title compound as a yellow solid. δH (DMSO-d⁶) 8.90 (1H, s), 7.9 (4H, m), 7.30 (2H, d, J 8.0 Hz), 7.20 (2H, d, J 9.0 Hz), 6.95 (1H, s), 5.20 (1H, m), 3.90 (3H, s), 3.70 (3H, s), 3.20 (1H, dd, J 14.0, 5.0 Hz), 3.15 (4H, m), 3.05 (1H, dd, J 14.0, 9.0 Hz), 2.30 (3H, s) and 1.50 (4H, m), m/z (ES$^+$, 70V) 544 (MH$^+$).

EXAMPLE 33

(S)-3-[4-(7-Methoxy-3-methyl-1-isoquinolinylamino)phenyl]-2-[(2-N,N-dipropylamino-3,4-dioxocyclobut-1-enyl)amino]-}propanoic acid Prepared in a similar way to that described for the compound of Example 3 from the compound of Example 32 to give the title compound as a pale yellow solid. δH (DMSO-d$^6$, 400 MHz, 350K) 8.57 (1H, s), 7.9 (1H, s), 7.8 (2H, d, J 9.0 Hz), 7.6 (1H, d, J 9.0 Hz), 7.3 (2H, dd, J 9.0, 3.3 Hz), 7.1 (2H, d, J 7.0 Hz), 6.9 (1H,s ), 4.4 (1H, t, J 6.0 Hz), 3.95 (3H, s ), 3.5 (2H, m), 3,4 (2H, m), 3.1 (2H, d, J 5.0 Hz), 2.3 (3H, s), 1.5 (4H, sept. J 7.0 Hz) and 0.9 (6H, t, J 7.0 Hz), m/z (ES$^+$, 70V) 530 (MH$^+$).

EXAMPLE 34

Methyl-(S)-3-[4-(7-methoxy-3-methyl-1-isoquinolinylamino)phenyl-2-[(2-(cis,-2,5-dimethylpyrrolidinyl)-3,4-dioxocyclobut-1-enylenylamino]propanoate Prepared in a similar manner to that described for Example 2 from the compound of Example 29 and 2,5-dimethylpyrrolidine to give the title compound as an orange solid. δH (DMSO-d$^6$) 8.9 (1H, s), 7.9 (3H, m), 7.8 (1H, d, J 9.0 Hz), 7.7 (1H, d, J 9.0 Hz), 7.3 (1H, d, J 9.0 Hz), 7.2 (2H, d, J 11.0 Hz), 6.9 (1H, s), 5.2 (1H, sext. J 5.0 Hz), 4.1 (2H, m), 4.0 (3H, s), 3.7 (3H, s), 3.3 (1H, dd, J 17.0, 4.0 Hz), 3.05 (1H, dd, J 14.0, 11.0 Hz), 2.4 (3H, s), 2.1 (2H, q, J 5.0 Hz), 1.7 (2H, q. J 6.0 Hz) and 1.3 (6H, q, J 7.0 Hz); m/z (ESI$^+$70V) 542 (MH$^+$).

EXAMPLE 35

(S)-3-[4-[7-Methoxy-3-methyl-1-isoquinolinylamino)phenyl]-2-[(2-(cis-2,5-dimethylpyrrolidinyl)-3,4-dioxocyclobut-1-enyl)amino]propanoic acid Prepared in a similar manner to that described for Example 3 from the compound of Example 34 to give the title compound as a yellow solid. δH (DMSO-d$^6$, 350K) 8.7 (1H, s), 7.8 (1H, s), 7.7 (2H, d, J 2.0 Hz), 7.6 (1H, d, J 9.0 Hz), 7.3 (1H, d, J 3.0 Hz), 7.2 (2H, d, J 2.0 Hz), 6.9 (1H, s), 4.6 (1H, t, J 6.0 Hz), 4.1 (2H, m), 3.95 (3H, s), 3.25 (1H, dd, J 13.0, 6.0 Hz), 3.2 (1H, dd, J 14.0, 6.0 Hz), 2.4 (3H, s), 2.1 (2H, q, J 3.0 Hz), 1.6 (2H, q, J 3.0 Hz), 1.3 (3H, d, J 6.0 Hz) and 1.2 (3H, d, J, 7.0 Hz), m/z (ES$^+$, 70V) 525 (MH$^+$).

EXAMPLE 36

Methyl-(S)-3-[4-(7-methoxy-3-methyl-1-isoquinolinyl)amino)phenyl[-2-[(2-thiomorpholino-3,4-dioxocyclobut-1-enyl)amino]propanoate Prepared in a similar manner to that described in Example 2 from the compound of Example 29 and thiomorpholine to give the title compound as a brown oil. δH (DMSO-d$^6$) 8.9 (1H, s), 7.85 (3H, m), 7.7 (1H, d, J 9.0 Hz), 7.25 (2H, d, J 8.0 Hz), 7.15 (2H, d, J 7.0 Hz), 6.9 (1H, s), 4.15 (1H, q, J 9.0 Hz), 3.90 (3H, s), 3.20 (1H, dd, J m), 3.1 (1H, dd, J m), 2.70 (4H, t, J 2.0 Hz), 2.55 (1H, t, J 2.0 Hz), 2.40 (3H, s) and 1.2 (1H, t, J 8.0 Hz), (m/z (ES$^+$, 70V) 546 (MH$^+$).

EXAMPLE 37

(S)-3-[4-[(7-Methoxy-3-methyl-1-isoquinolinylamino)phenyl]-2-[(2-thiomorpholino-3,4-dioxocyclobut-1-enyl)amino]propanoic acid Prepared in a similar manner to that described for Example 3 from the compound of Example 36 to give the title compound as yellow solid. δH (DMSO-d$^6$) 8.9 (1H, s), 7.85-7.8 (3H, m), 7.71 (1H, d, J 9.0 Hz), 7.36 (1H, d, J 8.0 Hz), 7.20 (2H, d, J 8.0 Hz), 6.99 (1H, s), 4.75 (1H, m), 4.0 (4H, s), 3.9 (3H, m), 3.37 (2H, m) 3.27 (1H, m), 3.01 (1H, dd, J 14.0. 9.0 Hz) and 2.46 (3H, s), m/z (ES$^+$, 70V) 532 (MH$^+$).

EXAMPLE 38

Methyl-(S)-3-[4-(7-methoxy-3-methyl-1-isoquinolinylamino)phenyl]-2-[(2-azepanyl-3,4-dioxocyclobut-1-enyl)amino]propanoate Prepared in a similar manner to that described for Example 2 from the compound of Example 29 and azepane to give the title compound as brown oil. δH (DMSO-d$^6$) 8.03 (1H, s), 7.66 (2H, d, J 9.0 Hz), 7.2 (1H, d, J 8.0 Hz), 7.01 (1H, d, J 7.0 Hz), 6.96 (1H, s), 6.65 (1H, d, J 9.0 Hz), 5.23 (1H, s, J 8.0 Hz), 3.94 (3H, s), 3.73 (3H, s), 3.22 (1H, dd, J 14.0, 4.0 Hz), 3.21 (2H, t, J 6.0 Hz), 2.75 (1H, dd, J 14.0, 4.0 Hz), 2.61 (2H, t, J 6.0 Hz), 2.53 (3H, s), 1.6 (4H, br) and 1.4 (4H, br), m/z (ES$^+$, 70V) 542 (MH$^+$).

EXAMPLE 39

(S)-3-[4-(7-Methoxy-3-methyl-7-isoquinolinylamino)phenyl]2-[(2-azepanyl-3,4-dioxocyclobut-1-enyl)amino]propanoic acid Prepared in a similar manner to that described for Example 3 from the compound of Example 38 to give the title compound as a yellow solid. δH (DMSO-d$^6$, 350K) 8.88 (1H,s), 8.0 (1H, s), 7.85 (3H, m), 7.68 (1H, d, J 8.0 Hz), 7.37 (1H, d, J 2.0 Hz), 7.35 (1H, d, J 2.0 Hz), 7.18 (1H, d, J 2.0 Hz), 6.99 (1H, s), 6.70 (1H, d, J 8.0 Hz), 4.76 (1H, m), 3.9 (3H, s), 3.61 (1H, m), 3.34 (1H, q, J 3.0 Hz), 3.21 (1H, dd, J 14.0, 5.0 Hz), 3.09 (1H, dd, J 14.0, 8.0 Hz), 2.75 (1H, q, J 9.0 Hz), 2.48 (1H, m, J 8.0 Hz), 2.45 (3H, s), 1.65 (4H, m) and 1.52 (4H, m). m/z (ES$^+$, 70V) 528 (MH$^+$)

EXAMPLE 40

Methyl(S)-3-[4-(7-methoxy-3-methyl-1-isoquinolinyloxy)phenyl]-2-[(2-isopropoxy-3,4-dioxocyclobut-1-enyl)amino]propanoate A solution of Intermediate 23 (780 mg, 1.62 mmol) in THF (20 ml) and 30% ammonium chloride solution (20 ml) was treated with zinc dust (473 mg) and stirred at room temperature for 15 min. The product was extracted into EtOAc, washed with water, dried (MgSO$_4$), and concentrated in vacuo. The crude material was dissolved in EtOAc and treated with excess HCl gas, stirred for 30 min and then concentrated in vacuo. The residue was dissolved in MeOH and treated with Hunigs base (0.3 ml) and 3,4-diisopropoxy-3-cyclobuten-1,2-dione (320 mg), stirred at room temperature for 16 h and concentrated in vacuo. Chromatography (SiO$_2$; DCM/MeOH 100.1 to 50:1) gave the title compound (550 mg, 67%) as a colourless oil. δH (DMSO-d$^6$, 350K) 8.81 (1H, m), 7.78 (1H, d, J 8.9 Hz), 7.57 (1H, s), 7.43 (1H, dd, J 8.9, 2.7 Hz), 7.29 (2H, d, J 8.6 Hz), 7.28 (1H, s), 7.18 (2H, d, J 8.6 Hz), 5.22 (1H, septet, J 6.1 Hz), 4.75 (1H, m), 3.92 (3H, s), 3.74 (3H, s), 3.29 (1H, dd, J 14.1, 4.9 Hz), 3.08 (1H, dd, J 14.1, 9.9 Hz), 2.35 (3H, d, J 0.8 Hz), 1.38 (3H, d, J 6.1 Hz) and 1.36 (3H, d, J 6.1 Hz), m/z(ES$^+$, 70V) 505 (MH$^+$).

EXAMPLE 41

Methyl (S)-3-[4-(7-methoxy-3-methyl-1-isoquinolinyloxy)phenyl]2-[(2-N,N-diethylamino-3,4-dioxocyclobut-1-enyl)amino]propanoate Prepared in a similar manner to that described for Example 2 from the compound of Example 40 and diethylamine to give the title compound as a white solid. δH (DMSO-d⁶, 350K) 7.77 (1H, d, J 8.9 Hz), 7.56 (1H, d, J 2.6 Hz), 7.40 (1H, dd, J 8.9, 2.6 Hz), 7.30 (2H, d, J 8.6 Hz), 7.27 (1H, s), 7.16 (2H, d, J 8.6 Hz), 5.27 (1H, dd, J 10.0, 5.1 Hz), 3.91 (3H, s), 3.73 (3H, s), 3.55 (2H, q, J 7.1 Hz), 3.53 (2H, q, J 7.1 Hz), 3.53 (2H, q, J 7.1 Hz), 3.29 (1H, dd, J 14.1, 5.1 Hz), 3.13 (1H, dd, J 14.1, 10.0 Hz), 2.34 (3H, d, J 0.7 Hz) and 1.4 (6H, t, J 7.1 Hz). m/z (ES⁺, 70V) 518 (MH⁺).

EXAMPLE 42

(S)-3-[4-(7-Methoxy-3-methyl-1-isoquinolinyloxy)phenyl]-2-[(2-N,N-diethylamino-3,4-dioxocyclobut-1-enyl)amino]propanoic acid Prepared in a similar manner to that described for Example 3 from the compound of Example 41 to give the title compound as a white solid. δH (DMSO-d⁶, 350K) 7.77 (1H, d, J 8.9 Hz), 7.56 (1H, d, J 2.6 Hz), 7.40 (1H, dd, J 8.9, 2.6 Hz), 7.31 (2H, d, J 8.6 Hz), 7.26 (1H, s), 7.17 (2H, d, J 8.6 Hz), 5.18 (1H, m), 3.91 (3H, s), 3.55 (4H, septet, J 7.1 Hz), 3.29 (1H, dd, J 14.1, 4.6 Hz), 3.11 (1H, dd, J 14.1, 10.1 Hz), 2.34 (3H, d, J 0.8 Hz) and 1.14 (6H, t, J 7.1 Hz). m/z (ES⁺, 70V) 504 (MH⁺).

EXAMPLE 43

Methyl (S)-3-[4-(3-methyl-7-methoxy-1-isoquinolinylox)phenyl]-2-[(2-(cis-2,5-dimethylpyrrolidinyl)-3,4-dioxocyclobut-1-enyl)amino]propanoate Prepared in a similar manner to the compound of Example 41 from the compound of Example 40 and cis-2,5-dimethylpyrrolidine to give the title compound. δH (DMSO-d⁶) 7.77 (1H, d, J 8.9 Hz), 7.56 (1H, m), 7.32 (6H, m), 5.22 (1H, m), 4.53 (1H, m), 4.16 (2H, m) 3.89 (3H, s), 3.72 (3H, s), 3.58 (1H, m), 3.30 (1H, m), 2.30 (3H, s), 2.05 (2H, m), 1.68 (2H, m) and 1.19 (6H, d, J 6.5 Hz); m/z (ES⁺, 70V) 758 (MH⁺).

EXAMPLE 44

(S)-3-[4-(7-Methoxy-3-methyl-1-isoquinolinyloxy)phenyl]-2-[(2-(cis-2,5-dimethylpyrrolidinyl)-3,4-dioxocyclobut-1-enyl)amino]propanoic acid Prepared in a similar manner to that described for Example 3 from the compound of Example 43 to give the title compound as a pale yellow oil. δH (DMSO-d⁶, 350K) 7.77 (1H, d, J 8.9 Hz), 7.57 (1H, d, J 2.6 Hz), 7.41 (1H, dd, J 8.9, 2.6 Hz), 7.32 (2H, d, J 8.6) 7.27 (1H,s ), 7.16 (2H, d, J 8.6 Hz), 5.11 (1H, dd, J 9.5, 5.5 Hz), 4.21 (2H, m), 3.92 (3H, s), 3.30 (1H, dd, J 14.2, 4.8 Hz), 3.14 (1H, dd, J 14.2, 9.6 Hz), 2.35 (3H, d, J 0.7 Hz), 2.11 (2H, m), 1.70 (2H, m), 1.29 (3H, d, J 6.4 Hz) and 1.24 (3H, d, J 6.4 Hz). m/z (ES⁺, 70V) 530 (MH⁺).

EXAMPLE 45

Ethyl (S)-3-[4-(3-isopropyl-1-isoquinolinylamino)phenyl]-2-[(2-isopropoxy-3,4-dioxocyclobut-1-enyl)amino]propanoate Prepared in a similar manner to Example 1 from the Intermediate 8 to give the title compound as a pale brown solid. δH (DMSO-d⁶, 350K) 8.86 (1H, s), 8.75 (1H, m), 8.45 (1H, d, J 8.1 HZ), 7.93 (2H, d, J 8.6 Hz), 7.73 (1H, d, J 8.1 Hz), 7.64 (1H, t, J 8.1 Hz). 7.50 (1H, t, J 8.1 Hz), 7.18 (2H, d, J 8.6 Hz), 6.99 (1H, s), 5.22 (1H, m), 4.71 (1H, m), 4.19 (2H, qd, J 7.1, 0.8 Hz), 3.24 (1H, m), 3.05 (2H, m), 1.38 (3H, t, J 6.1 Hz), 1.36 (3H, t, J 6.2 HZ), 1.31 (3H, t J 6.9 Hz), 1.23 (3H, t, J 7.1 Hz). m/z (ES⁺, 70V) 516 (MH⁺).

EXAMPLE 46

Ethyl (S)-3-[4-(3-isopropyl-1-isoquinolinylamino)phenyl]-2-[(2-NN-dipropylamino-3,4-dioxocyclobut-1-enyl)-amino]propanoate Prepared in a similar manner to Example 2 from the compound of Example 45 and dipropylamine to give the title compound as a pale yellow solid. δH (DMSO-d⁶, 350K)) 8.84 (1H, s), 8.44 (1H, d, J 8.4 Hz), 7.92 (2H, d, J 8.6 Hz), 7.72 (1H, d, J 8.4 Hz), 7.63 (1H, t, J 8.4 Hz), 7.50 (1H, t, J 8.4 Hz), 7.32 (1H, d, J 8.9 Hz), 7.18 (2H, d, J 8.6 Hz), 6.99 (1H, s), 5.25 (1H, m), 3.74 (3H, s), 3.46 (4H, m), 3.25 (1H, dd, J 14.1, 4.9 Hz), 3.08 (1H, dd, J 14.1, 9.9 Hz), 2.99 (1H, m), 1.52 (4H, m), 1.31 (6H, d, J 6.9 Hz), 0.86 (6H, t, J 7.3 Hz). m/z (ES⁺, 70V) 543 (MH⁺).

EXAMPLE 47

(S)-3-[4-(3-Isopropyl-1-Isoquinolinylamino)phenyl]-2-[(2-NN-dipropylamino-3,4-dioxocyclobut-1-enyl)amino]propanoic acid Prepared in a similar manner to Example 3 from the compound of Example 46 to give the title compound as a pale yellow glass. δH (DMSO-d⁶, 350K) 8.83 (1H, s), 8.46 (1H, d, J 8.4 Hz), 7.92 (2H, d, J 8. Hz), 7.72 (1H, d, J 8.4 Hz), 7.63 (1H, t, J 8.4 Hz), 7.50 (1H, t, J 8.4 Hz), 7.19 (2H, d, J 8.6 Hz), 6.99 (1H, s), 5.14 (1H, m), 3.51 (2H, quin, J 7.3 Hz), 3.40 (2H, quin, J 7.3 Hz), 3.24 (1H, dd, J 14.1, 7.3 Hz), 3.06 (1H, dd, J 14.1, 9.8 Hz), 2.99 (1H, septet, J 6.8 Hz), 1.54 (4H, m), 1.31 (6H, d, J 6.8 Hz), 0.85 (6H, t, J 7.3 Hz). m/z (ES⁺, 70V) 529 (MH⁺).

EXAMPLE 48

Ethyl (S)-3-[4-(3-isopropyl-1-Isoquinolinylamino)phenyl]-2-[(2-N,N-diethylamino-3,4-dioxocyclobut-1-enyl)amino]propanoate Prepared in a similar manner to Example 2 from the compound of Example 45 and diethylamine to give the title compound as a pale yellow solid. δH (DMSO-d⁶, 350K) 8.85 (1H, s), 8.44 (1H, d, J 8.4 Hz), 7.91 (2H, d, J 8.6 Hz), 7.74 (1H, d, J 8.4 Hz), 7.63 (1H, t, J 8.4 Hz), 7.50 (1H, t, J 8.4 Hz), 7.40 (1H, d, J 8.9 Hz), 7.20 (2H, d, J 8.6 Hz), 6.99 (1H, s), 5.24 (1H, m), 3.74 (3H, s), 3.55 (4H, m), 3.24 (1H, dd, J 14.1, 5.0 Hz). 3.05 (1H, dd, J 14.1, 9.9 Hz), 3.01 (1H, m), 1.31 (6H, d, J 6.8 Hz), 1.15 (6H, t, J 7.1 Hz), m/z (ES⁺, 70V) 515 (MH⁺).

EXAMPLE 49

(S)-3-[4-(3-Isopropyl-1-isoquinolinylamino)phenyl]-2-[(2-N,N-diethylamino-3,4-dioxocyclobut-1-enyl)amino]propanoic acid Prepared in a similar manner to Example 3 from the compound of Example 48 to give the title compound as a pale yellow glass. δH (DMSO-d⁶, 350K) 8.83 (1H, s), 8.44 (1H, dd, J 8.4, 0.8 Hz), 7.89 (2H, d, J 8.5 Hz), 7.71 (1H, dd, J 8.0, 1.2 Hz), 7.62 (1H, ddd, J 8.0, 6.8, 1.2 Hz), 7.48 (1H, ddd, J 8.3, 6.8, 1.2 Hz), 7.27 (1H, d, J 9.1 Hz), 7.20 (2H, d, J 8.5 Hz), 6.99 (1H, s), 5.12 (1H, m), 3.24 (1H, dd, J 14.1, 4.7 Hz), 3.03 (2H, m), 1.32 (3H, d, J 6.9 Hz), 1.31 (3H, d, J 6.8 Hz), 1.15 (6H, t, J 17.1 Hz). m/z (ES⁺, 70V) 501 (MH⁺).

EXAMPLE 50

Ethyl-(S)-3-[4-(3-ethyl-6-methoxy-1-isoquinolinylamino)phenyl]-2-[(2-Isopropoxy-3,4-dioxocyclobut-1-enyl)amino]propanoate Prepared in a manner similar to Example 1 from the compound of Intermediate 10 to give the title compound as an orange foam. δH (DMSO-d$^6$, 350K) 8.75 (1H, m), 8.34 (1H, d, J 8.7 Hz), 7.98 (1H, m), 7.85 (2H, d, J 8.6 Hz), 7.15 (2H, d, J 8.6 Hz), 7.12 (1H, s), 7.09 (1H, d, J 8.7 Hz), 6.92 (1H, s), 5.21 (1H, m), 4.70 (1H, m), 4.20 (2H, q, J 7.1 Hz), 3.91 (3H, s), 3.23 (1H, m), 3.19 (1H, m), 2.69 (2H, q, J 7.5 Hz), 1.38 (6H, d, J 6.2 Hz), 1.29 (3H, t, J 7.5 Hz), 1.23 (3H, t, J 7.1 Hz). m/z (ES$^+$, 70V) 532 (MH$^+$).

EXAMPLE 51

Ethyl-(S)-3-[4-(3-ethyl-6-methoxy-1-isoquinolinylamino)phenyl]-2-[(2-N,N-diethylamino-3,4-dioxocyclobut-1-enyl)amino]propanoate Prepared in a manner similar to Example 2 from the compound of Example 50 and diethylamine to give the title compound as a pale orange solid. δH (DMSO-d$^6$, 350K) 8.73 (1H, s), 8.35 (1H, d, J 8.7 HZ), 7.85 (2H, d, J 8.6 Hz), 7.39 (1H, m), 7.17 (2H, d, J 8.6 Hz). 7.12 (1H, s), 7.11 (1H, d, J 8.7 Hz), 6.91 (1H, s), 5.23 (1H, m), 3.91 (3H, s ), 3.73 (3H, s), 3.53 (4H, septet, J 7.1 Hz), 3.21 (1H, dd, J 14.0, 5.0 Hz), 3.06 (1H, dd, J 14.0, 9.8 Hz), 2.69 (2H, q, J 7.5 Hz), 1.28 (3H, t, J 7.5 Hz), 1.15 (6H, t, 7.1 Hz). m/z (ES$^+$, 70V) 531 (MH$^+$).

EXAMPLE 52

(S)-3-[4-(3-Ethyl-6-methoxy-1-isoquinolinylamino)phenyl]-2-[(2-N,N-diethylamino-3,4-dioxocyclobut-1-enyl)amino]propanoic acid Prepared in a manner similar to Example 3 from the compound of Example 51 to give the title compound as a pale yellow glassy solid. δH (DMSO-d$^6$, 350K) 8.71(1H, m), 8.34 (1H, d, J 8.6Hz), 7.83 (2H, d, J 8.5 Hz), 7.26 (1H, m), 7.17 (2H, d, J 8.5 Hz), 7.10 (1H, s), 7.09 (1H, d, J 8.7 Hz), 6.90 (1H,s), 5.09 (1H, m), 3.91 (3H, s), 3.54 (4H, m), 3.20 (1H, m), 3.04 (1H, dd, J 14.1, 4.6 Hz), 2.69 (2H, q, J 7.5 Hz), 1.30 (3H, t, J 7.5 Hz), 1.15 (6H, t, J 7.1 Hz). m/z (ES$^+$, 70V)517 (MH$^+$).

EXAMPLE 53

Ethyl-(S)-3-[4-(3-ethyl-6-methoxy-1-isoquinolinylamino)phenyl]-2-[(2-N,N-dipropylamino-3,4-dioxocyclobut-1-enyl)amino]propanoate Prepared in a manner similar to Example 2 from the compound of Example 50 and dipropylamine to give the title compound as a pale orange solid. δH (DMSO-d$^6$, 340K) 8.78 (1H, s), 8.36 (1H, d, J 8.8 Hz), 7.86 (2H, d, J 8.6 Hz), 7.41 (1H, d, J 8.7 Hz), 7.16 (2H, d, J 8.6 Hz), 7.12 (1H, s), 7,10 (1H, d, 8.8 Hz), 6.91 (1H,s), 5.22 (1H, m), 3.91 (3H,s), 3.73 (3H, s), 3.41 (4H, m), 3.22 (1H, dd, J 14.0,4.8 Hz), 2.89 (1H, dd, J 14.0, 10.2 Hz), 2.69 (2H, q, J 7.5 Hz), 1.54 (2H, q, J 7.3 Hz), 1.52 (2H, q, J 7.3 Hz), 1.30 (3H, t, J 7.5 Hz), 0.85 (6H, t, J 7.3 Hz). m/z (ES$^+$, 70V) 559 (MH$^+$).

EXAMPLE 54

(S)-3-[4-(3-Ethyl-6-methoxy-1-isoquinolinylamino)phenyl]-2-[(2-N,N-dipropylamino-3,4-dioxocyclobut-1-enyl)amino]propanoic acid Prepared in a manner similar to Example 3 to give the title compound from the compound of Example 53 as a pale yellow glassy solid. δH (DMSO-d$^6$, 340K) 8.76 (1H, m), 8.35 (1H, d, J 8.8 Hz), 7.86 (2H, d, J 8.6 Hz), 7.27 (1H, d, J 8.9 Hz),7.17 (2H, d, J 8.6 Hz), 7.12 (1H, s), 7.09 (1H, d, J 8.8 Hz), 6.91 (3H, s), 5.13 (1H, m), 3.91 (3H, s), 3.50 (2H, m), 3.40 (2H, m), 3.22 (1H, dd, J 14.1, 4.7 Hz), 3.07 (1H, m), 2.70 (2H, q, J 7.5 Hz), 1.53 (4H, m), 1.30 (3H, t, J 7.5 Hz). 0.85 (6H, t, J 7.3 Hz). m/z (ES$^+$, 70V) 545 (MH$^+$).

EXAMPLE 55

Ethyl-(S)-3-[4-(3-ethyl-6-methoxy-1-isoquinolinylamino)phenyl]-2-[(2-[2,5-dimethylpyrrolidinyl]-3,4-dioxocyclobut-1-enyl)amino]propanoate Prepared in a manner similar to Example 2 from the compound of Example 50 and 2,5-dimethylpyrrolidine to give the title compound as an orange foamy solid. δH (DMSO-d$^6$) 8.94 (1H, s), 8.36 (1H, d, J 9.2 Hz), 7.86 (2H, d, J 8.6 Hz), 7.67 (1H, d, J 8.9 Hz), 7.18 (2H, d, J 8.6 Hz), 7.13 (1H, s), 7.10 (1H, d, J 9.2 Hz), 6.91 (1H,s ), 5.16 (1H, m), 4.19 (2H, m), 3.88 (3H, s), 3.72 (3H, s), 3.21 (1H, dd, J 13.9, 4.2 Hz), 3.03 (1H, m), 2.66 (2H, q, J 7.5 Hz), 2.08 (2H, m), 1.65 (2H, m), 1.21 (9H, m). m/z (ES$^+$, 70V) 557 (MH$^+$).

EXAMPLE 56

(S)-3-[4-(3-Ethyl-6-methoxy-1-isoquinolinylamino)phenyl]-2-[(2-(2,5-dimethylpyrrolidinyl)-3,4-dioxocyclobut-1-enyl)amino]propanoic acid Prepared in a manner similar to Example 3 from the compound of Example 55 to give the title compound as a yellow glassy solid. δH (DMSO-d$^6$, 340K) 8.76 (1H, m), 8.35 (1H, d, J 8.9 Hz), 7.84 (2H, d, J 8.6 Hz), 7.17 (2H, d, J 8.6 Hz), 7.11 (1H, s), 7.08 (1H, d, J 8.9 Hz), 6.90 (1H, s), 5.02 (1H, m), 4.21 (2H, m), 3.90 (3H, s), 3.22 (1H, dd, J 14.1, 4.7 Hz), 3.08 (1H, dd, J 14.1, 9.2 Hz), 2.69 (2H, q, J 7.5 Hz), 2.08 (2H, m), 1.67 (2H, m), 1.29 (3H, t, J 7.5 Hz), 1.27 (3H, d, J 6.4 Hz), 1.23 (3H, d, J 65.4 Hz). m /z (ES$^+$, 70V) 543 (MH$^+$).

EXAMPLE 57

Ethyl (S)-(3-[4-(3-trifluoromethyl-1-isoquinolinylamino)phenyl]-2-[(2-Isopropoxy-3,4-dioxocyclobut-1-enyl)amino]propanoate Prepared in a similar manner to that described for the compound of Example 1 from Intermediate 14 to give the title compound as an off white glass. δH (CD$_3$OD) 8.45 (1H, d, J 10.9 Hz), 7.90 (3H, m), 7.80 (2H, m), 7.50 (1H, s), 7.20 (2H, d, J 11.4 Hz), 5.21 (1H, m), 5.04, 4.60 (1H, 2×br). 4.25 (2H,q, J 9.3 Hz), 3.30 (1H,m ), 2.98 (1H, m), 1.37 (6H, d, J 8.2 Hz) and 1.30 (3H, t, J 9.3 Hz); m/z (ES$^+$, 70V) 542 (MH$^+$).

EXAMPLE 58

Ethyl-(S)-3-{4-[3-trifluoromethyl-1-isoquinolinylamino]phenyl}-2-{[2(cis-2,5-dimethylpyrrolidinyl)-3,4-dioxocyclobut-1-enyl]amino}propanoate Prepared in a similar manner to the compound of Example 2 from the compound of Example 57 and 2,5-dimethylpyrrolidine to give the title compound as an off-white glass. δH (CD$_3$OD) 8.41 (1H, d, l 10.8 Hz). 7.87 (2H, m), 7.71 (2H, m), 7.50 (1H, s), 7.21 (2H, d, J 11.4 Hz), 5.26

(1H, m), 4.25 (4H, m), 3.36 (1H, dd, J 18.8, 6.6 Hz), 3.09 (1H, dd, J 18.8. 13.4 Hz). 2.12 (2H,m ), 1.73 (2H, m) and 1.28 (9H, m). m/z (ES$^+$, 70V) 581 (MH$^+$).

EXAMPLE 59

(S)-3-{4-[3-Trifluoromethyl-1-isoquinolinylamino] phenyl}-2-{2-[(cis-2,5-dimethylpyrrolidinyl)-3,4-dioxocyclobut-1-enyl]amino}propanoic acid Prepared from the compound of Example 58 in a similar manner to that described for the compound of Example 3 to give the title compound as a white solid. δH (DMSO-d$^6$, 340K) 9.29 (1H, s), 8.62 (1H, d, J 8.3 Hz), 7.99 (1H, d, J 7.8 Hz), 7.81 (4H, m), 7.63 (1H, s), 7.22 (2H, d, J 8.6 Hz), 7.14 (1H, d, J 9.3 Hz), 5.05 (1H, m), 4.17 (2H, m), 3.24 (1H, dd, J 14.0, 4.7 Hz), 3.08 (1H, dd, J 14.0, 9.5 Hz), 2.08 (2H, m), 1.67 (2H, m), 1.25 (3H,d, J 6.4 Hz) and 1.22 (3H, d, J 6.4 Hz), m/z (ES$^+$, 70V) 553 (MH$^+$).

EXAMPLE 60

Methyl (S)-3-{4-[3-ethyl-1-isoquinolinyloxy] phenyl}-2-[(2-isopropoxy-3,4-cyclobut-1-enyl) amino]propanoate Prepared in a similar manner to that described for the compound of Example 8 from Intermediate 17 to give the title compound as a colourless glass. δH (CD$_3$OD) 8.26 (1H, d, J 8.3 Hz), 7.79 (1H, d, J 8.2 Hz), 7.70 (1H, dt, J 7.5, 1.2 Hz), 7.54 (1H, dt, J 7.6, 1.2 Hz). 7.26 (3H, m), 7.14 (2H, d, J 7.8 Hz), 5.26 (1H, m), 5.11, 4.66 (1H, 2×m), 3.79 (3H, s), 3.38 (1H, m), 3.03 (1H, m), 2.66 (2H, q, J 7.5 Hz), 1.39 (6H, m) and 1.19 (3H, t, J 7.5 Hz); m/z (ES$^+$, 70V) 489 (MH$^+$).

EXAMPLE 61

Methyl-(S)-3-{4-[3-ethyl-1-isquinolinyl)oxy] phenyl}-2-[(N,N-2-dipropylamino-3,4-dioxocyclobut-1-enyl)amino]propanoate Prepared in a similar manner to the compound of Example 2 from the compound of Example 60 and di-n-propylamine to give the title compound as a colourless glass. δH (CD$_3$OD) 8.26 (1H, d, J 8.3 Hz),7.79 (1H,d, J 8.2 Hz), 7.70 (1H, dt, J 7.5, 1.2 Hz), 7.55 (1H, dt, J 7.6, 1.3 Hz), 7.29 (2H, d, J 8.6 Hz), 7.24 (1H, s), 7.13 (2H, d, J 8.6 Hz), 5.37 (1H, dd, J 10.4, 4.8 Hz), 3.80 (3H, s), 3.51 (4H, br), 3.42 (1H, dd, J 14.2, 4.8 Hz), 3.10 (1H, dd, J 14.2, 10.4 Hz), 2.67 (2H, q, J 7.5 Hz), 1.59 (4H, m, J 7.3 Hz), 1.19 (3H, t, J 7.5 Hz) and 0.88 (3H, t, J 7.4 Hz): m/z (ES$^+$, 70V) 530 (MH$^+$).

EXAMPLE 62

(S)-3-{4-[3-Ethyl-1-isoquinolinyloxy]phenyl}-2-[(2-N,N-dipropylamino-3,4-dioxocyclobut-1-enyl) amino]propanoic acid Prepared from the compound of Example 61 in a similar manner to that described for Example 3 to give the title compound as a pale yellow solid. δH (DMSO-d$^6$, 340K) 8.27 (1H, d, J 8.3 Hz), 7.87 (1H, d, J 8.2 Hz), 7.76 (1H, t, J 7.6 Hz), 7.60 (1H, t, J 7.6 Hz), 7.31 (4H, m), 7.18 (2H, d, J 8.6 Hz), 5.19 (1H, m), 3.51 (2H, q, J 7.1 Hz), 3.41 (2H, q, J 7.1 Hz), 3.31 (1H, dd, J 14.1, 4.5 Hz), 3.11 (1H, dd, J 14.1, 10.4 Hz), 2.65 (2H, q, J 7.5 Hz), 1.54 (4H, m), 1.17 (3H, t, J 7.5 Hz) and 0.84 (6H, t, J 7.4 Hz). m/z (ES$^+$, 70V) 516 (MH$^+$).

EXAMPLE 63

Methyl-(S)-3-{4-[3-ethyl-1-isoquinolinyloxy] phenyl}-2-{[2-(cis-2,5-dimethylpyrrolidinyl)-3,4-dioxocyclobut-1-enyl]amino}propanoate Prepared in a similar manner to the compound of Example 2 from the compound of Example 60 and 2,5-dimethylpyrrolidine to give the title compound as a colourless glass. δH (CD$_3$OD) 8.27 (1H, d, J 8.4 Hz), 7.79 (1H, d, J 8.0 Hz), 7.70 (1H, t, J 7.61 Hz), 7.55 (1H, t, J 7.6 Hz), 7.1 (2H, d, J 8.6 Hz), 7.24 (1H, s), 7.14 (2H, d, J 8.6 Hz), 5.33 (1H, dd, J 10.2, 4.8 Hz), 4.23 (4H, br), 3.80 (3H, s), 3.43 (1H, dd, J 14.2, 4.8 Hz), 3.13 (1H, dd, J 14.2, 10.3 Hz), 2.67 (2H, q, J 7.5 Hz), 2.15, 1.78 (4H, s×m), 1.34 (3H, d, 6.5 Hz), 1.27 (3H, d, J 6.5 Hz) and 1.22 (3H, t, J 7.2 Hz); m/z (ES$^+$, 70V) 528 (MH$^+$).

EXAMPLE 64

(S)-3-{4-[3-Ethyl-1-isoquinolinyloxy]phenyl}-2-{[2-(cis-2,5-dimethylpyrrolidinyl)-3,4-dioxocyclobut-1-enylamino]propanoic acid Prepared from the compound of Example 63 in a similar manner to that described for Example 3 to give the title compound as a pale yellow solid. δH (DMSO-d$^6$, 340K) 8.28 (1H, d, J 8.3 Hz), 7.87 (1H, d, J 8.3 Hz), 7.76 (1H, t, J 7.6 Hz), 7.61 (1H, t, J 7.6 Hz), 7.32 (3H, m), 7.20 (3H, m), 5.15 (1H, m), 4.21 (2H, m), 3.31 (1H, dd, J 14.1, 4.6 Hz), 3.14 (1H, dd, J 14.2, 10.2 Hz), 2.65 (2H, q, 7.5 Hz), 2.12 (2H, m), 1.70 (2H, m), 1.29 (3H, d, J 6.4 Hz) 1.23 (3H, d, J 6.4 Hz) and 1.16 (6H, t, J 7.5 Hz). m/z (ES$^+$, 70V) 514 (MH$^+$).

EXAMPLE 65

Methyl (S)-3-{4-[3-trifluoromethyl-1-isoquinolinyloxy]phenyl}-2-[(2-isopropoxy-3,4-cyclobut-1-enyl)amino]propanoate Prepared in a similar manner to the compound of Example 1 from Intermediate 13 to give the title compound as a colourless solid. δH (CD$_3$OD) 8.60 (1H, d, J 8.3 Hz), 8.18 (1H, d, J 8.2 Hz), 8.02 (2H, m), 7.96 (1H, t, J 7.6 Hz), 7.45 (2H, d, J 8.6 Hz), 7.36 (2H, br s), 5.39 (1H, m), 5.24, 4.79 (1H,2×br s), 3.91 (3H, s), 3.48 (1H, m), 3.20 (1H, m), 1.53 (6H, m); m/z (ES$^+$, 70V) 529 (MH$^+$).

EXAMPLE 66

Methyl-(S)-3-{4-[3-trifluoromethyl-1-isoquinolinyloxy]phenyl}-2-[(2-N,N-dipropylamino-3,4-e-1-enyl)amino]propanoate Prepared in a similar manner to the compound of Example 2 from the compound of Example 65 and di n-propylamine to give the title compound as a colourless glass. δH (DMSO-d$^6$, 340K) 8.46 (1H, d, J 7.6 Hz), 8.19 (1H, d, J 8.1 Hz), 8.09 (1H, s), 7.98 (1H, t, J 7.6 Hz), 7.90 (1H t, J 7.7 Hz), 7.37 (1H, d), 7.35 (2H, d, J 8.7 Hz), 7.26 (2H, d, J 8.7 Hz), 5.29 (1H, m), 3.72 (3H,s), 3.46 (4H, m), 3.33 (1H, dd, J 14.1, 5.1 Hz), 3.17 (1H, dd, J 14.1, 9.9 Hz), 1.54 (4H, m) and 0.85 (6H, t, J 7.4 Hz). m/z (ES$^+$, 70V) 570 (MH$^+$).

EXAMPLE 67

(S)-3-{4-[3-Trifluoromethyl-1-isoquinolinyloxy] phenyl}-2-[(2-N,N-dipropylamino-3,4-dioxocyclobut-1-enyl)amino]propanoic acid Prepared from the compound of Example 66 in a similar manner to that described for the compound of Example 3 to give the title compound as a white solid. δH (DMSO-d$^6$, 350K) 8.46 (1H, d, J 8.4 Hz), 8.19 (1H, d, J 8.0 Hz), 8.09 (1H, s), 7.97 (1H, t, J 7.6 Hz), 7.90 (1Ha, t, J 7.6 Hz), 7.34 (2H, d, J 8.7 Hz), 7.25 (2H, d, J 8.7 Hz), 5.10 (1H, m), 3.49 (2H, m), 3.42 (2H, m), 3.33 (1H, dd, J 14.1, 4.8 Hz): 3.17

(1H, dd, J 14.1, 9.4 Hz), 1.56 (4H, m) and 0.85 (6H, t, J 7.4 Hz). m/z (ES$^+$, 70V) 556 (MH$^+$).

EXAMPLE 68

Methyl-(s)-3-{4-[3-trifluoromethyl-1-isoquinolinyloxy]phenyl}-2-{[2-(cis-2,5-dimethylpyrrolidinyl)-3,4-dioxocyclobut-1-enyl]amino}propanoate Prepared in a similar manner to the compound of Example 2 from the compound of Example 65 and 2,5-dimethyl pyrrolidine to give the title compound as a colourless glass. δH (CD$_3$OD) 8.48 (1H, d, J 8.2 Hz), 8.05 (1H, d, J 8.1 Hz), 7.90 (2H, m), 7.83 (1H, t, J 7.7 Hz), 7.35 (2H, d, J 8.6 Hz), 7.23 (2H, d, J 8.6 Hz), 5.32 (1H, m), 4.24 (1H, br), 3.79 (3H, s), 3.45 (1H, dd, J 14.2 4.9 Hz), 3.17 (1H, dd, J 14.2, 10.4 Hz), 2.16 (2H, m), 1.78 (2H, m), 1.33 (3H, d, J 6.4 Hz) and 1.28 (3H, d, J 6.4 Hz); m/z (ES$^+$, 70V) 568 (MH$^+$).

EXAMPLE 69

(S)-3,4-[3-Trifluoromethyl-1-isoquinolinyloxy]phenyl}-2-{[2-(cis-2,5-dimethylpyrrolldinyl)-3,4-dioxocyclbut-1enyl]amino}propanoic acid Prepared from Example 68 in a similar manner to that described for the compound of Example 3 to give the title compound as a white solid. δH (DMSO-d$^6$, 350K) 7.38 (2H, d, J 8.6 Hz), 7.27 (2H, d, J 8.6 Hz), 7.13 (1H, d, J 9.2 Hz), 5.16 (1H, m), 3.34 (1H, dd, J 14.2, 4.8 Hz), 3.18 (1H, dd, J 14.2, 9.8 Hz), 2.11 (2H, m), 1.71 (2H, m),1.30 (3H, d, , 6.4 Hz) and 1.24 (3H, d, J 6.4 Hz). m/z (ES$^+$, 70V) 554 (MH$^+$).

EXAMPLE 70

Ethyl (S)-3-[4-(3-chloro-1-isoquinolinylamino)phenyl]-2-[(2-N,N-diethylamino-3,4-dioxocyclobut-1-enyl)amino]propanoate Prepared in a similar manner to that described for Intermediate 3 and Example 2 from ethyl(S)-[(tert)-butoxycarbonyl)amino]-3-(4-aminophenyl)propanoate and 1,3-dichloroisoquinoline. δH (CDCl$_3$) 7.99 (1H, d, J 8.4 Hz), 7.70 (2H, d, J 8.5 Hz), 7.63–7.59 (3H, m), 7.52 (1H, m), 7.11 (1H, obs. signal), 7.10 (2H, d, J 8.5 Hz), 5.45 (1H, d, J 8.7 Hz), 5.37 (1H, m), 4.24 (2H, q, J 7.2 Hz), 3.68–3.33 (4H, br, m), 3.22 (1H, d, J 5.3 Hz), 1.31 (3H t, J 7.2 Hz), 1.22(6H, t, J 7.1 Hz); m/z (ES$^+$, 70V): 521 (MH$^+$).

EXAMPLE 71

(S)-3-[4-(3-Chloro-1-isoquinolinylamino)phenyl]-2-[(2-N,N-diethylamino-3,4-dioxocyclobut-1-enyl)amino]propanoic acid Prepared in a similar manner to that described for Example 3 from the compound of Example 70 to give the title compound. δH (d$_6$ DMSO) 9.40 (1H, s), 8.52 (1H, d, J 8.4 Hz), 7.81–7.64 (3H, m), 7.72 (2H, d, J 8.5 Hz), 7.59 (1H, t, J 6.9 Hz), 7.24 (2H, d, J 8.5 Hz), 7.23 (1H, obs. signal), 5.12–5.02 (1H,m), 3.64–3.38 (4H, br m), 3.23 (1H, dd, J 13.8, 3.0 Hz), 3.00 (1H, dd, J 13.8, 11.2 Hz), 1.09 (6H, t, J 7.1 Hz); m/z (ES$^+$, 70V) 493 (MH$^+$).

EXAMPLE 72

Methyl (S)-3-{4-[3-chloro-1-Isoquinolinyloxy]phenyl}-2-[(2-isopropoxy-3,4-cyclobut-1-enyl)amino]propanoate Prepared in a similar manner to that described for the compound of Example 1 from the Intermediate 5 and 1,2-diisopropoxy-3,4-dioxocyclobut-1-ene. δH (CD$_3$OD) 8.38 (1H, d), 7.85 (1H, t), 7.84 (1H, d), 7.67 (1H, t), 7.50 (1H, s), 7.3 (2H, d), 7.2 (2H, d), 5.3 (1H, m), 5.1 and 4.7 (1H, 2×br) 3.4 (1H, dd), 3.1 (1H, dd), 1.42 (6H: d, J 6.2 Hz). m/z (ES$^+$, 70V), 495 (MH$^+$).

EXAMPLE 73

Methyl-(S)-3-{4-[3-chloro-1-isoquinolinyloxy]phenyl}-2-[(2-t-butyl-3,4-dioxocyclobut-1-enyl)amino]propanoate Intermediate 5 (107 mg, 0.23 mmol) was dissolved in 1:1 TFA:DCM (3 ml) for 1.5 h. The reaction was concentrated and the residues taken up in MeOH (3 ml). To this solution were added the Intermediate 6 (51 mg; 0.26 mmol) and NMM (47 mg, 0.48) and the reaction heated at reflux for 5 days concentrated in vacuo and purified by chromatography (SiO$_2$; 25% EtOAc/hexane) to give the title compound (28 mg, 24%) as an off-white solid. δH (CD$_2$Cl$_2$) 8.39 (1H, d), 7.76 (2H, m), 7.64 (1H, m), 7.40 (1H, s), 7.24 (4H, s), 6.01 (1H, dt J 8.0 Hz) 5.32 (1H, m,), 3.82 (3H, s), 3.28 (2H, dd) 1.32 (9H, s). m/z (ES$^+$, 70V), 493 MH$^+$).

EXAMPLE 74

(S)-3-{4-[3-Chloro-1-isoquinolinyloxy]phenyl}-2-[(2-t-butyl-3,4-dioxocyclobut-1-enyl)amino]propanoic acid To a suspension of the compound of Example 73 (28 mg, 0.057 mmol) in 1:1 THF:H$_2$O (4 ml) was added LiOH.H$_2$O (4 mg, 0.085 mmol). After 30 min the reaction was concentrated in vacuo, the residues dissolved in water (4 ml) and to this rapidly stirring solution was added dropwise HCl (2M) to precipitate the title compound (28 mg, 100%) as an off-white solid. δH (d$_6$ DMSO) 8.62 (1H, d, J 9.0 Hz), 8.42 (1H, m), 8.02 (1H, m), 7.94 (1H, m), 7.78 (1H, m), 7.75 (1H, s), 7.41 (2H, d, J 8.5 Hz), 7.27 (2H, d, J 8.5 Hz), 5.05 (1H, m), 3.41 (1H, m), 3.17 (1H, m), 1.30 (9H, s). m/z (ES$^+$, 70V). 479 MH$^+$).

EXAMPLE 75

Methyl-(S )-3-{4-[3-chloro-1-isoquinolinyloxy]phenyl}-2-[(2-N,N-diethylamino-3,4-dioxocyclobut-1-enyl)amino]propanoate Prepared in a similar manner to the compound of Example 2 from the compound of Example 72. δH (d$_6$ DMSO) 8.34 (1H, d), 7.94 (1H, d), 7.87 (1H, t), 7.80 (1H, d), 7.71 (1H, t), 7.67 (1H, s), 7.35 (2H, d), 7.21 (2H, d), 5.24 (1H, m), 3.71 (3H, s), 3.51 (4H, br m), 3.30 (1H, m), 3.09 (1H, m), 1.09 (6H, t, J 7.1 Hz). m/z (ES$^+$, 70V), 508 MH$^+$).

EXAMPLE 76

(S)-3-{4-[3-Chloro-1-isoquinolinyloxy]phenyl}-2-[(2-N-N-diethylamino-3,4-dioxocyclobut-1-enyl)amino]propanoate Prepared in a similar manner to the compound of Example 3 from the compound of Example 75. δH (d$_6$ DMSO) 8.35 (1H, d), 7.76 (1H, d), 7.88 (1H, t), 7.72 (1H, t), 7.71 (1H, m), 7.69 (1H, s), 7.37 (2H, d, J 8.5 Hz), 7.22 (2H, d, J 8.5 Hz), 5.14 (1H, m), 3.53 (4H, br), 3.33 (1H, m), 3.11 (1H, m), 1.11 (6H, t, J 7.1 Hz). m/z (ES$^+$, 70V). 494 MH$^+$).

EXAMPLE 77

Methyl-(S)-3-{4-[3-chloro-1-isoquinolinyloxy]phenyl}-2-[2-N,N-dipropylamino-3,4-dioxocyclobut-1-enyl)amino]propanoate Prepared in a similar manner to the compound of Example 2 from the compound of Example 72 and dipropylamine to give the title compound as a colourless foam. δH (CD₃OD), 8.36 (1H, d, J 8.3 Hz), 7.80 (2H, m), 7.65 (1H, t, J 6.8 Hz), 7.47 (1H, s), 7.33 (2H, d, J 8.5 Hz), 7.18 (2H, d, J 8.5 Hz), 5.37 (1H, dd, J 10.2, 4.9 Hz), 3.80 (3H,s ), 3.50 (4H, br), 3.45 (1H, dd, J 14.2, 4.9 Hz) 3.15 (1H, dd, J 14.1, 10.2 Hz), 1.60 (4H, m), 0.89 (3H, t, J 7.4 Hz). m/z (ES⁺, 70V) 536 MH⁺).

EXAMPLE 78

Methyl-(S)-3-{4-[3-Chloro-1-isoquinolinyloxy] phenyl}-2-{[2-(N,N-dipropylamino-3,4-dioxocyclobut-1-enyl]amino}propanoic acid Prepared in a similar manner to the compound of Example 3 from the compound of Example 77 to give the title compound. δH (DMSO-d⁶), 8.35 (1H, d, J 8.3 Hz), 7.96 (1H, d, J 8.3 Hz), 7.87 (1H, t), 7.73 (1H, t), 7.66 (1H, s), 7.36 (2H, d), 7.34 (1H, d), 7.22 (2H, d, J 8.6 Hz), 5.18 (1H, m), 3.51 (2H, m), 3.42 (2H, m), 3.34 (1H, dd, J 14.1, 4.7 Hz), 3.15 (1H, dd, J 14.1, 10.2 Hz), 1.54 (4H, m), 0.45 (6H, t, J 7.4 Hz). m/z (ES⁺, 70V) 522 MH⁺).

EXAMPLE 79

Methyl-(S)-3-{4-[3-chloro-1-isoquinolinyloxy] phenyl}-2-{[-(2,5-dimethylpyrroidlinyl)-3,4-dioxocyclobut-1-enyl]amino}propanoate Prepared in a manner similar to the compound of Example 2 from the compound of Example 72 and 2,5-dimethylpyrrolidine to give the title compound as a colourless glass. δH (CD₃OD), 8.36 (1H, d, J 8.4 Hz), 7.81 (2H, m), 7.65 (1H, t, J 6.6 Hz), 7.47 (1H, s), 7.34 (2H, d, J 8.5 Hz), 7.19 (2H, d, J 8.5 Hz), 5.32 (1H, dd, J 10.1, 4.9 Hz), 4.24 (2H, br), 3.80 (3H, s), 3.45 (1H, dd, J 14.2, 4.9 Hz), 3.18 (1H, dd, J 14.2, 10.1 Hz), 2.16 (2H, m), 1.78 (2H, m), 1.33 (3H, d, J 6.5 Hz), 1.29 (3H, d, J 6.5 Hz). m/z (ES⁺, 70V) 534 (MH⁺).

EXAMPLE 80

(S)-3-{4-[3-Chloro-1-isoquinolinyloxy]phenyl}-2-{[2-(2,5-dimethylpyrrolidinyl)-3,4-dioxocyclobut-1-enyl]amino}propanoate acid Prepared in a similar manner to the compound of Example 3 from the compound of Example 79 to give the title compound as a white solid. δH (DMSO-d⁶), 8.35 (1H, d), 7.96 (1H, d), 7.87 (1H, t), 7.73 (1H, t), 7.70 (1H, s), 7.58 (1H, d), 7.38 (2H, d), 7.24 (2H, d), 5.13 (1H, m), 4.20 (2H, br), 3.33 (1H, m), 3.12 (1H, dd), 2.10 (2H, m), 1.68 (2H, m), 1.26 (3H, d, J 6.4 Hz), 1.18 (3H, d, 6.4 HZ), m/z (ES⁺, 70V) 520 MH⁺).

The following compounds were prepared in a similar manner to the compound of Example 2 from the compound of Example 72 and trans-2,5-dimethylpyrrolidine to give 2 diastereoisomers that were separated by chromatography (SiO₂;30 EtOAc, 70 Hexane) to give:

EXAMPLE 81

Methyl-(S)-3-{4-[3-chloro-1-isoquinolinyloxy] phenyl}-2-{[2-(trans-2,5-dimethylpyrrolidinyl)-3,4-dioxocyclobut-1-enyl]amino}propanoate As a white solid δH NMR (CD₃OD), 8.4 (1H, d, J 8.4 Hz), 7.95 (1H, d), 7.85 (1H, t, J 6.5 Hz), 7.7 (1H, t, J 6.6 Hz), 7.69 (1H, s), 7.4 (2H, d, J 8.4 Hz), 7.25 (2H, d, J 8.4 Hz), 5.32 (1H, dd, J 10.2, 4.8 Hz), 4.42 (2H, br) 3.8 (3H, s), 3,35 (1H, dd, J 14.1, 4.8 Hz), 3.25 (1H, dd, J 14.2, 10.2 Hz), 2.18 (2H, m), 1.68 (2H, m), 1.18 (6H, d). m/z (ES⁺, 70V) 534 MH⁺); and

EXAMPLE 82

Methyl-(R)-3-{4-[(3-chloro-1-isoquinolinyl)oxy] phenyl}-2-{[2-(trans-2,5-dimethylpyrrolidinyl)-1,4-dioxocyclobut-1-enyl]amino}propanoate As a white solid, δH NMR (CD₃OD), 8.4 (1H, d, J 8.4 Hz), 7.95 (1H, d), 7.85 (1H, t, J 6.5 Hz), 7.7 (1H, t, J 6.6 Hz), 7.69 (1H, s), 7.4 (2H, d, J 8.4 Hz), 7.25 (2H, d, J 8.4 Hz), 5.38 (1H, dd, J 10.2, 4.8 Hz), 4.42 (2H, br) 3.8 (3H, s), 3.35 (1H, dd, J 14.1, 4.8 Hz), 3.25 (1H, dd, J 14.2, 10.2 Hz), 2.18 (2H, m), 1.68 (2H, m), 1.18 (6H, d). m/z (ES⁺, 70V) 534 MH⁺).

EXAMPLE 83

(S)-3-{4-[(3-chloro-1-isoquinolinyl)oxy]phenyl}-2-{[2-(trans-2,5 -dimethylpyrrolidinyl)-3,4-dioxocyclobut-1-enyl]amino}propanoic acid Prepared in a similar manner to the compound of Example 3 from the compound of Example 81 to give the title compound as a white solid. δH NMR (DMSO-d⁶ ), 8.4 (1H, d), 7.95 (1H, d), 7.84 (1H, t), 7.71 (1H, t), 7.68 (1H, s), 7.4 (2H, d), 7.24 (2H, d), 5.21 (1H, dd, J 10.2. 4.8 Hz), 4.40 (2H, br), 3.33 (1H, dd, J 14.2, 4.9 Hz), 3.26 (1H, dd, J 14.2, 10.2 Hz), 2.17 (2H, m), 1.67 (2H, m), 1.17 (6H, d). m/z (ES⁺, 70V) 520 MH⁺).

EXAMPLE 84

(R)-3-{4-[(3-chloro-1-isoquinolinyl)oxo]phenyl}-2-{[2-(trans-2,5-dimethylpyrrolidinyl)-3,4-dioxocyclobut-1-enyl]amino}propanoic acid Prepared in a similar manner to the compound of Example 3 from the compound of Example 82 to give the title compound as a white solid. δH NMR (DMSO-d⁶), 8.4 (1H, d), 7.95 (1H, d), 7.84 (1H, t), 7.71 (1H, t), 7.68 (1H, s), 7.4 (2H, d), 7.24 (2H, d), 5.21 (1H, dd, 10.2, 4.8 Hz), 4.40 (2H, br), 3.33 (1H, dd, J 14.2, 4.9 Hz), 3.26 (1H, dd, J 14.2, 10.2 Hz), 2.17 (2H, m), 1.67 (2H, m), 1.17 (6H, d). m/z (ES⁺, 70V) 520 MH⁺).

EXAMPLE 85

Methyl-(S)-3-{4-[3-chloro-1-isoquinolinyloxy] phenyl}-2-{[2-(azepan-1-yl)-3,4-dioxocyclobut-1-enyl]amino}propanoate Prepared in a similar manner to the compound of Example 2 from the compound of Example 72 and azepane to give the title compound as a white solid. δH NMR (DMSO-d⁶), 8.51 (1H, d, J 8.2 Hz), 8.13 (1H, d, J 8.2 Hz), 8.07 (1H, t, J 5.5 Hz), 7.91 (1H, t, J 5.8 Hz), 7.86 (s, 1H), 7.69 (2H, d, J 8.5 Hz), 7.45 (2H, d, J 8.54 Hz), 5.37 (1H, dd, J 10.9, 4.5 Hz), 3.88 (3H, s), 3.67 (5H, br m), 3.27 (1H, dd, J 10.9, 11.1 Hz), 1.78 (4H, br), 1.64 (4H, br). m/z (ES⁺, 70V) 534 MH⁺).

EXAMPLE 86

(S)-3-{4-[3-Chloro-1-isoquinolinyloxy]phenyl}-2-{[(azepan-1-yl)-3,4-dioxocyclobut-1-enyl] amino}propanoic acid Prepared in a similar manner to the compound of Example 3 from the compound of Example 85 to give the title compound as a white solid. δH (DMSO-d⁶), 8.45 (1H, d, J 8.1 Hz), 8.07 (1H, d, J 8.1 Hz), 7.99 (1H, t, J 6.8 Hz), 7.85 (1H, J 6.5 Hz), 7.81 (s, 1H), 7.46 (2H, d, J 8.5 Hz), 7.36 (2H, d, J 8.54 Hz), 5.24 (1H, dd, J 11.1, 4.1 Hz), 3.77 (5H, br m), 3.17 (1H, dd, J 14, 11. Hz), 1.73 (4H, br), 1.58 (4H, br). m/z (ES⁺, 70V) 520 MH⁺).

EXAMPLE 87

(S)-3-[4-(3-Chloro-1-isoquinolinyloxy)phenyl]-2-(2-morpholino-3,4-dioxocyclobut-1-enylamino) propanoic acid A solution of the compound of Example 72 (40 mg, 0.08 mmol) in methanol (0.4 mL) was treated with morpholine (0.021 ml, 0.24 mmol) and the resulting mixture heated at 60° for 24 h. The mixture was concentrated to dryness then redissolved in anhydrous THF (2.0 ml) and treated with polystyrene methylisocyanate resin (Argonaut Technologies, 322 mg, 1.49 mmol/g, 0.48 mmol) at room temperature for 24 h. The resulting mixture was filtered, and the resin was washed with methanol (2.0 ml). The combined filtrate was evaporated to dryness then redissolved in THF (0.8 ml) and treated with an aqueous solution of lithium hydroxide monohydrate (0.4 ml of a solution of 100 mg in 4.0 ml water, 0.24 mmol) at room temperature for 24 h. The reaction mixture was quenched with glacial acetic acid (0.014 ml, 0.24 mmol), then evaporated to dryness to give the crude product which was purified by preparative HPLC to afford the title compound (3 mg). HPLC-MS Retention time 4.78 min, 508 MH⁺).

HPLC-MS Conditions: Lunca C18(2) 50×4.6 mm (3 um) column, running a gradient of 95% [0.1% aqueous formic acid], 5% [0.1% formic acid in acetonitrile] to 5% [0.1% aqueous formic acid], 95% [0.1% formic acid in acetonitrile] over 3 min, then maintaining the mobile phase at that ratio for a further 2 min. Flow rate 1.0 m/min. MS was acquired by API electrospray in positive ion mode, at 80V, scanning from 120 to 1000 amu.

The compounds of Examples 88–115 shown in Table 1 were prepared from Example 72 in a similar manner to the compound of Example 87 using the appropriate amine in place of morpholine.

The compounds of Examples 116–121 shown in Table 2 were prepared from the intermediate ethyl (S)-3-[4-(3-chloro-1-isoquinolinylamino)phenyl]-2-[(2-isopropoxy-3,4-dioxocyclobut-1-enyl)amino]propanoate [prepared in a similar manner to the compound of Example 1] in a similar manner to the compound of Example 87 using the appropriate amine in place of morpholine.

The compounds of Examples 122–158 shown in Table 3 were prepared from Example 8 in a similar manner to the compound of Example 87 using the appropriate amine in place of morpholine.

The compounds of Examples 159–167 shown in Table 4 were prepared from Example 65 in a similar manner to the compound of Example 87 using the appropriate amine in place of morpholine.

The compounds of Examples 167–174 shown in Table 5 were prepared from Example 24 in a similar manner to the compound of Example 87 using the appropriate amine in place of morpholine.

In each of the Tables 1 to 5 the letter $X_1$ indicates the point of attachment of the amine fragment (R1) to the square in the structure at the head of that table.

TABLE 1

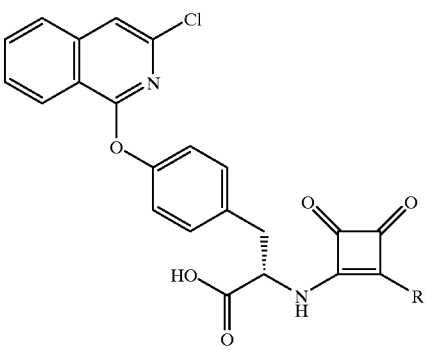

| EXAMPLE | R1 | MH+ | HPLC Retention Time (min) |
|---|---|---|---|
| EXAMPLE 88 | 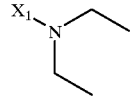 | 494 | 5.04 |
| EXAMPLE 89 | 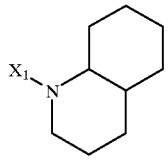 | 560 | 5.43 |
| EXAMPLE 90 | 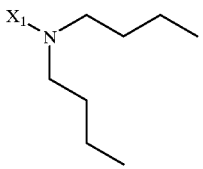 | 550 | 5.46 |
| EXAMPLE 91 | 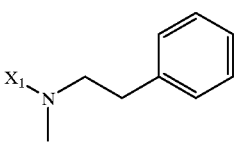 | 556 | 5.21 |
| EXAMPLE 92 | 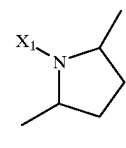 | 520 | 5.15 |
| EXAMPLE 93 | 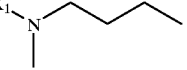 | 508 | 5.16 |
| EXAMPLE 94 | 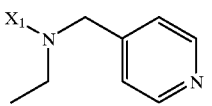 | 557 | 3.63 |
| EXAMPLE 95 | 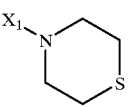 | 524 | 5.04 |

TABLE 1-continued

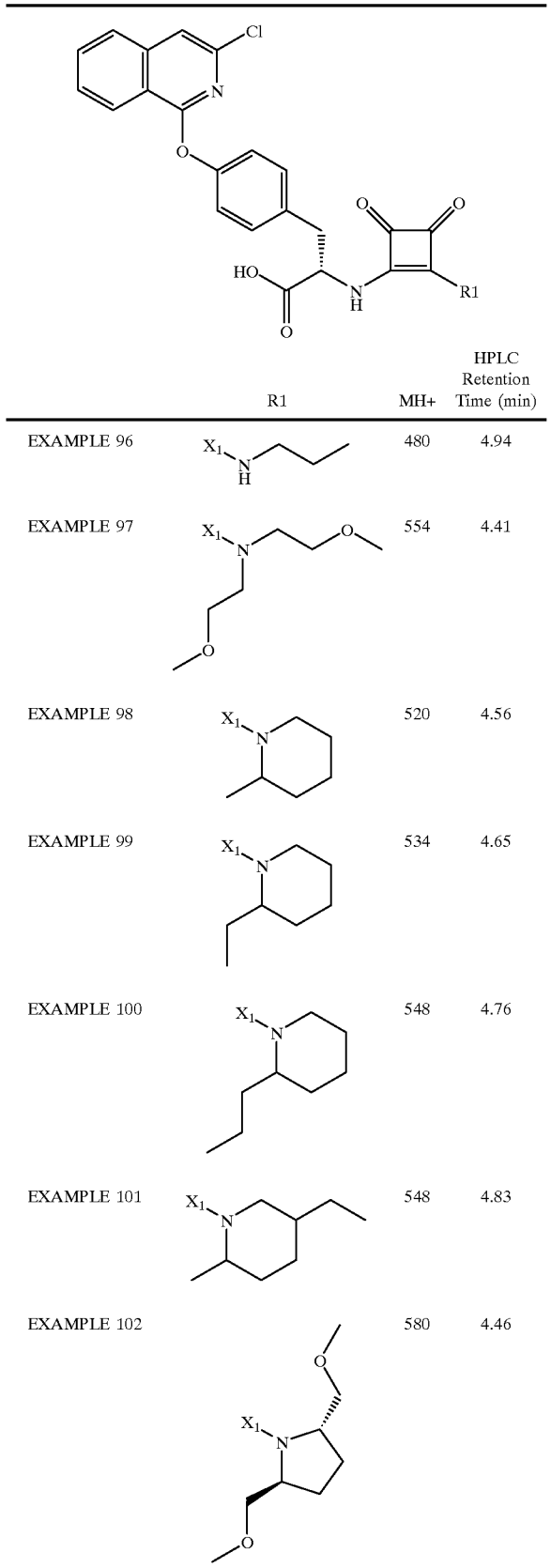

| | R1 | MH+ | HPLC Retention Time (min) |
|---|---|---|---|
| EXAMPLE 96 | X1-NH-propyl | 480 | 4.94 |
| EXAMPLE 97 | X1-N(CH2CH2OMe)2 | 554 | 4.41 |
| EXAMPLE 98 | 2-methylpiperidinyl | 520 | 4.56 |
| EXAMPLE 99 | 2-ethylpiperidinyl | 534 | 4.65 |
| EXAMPLE 100 | 2-propylpiperidinyl | 548 | 4.76 |
| EXAMPLE 101 | 2-methyl-5-ethylpiperidinyl | 548 | 4.83 |
| EXAMPLE 102 | 2,5-bis(methoxymethyl)pyrrolidinyl | 580 | 4.46 |

TABLE 1-continued

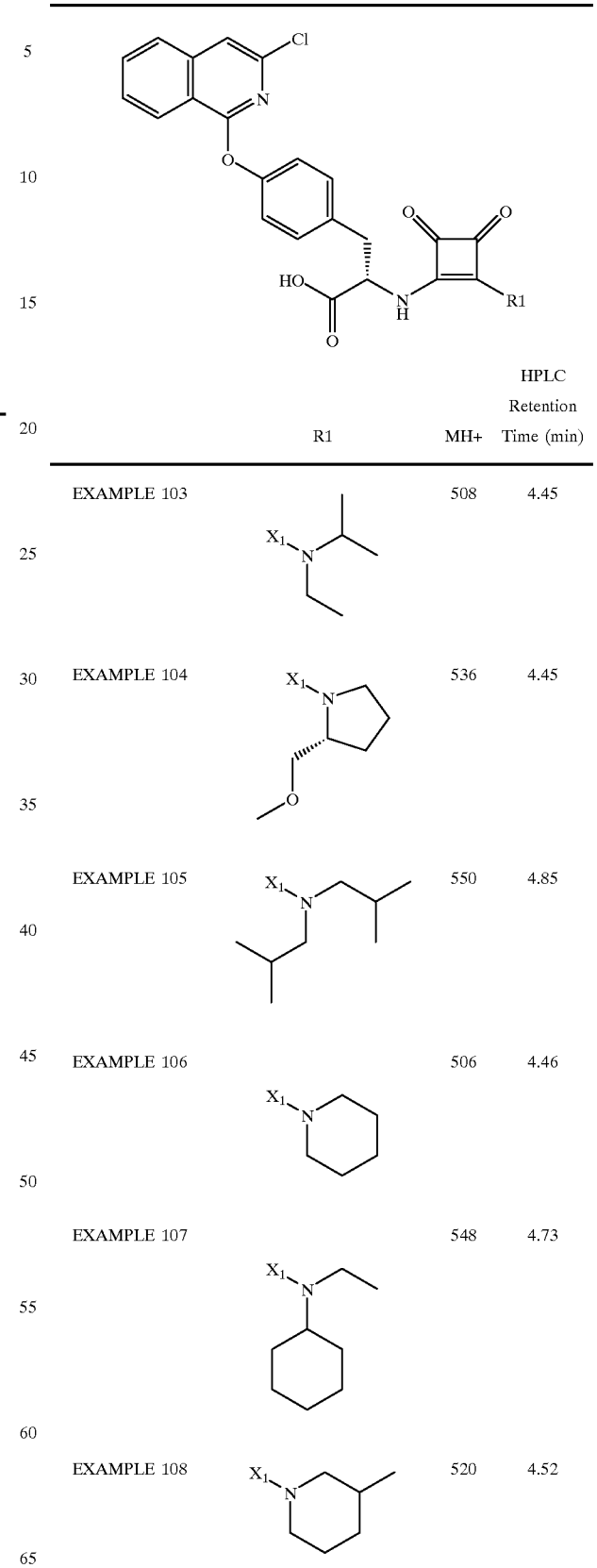

| | R1 | MH+ | HPLC Retention Time (min) |
|---|---|---|---|
| EXAMPLE 103 | X1-N(iPr)(Et) | 508 | 4.45 |
| EXAMPLE 104 | 2-(methoxymethyl)pyrrolidinyl | 536 | 4.45 |
| EXAMPLE 105 | X1-N(iBu)2 | 550 | 4.85 |
| EXAMPLE 106 | piperidinyl | 506 | 4.46 |
| EXAMPLE 107 | X1-N(Et)(cyclohexyl) | 548 | 4.73 |
| EXAMPLE 108 | 3-methylpiperidinyl | 520 | 4.52 |

TABLE 1-continued
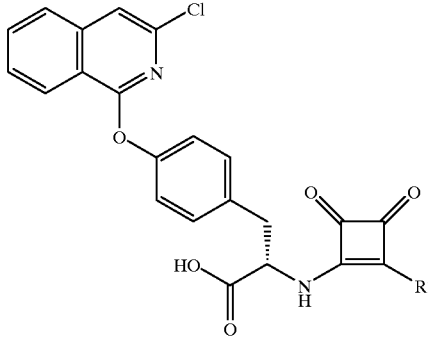
| | R1 | MH+ | HPLC Retention Time (min) |
|---|---|---|---|
| EXAMPLE 109 | 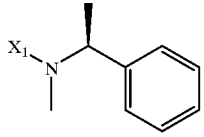 | 556 | 4.58 |
| EXAMPLE 110 | 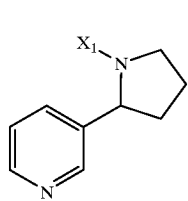 | 520 | 4.45 |
| EXAMPLE 111 | 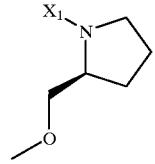 | 569 | 3.57 |
| EXAMPLE 112 | 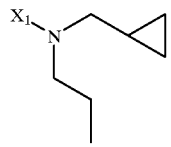 | 536 | 4.35 |
| EXAMPLE 113 | 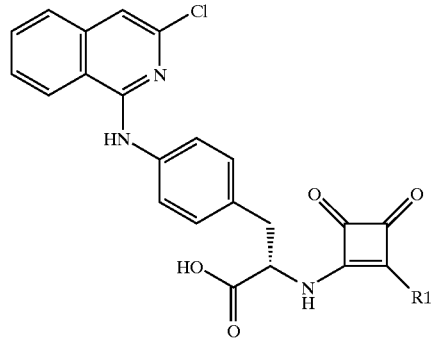 | 534 | 4.59 |
TABLE 2
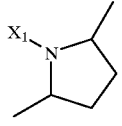
| | R1 | MH+ | HPLC Retention Time (min) |
|---|---|---|---|
| EXAMPLE 116 | 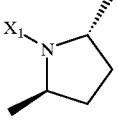 | 493 | 3.54 |
| EXAMPLE 117 | 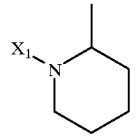 | 519 | 3.67 |
| EXAMPLE 118 | 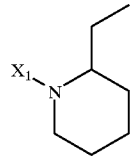 | 519 | 3.66 |
| EXAMPLE 119 | | 519 | 3.7 |
| EXAMPLE 120 | | 533 | 3.78 |
| EXAMPLE 121 | 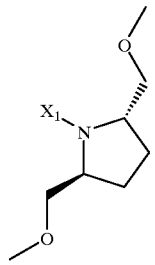 | 579 | 3.62 |

TABLE 3
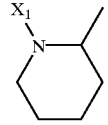
| | R1 | MH+ | HPLC Retention Time (min) |
|---|---|---|---|
| EXAMPLE 122 | 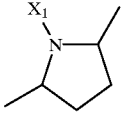 | 499 | 2.89 |
| EXAMPLE 123 | 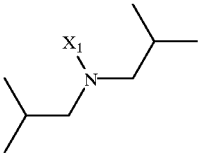 | 499 | 2.89 |
| EXAMPLE 124 | 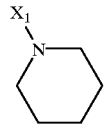 | 529 | 3.1 |
| EXAMPLE 125 | 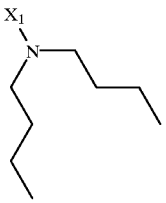 | 485 | 2.85 |
| EXAMPLE 126 | 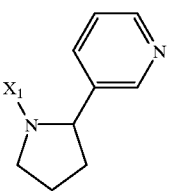 | 529 | 3.14 |
| EXAMPLE 127 | 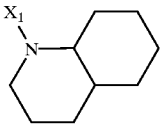 | 548 | 2.59 |
TABLE 3-continued
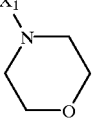
| | R1 | MH+ | HPLC Retention Time (min) |
|---|---|---|---|
| EXAMPLE 128 | 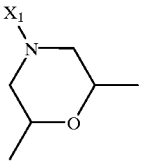 | 539 | 3.08 |
| EXAMPLE 129 | 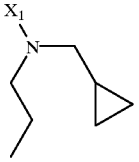 | 487 | 2.76 |
| EXAMPLE 130 | 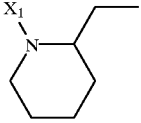 | 515 | 2.84 |
| EXAMPLE 131 | 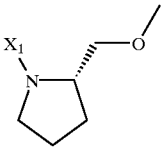 | 513 | 3.04 |
| EXAMPLE 132 | 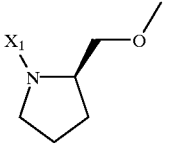 | 513 | 2.08 |
| EXAMPLE 133 | | 515 | 2.82 |
| EXAMPLE 134 | | 515 | 2.83 |

TABLE 3-continued
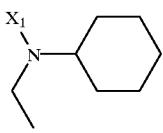
| | R1 | MH+ | HPLC Retention Time (min) |
|---|---|---|---|
| EXAMPLE 135 | 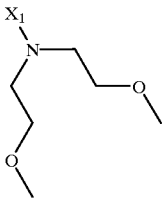 | 527 | 3.05 |
| EXAMPLE 136 | 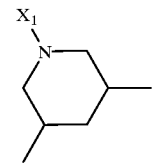 | 533 | 2.81 |
| EXAMPLE 137 | 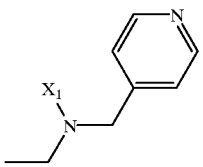 | 513 | 3 |
| EXAMPLE 138 | 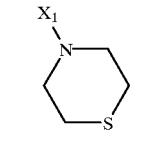 | 536 | 2.53 |
| EXAMPLE 139 | 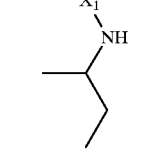 | 503 | 2.85 |
| EXAMPLE 140 | 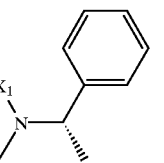 | 473 | 2.87 |
| EXAMPLE 141 | 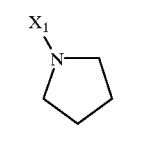 | 527 | 3.07 |
| EXAMPLE 142 | 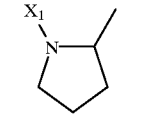 | 499 | 2.94 |
| EXAMPLE 143 | 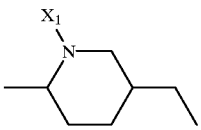 | 499 | 2.9 |
| EXAMPLE 144 | 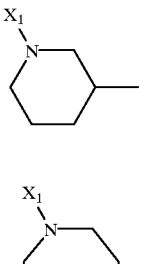 | 535 | 3.03 |
| EXAMPLE 145 | 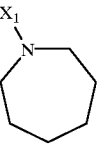 | 471 | 2.76 |
| EXAMPLE 146 | 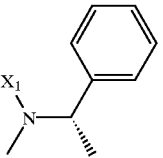 | 485 | 2.82 |

TABLE 3-continued

| | R1 | MH+ | HPLC Retention Time (min) |
|---|---|---|---|
| EXAMPLE 147 | | 521 | 2.96 |
| EXAMPLE 148 | | 553 | 3.08 |
| EXAMPLE 149 | | 559 | 2.86 |
| EXAMPLE 150 | | 487 | 2.87 |
| EXAMPLE 151 | | 473 | 2.83 |
| EXAMPLE 152 | | 513 | 2.5 |
| EXAMPLE 153 | | 533 | 2.49 |
| EXAMPLE 154 | | 549 | 2.57 |
| EXAMPLE 155 | | 600 | 2.57 |
| EXAMPLE 156 | | 489 | 2.41 |
| EXAMPLE 157 | | 535 | 2.55 |
| EXAMPLE 158 | | 499 | 2.46 |

TABLE 4
| | R1 | MH+ | HPLC Retention Time (min) |
|---|---|---|---|
| | 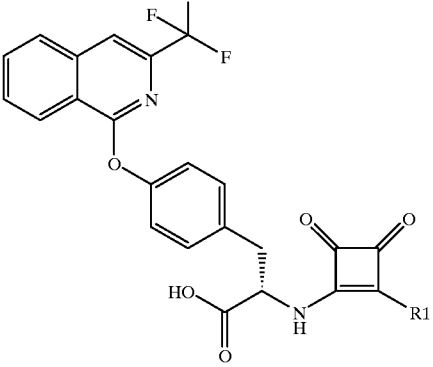 | | |
| EXAMPLE 159 | 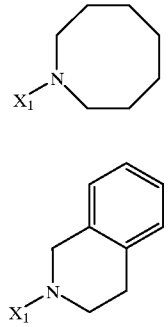 | 568 | 3.79 |
| EXAMPLE 160 | 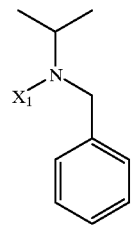 | 588 | 3.77 |
| EXAMPLE 161 | 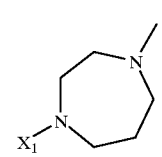 | 604 | 3.89 |
| EXAMPLE 162 | 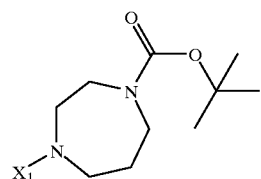 | 569 | 2.56 |
| EXAMPLE 163 | 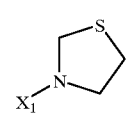 | 655 | 3.74 |
| EXAMPLE 164 | 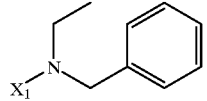 | 544 | 3.6 |
TABLE 4-continued
| | R1 | MH+ | HPLC Retention Time (min) |
|---|---|---|---|
| EXAMPLE 165 | 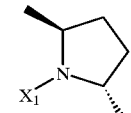 | 590 | 3.79 |
| EXAMPLE 166 | 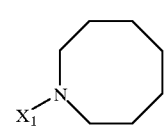 | 554 | 3.61 |
| | 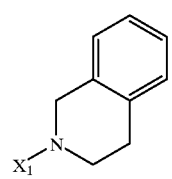 | | |
| EXAMPLE 167 | 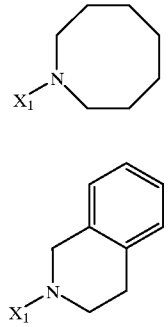 | 531 | 2.57 |
| EXAMPLE 168 | 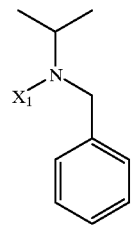 | 551 | 2.59 |
| EXAMPLE 169 | 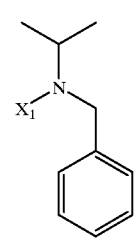 | 567 | 2.67 |
| EXAMPLE 170 | 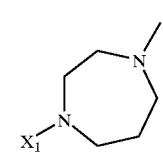 | 532 | 2.2 |

TABLE 4-continued

| | R1 | MH+ | HPLC Retention Time (min) |
|---|---|---|---|
| EXAMPLE 171 | (7-membered diazepane with N-Boc carbamate, X$_1$–N) | 618 | 2.57 |
| EXAMPLE 172 | (thiazolidine, X$_1$–N) | 507 | 2.46 |
| EXAMPLE 173 | (N-ethyl, N-benzyl amino, X$_1$–N) | 553 | 2.63 |
| EXAMPLE 174 | (2,5-dimethylpyrrolidine, X$_1$–N) | 517 | 2.51 |

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

α$_4$β$_1$ Integrin-dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 100 μl 0.25% Rose Bengal (Sigma R4507) in PBS was added for 5 minutes at room temperature and the plates washed (3×) in PBS. 100 μl 50% (v/v) ethanol in PBS was added and the plates left for 60 min after which the absorbance (570 nm) was measured.

α$_4$β$_7$ Integrin-dependent JY Cell Adhesion to MAdCAM-Ig

This assay was performed in the same manner as the α$_4$β$_1$ assay except that MAdCAM-Ig (150 ng/ml) was used in place of 2d VCAM-Ig and a sub-line of the β-lymphoblastoid cell-line JY was used in place of Jurkat cells. The IC$_{50}$ value for each test compound was determined as described in the α$_4$β$_1$ integrin assay.

α$_5$β$_1$ Integrin-dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the α$_4$β$_1$ assay above.

α$_m$β$_2$-dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of $^{200}$ μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

αIIb/β$_3$-dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the preferred compounds of the invention such as the compounds of the Examples generally have IC$_{50}$ values in the α$_4$β$_1$ and α$_4$β$_7$ assays of 1 μM and below. In the other assays featuring a integrins of other subgroups the same compounds had IC$_{50}$ values of 50 μM and above thus demonstrating the potency and selectivity of their action against α$_4$ integrins.

The advantageous clearance properties of compounds according to the invention may be demonstrated as follows:

Hepatic clearance, whether metabolic or biliary, can make a substantial contribution to the total plasma clearance of a drug. The total plasma clearance is a principal parameter of the pharmacokinetic properties of a medicine. It has a direct impact on the dose required to achieve effective plama concentrations and has a major impact on the elimination half-life and therefore the dose-interval. Furthermore, high hepatic clearance is an indicator of high first-pass hepatic clearance after oral administration and therefore low oral bioavailability.

Many peptidic and non-peptidic carboxylic acids of therapeutic interest are subject to high hepatic clearance from plasma. Except for drugs which function in the liver, hepatic uptake from blood or plasma is undesirable because it leads to high hepatic clearance if the compound is excreted in bile or metabolised, or if the substance is not cleared from the liver, it may accumulate in the liver and interfere with the normal function of the liver.

The total plasma clearance of a compound according to the invention can be determined as follows:

a small dose of the compound in solution is injected into a vein of a test animal. Blood samples are withdrawn from a blood vessel of the animal at several times after the injection, and the concentration of compound in the bleed or plasma is measured using a suitable assay. The area under the curve (AUCiv) is calculated by non-compartmental methods (for example, the trapezium method) or by pharmacokinetic modelling. The total plasma clearance ($CL_p$) is calculated by dividing the intravenous dose ($D_{iv}$) by the $AUC_{iv}$ for the blood plasma concentration–time course of a drug administered by the intravenous route: $CL_p = D_{iv} \div AUC_{iv}$ When tested in this manner, compounds according to the invention are not rapidly or extensively extracted by the liver and have low total plasma clearance where low is defined as less than 10 ml/min/kg in the laboratory rat (Sprague Dawley CD). This compares favourably with functionally equivalent integrin binding compounds in which the squaric acid framework and/or the carboxylic ester or amide R group of compounds of formula (1) is not present.

What is claimed is:

1. A compound of formula (1):

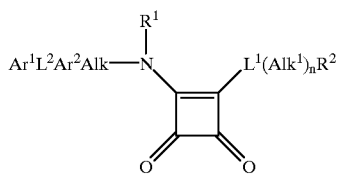

(1)

wherein $Ar^1$ is a 3-substituted isoquinolin-1-yl group;

$L^2$ is a covalent bond or a linker atom or group;

$Ar^2$ is an optionally substituted aromatic or heteroaromatic chain;

Alk is a chain

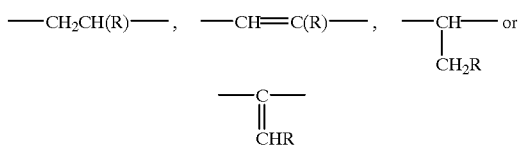

in which

R is a carboxylic acid (—$CO_2H$) or a derivative or biostere thereof;

$R^1$ is a hydrogen atom or a $C_{1-6}$alkyl group;

$L^1$ is a covalent bond or a linker atom or group;

$Alk^1$ is an optionally substituted aliphatic chain;

n is zero or the integer 1;

$R^2$ is a hydrogen atom or an optionally substituted heteroaliphatic, cycloaliphatic, heterocycloaliphatic, polycycloalphatic, heteropolycycloaliphatic, aromatic or heteroaromatic group;

and the salts, solvates, hydrates and N-oxides thereof.

2. A compound according to claim 1 in which $Alk^1$ is a chain

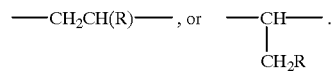

3. A compound according to claim 1 in which R is a carboxylic acid (—$CO_2H$) group.

4. A compound according to claim 1 in which R is an esterified carboxyl group of formula —$CO_2Alk^7$.

5. A compound according to claim 1 in which $Ar^2$ is an optionally substituted phenylene group.

6. A compound according to claim 1 in which $R^1$ is a hydrogen atom.

7. A compound according to claim 1 in which $L^2$ is an —O— atom or —$N(R^8)$— group.

8. A compound according to claim 7 in which $R^8$ is a hydrogen atom or a methyl group.

9. A compound according to claim 1 in which $L^1$ is a —$N(R^8)$— group where $R^8$ is a hydrogen atom or a $C_{1-6}$alkyl group.

10. A compound according to claim 1 in which $L^1$ is a covalent bond and n is the integer 1.

11. A compound according to claim 1 in which n is the integer 1 and $Alk^1$ is an optionally substituted straight or branched $C_{1-6}$alkylene chain.

12. A compound according to claim 11 in which $Alk^1$ is a —$CH_2$—, —$CH_2CH_2$—, —$CH_2CH_2CH_2$—, —$CH(CH_3)CH_2$— or —$C(CH_3)_2CH_2$— chain.

13. A compound according to claim 12 in which $R^2$ is a hydrogen atom.

14. A compound according to claim 1 in which $L^1$ is a covalent bond and n is zero.

15. A compound according to claim 14 in which $R^2$ is an optionally substituted $C_{5-7}$heterocycloaliphatic group.

16. A compound according to claim 15 in which $R^2$ is an optionally substituted piperidinyl, homopiperidinyl, heptamethyleneiminyl. pyrrolidinyl, piperazinyl, homopiperazinyl, morpholinyl or thiomorpholinyl group.

17. A compound according to claim 1 of formula (2):

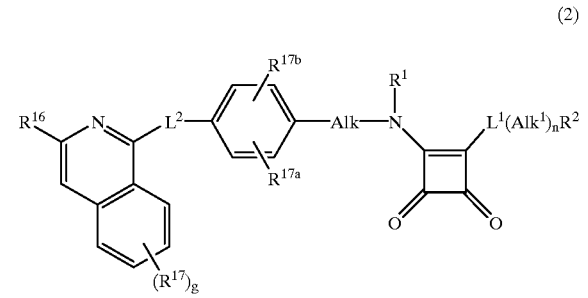

(2)

wherein g is zero or the integer 1, 2, 3, 4 or 5;

$R^{16}$ is a hydrogen atom or an atom or group —$L^3(Alk^2)_tL^4(R^4)_u$ in which;

$L^3$ is a covalent bond or a linker atom or group;

$Alk^2$ is an aliphatic or heteroaliphatic chain;

t is zero or the integer 1;

$L^4$ is a covalent bond or a linker atom or group;

$R^4$ is a hydrogen or halogen atom or a group selected from optionally substituted $C_{1-6}$alkyl or $C_{3-8}$ cycloalkyl, —$OR^5$[where $R^5$ is a hydrogen atom, an optionally substitued $C_{1-6}$alkyl or $C_{3-8}$ cycloalkyl group], —$SR^5$, —$NR^5R^6$[where $R^6$ is as just defined for $R^5$ and may be the same or different], —$NO_2$, —CN, —$CO_2R^5$, —$SO_3H$, —$SOR^5$, —$SO_2R^5$, —$SO_3R^5$, —$OCO_2R^5$, —$CONR^5R^6$, —$OCONR^5R^6$, —$CSNR^5R^6$, —$COR^5$, —$OCOR^5$, —$N(R^5)COR^6$, —$N(R^5)CSR^6$, —$SO_2N(R^5)(R^6)$, —$N(R^5)SO_2R^6$, $N(R^5)CON(R^6)(R^7)$ [where $R^7$ is a hydrogen atom, an optionally substituted $C_{1-6}$alkyl or $C_{3-8}$cycloalkyl group], —$N(R^5)CSN(R^6)(R^7)$ or —$N(R^5)SO_2N(R^6)(R^7)$, provided that when t is zero and each of $L^3$ and $L^4$ is a covalent bond then u is the integer 1 and $R^4$ is other than a hydrogen atom;

$R^{17a}$ and $R^{17b}$ is each a hydrogen or halogen atom or $C_{1-6}$alkyl, $C_{3-8}$cycloalkyl, halo$C_{1-6}$alkyl, $C_{1-6}$alkoxy, halo$C_{1-6}$alkoxy, thiol, $C_{1-6}$alkylthio, —OH, —$N(R^3)_2$[where $R^3$ is a hydrogen atom or an optionally substituted $C_{1-6}$alkyl group], —CN, —$CO_2R^3$, —$NO_2$, —$CON(R^3)_2$, —$CSN(R^3)_2$, —$COR^3$, —$CON(R^3)_2$, —$N(R^3)COR^3$, —$N(R^3)CSR^3$, —$SO_2N(R^3)_2$, —$N(R^3)SO_2R^3$, —$N(R^3)CON(R^3)_2$, —$N(R^3)CON(R^3)_2$ or —$N(R)^3SO_2N(R^3)_2$ group;

and the salts solvates, hydrates and N-oxides thereof.

18. A compound which is:

(S)-3-[4-(3-Methyl-1-isoquinolinylamino)phenyl]-2-[(2-N,N-diethylamino-3,4-dioxocyclobut-1-enyl)amino] propanoic acid;

(S)-3-[4-(3-Methyl-1-isoquinolinylamino)phenyl]-2-[2(-(trans-2,5-dimethyloyrrolidinyl)-3,4-dioxocyclobut-1-enyl)amino]propanoic acid;

(S)-3-[4-(7-Chloro-3-methyl-1-isoquinolinylamino)phenyl]-2-[(2-(cis-2,5-dimethylpyrrolidinyl)-3,4-dioxocyclobut-1-enyl)amino]propanoic acid;

(S)-3-[4-(7-Fluoro-3-methyl-1-isoquinolinylamino)phenyl]-2-[(2-N,N-diethylamino-3,4-dioxocyclobut-1-enyl)amino]propanoic acid;

(S)-3-[4-(7-Fluoro-3-methyl-1-isoquinolinylamino)phenyl]-2-[(2-(cis-2,5-dimethylpyrrolidinyl)-3,4-dioxocyclobut-1-enyl)amino]propanoic acid;

(S)-3-[4-(7-Methoxy-3-methyl-1-isoquinolinylamino)phenyl]-2-[(2-N,N-diethylamino-3,4-dioxocyclobut-1-enyl)amino]propanoic acid;

(S)-3-[4-(7-Methoxy-3-methyl-1-isoquinolinylamino)phenyl]-2-[(2-(cis-2,5-dimethylpyrrolidinyl)-3,4-dioxocyclobut-1-enyl)amino]propanoic acid;

(S)-3-{4-[3-Chloro-1-isoquinolinyloxy]phenyl}-2-[2-(N,N-dipropylamino-3,4-dioxocyclobut-1-enyl)amino]propanoic acid;

(S)-3-{4-[3-Chloro-1-isoquinolinyloxy]phenyl}-2-{[2-(trans-2,5-dimethylpyrrolidinyl)-3,4-dioxocyclobut-1-enyl]amino}propanoate;

(S)-3-{4-[(3-Chloro-1-isoquinolinyl)oxy]phenyl}-2-{[2-(trans-2,5-dimethylpyrrolidinyl)-3,4-dioxocyclobut-1-enyl]amino}propanoic acid;

(S)-3-{4-[3-Chloro-1-isoquinolinyloxy]phenyl}-2-{[(azepan-1-yl)-3,4-dioxocyclobut-1-enyl]amino}propanoic acid;

(S)-3-[4-(7-Methoxy-3-methyl-7-isoquinolinylamino)phenyl]2-[(2-azepanyl-3,4-dioxocyclobut-1-enyl)amino] propanoic acid;

and the salts solvates, hydrates, N-oxides and carboxylic acid esters, particularly the methyl, ethyl, propyl and i-propyl esters thereof.

19. A pharmaceutical composition comprising a compound according to claim 1 together with one or more pharmaceutically acceptable carriers, excipients or diluents.

* * * * *